(12) United States Patent
Luckman et al.

(10) Patent No.: US 12,402,877 B2
(45) Date of Patent: Sep. 2, 2025

(54) NEEDLE LOADER DEVICES AND RELATED SYSTEMS AND METHODS

(71) Applicant: INTUITIVE SURGICAL OPERATIONS, INC., Sunnyvale, CA (US)

(72) Inventors: Jake Anthony Luckman, Sunnyvale, CA (US); Ronald George Litke, Jr., Sunnyvale, CA (US); Jorge Alberto Trevino Blanco, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 481 days.

(21) Appl. No.: 17/833,845

(22) Filed: Jun. 6, 2022

(65) Prior Publication Data
US 2022/0387020 A1  Dec. 8, 2022

Related U.S. Application Data

(60) Provisional application No. 63/197,786, filed on Jun. 7, 2021.

(51) Int. Cl.
*A61B 17/062* (2006.01)
*A61B 17/06* (2006.01)

(52) U.S. Cl.
CPC .... *A61B 17/062* (2013.01); *A61B 2017/0608* (2013.01); *A61B 2017/06142* (2013.01)

(58) Field of Classification Search
CPC ............ A61B 17/06114; A61B 17/062; A61B 2017/0608; A61B 2017/06142;
(Continued)

(56) References Cited

U.S. PATENT DOCUMENTS 1,327,577 A   1/1920  Turner
1,822,330 A   9/1931  George et al.
(Continued)

FOREIGN PATENT DOCUMENTS

CN     2169381 Y    6/1994
CN   201082170 Y    7/2008
(Continued)

OTHER PUBLICATIONS

Decision of Refusal Issued in Japanese Application No. 2015-112857, mailed Dec. 8, 2016, 3 pages.
(Continued)

*Primary Examiner* — Mohamed G Gabr
(74) *Attorney, Agent, or Firm* — DeWitt LLP; Brian R. Pollack, Esq.

(57) ABSTRACT

Implementations of a needle loader and related methods are provided. The needle loader comprises a housing, a movable arm disposed within the housing, and a needle mount defined on the movable arm to releasably attach to an arced suturing needle. The needle loader further includes an arced needle releasably attached to the needle mount. The needle can be held in place on the needle mount by way of an interference fit. The needle mount can be defined on a surface of the movable arm that faces an arced needle track of a suturing device when loading an arced suturing needle in the needle track of the suturing device.

22 Claims, 36 Drawing Sheets

(58) Field of Classification Search
CPC ............ A61B 17/0469; A61B 17/0482; A61B 17/06133; A61B 2017/00115; A61B 2017/0053; A61B 2017/00876; A61B 17/0625; A61B 17/0491; A61B 17/06066; A61B 2017/0479

See application file for complete search history.

(56) References Cited

U.S. PATENT DOCUMENTS

| | | |
|---|---|---|
| 2,327,353 A | 8/1943 | Karle |
| 2,601,564 A | 6/1952 | Smith |
| 3,197,997 A | 8/1965 | Kurtz |
| 3,311,110 A | 3/1967 | Singerman et al. |
| 3,344,790 A | 10/1967 | Dorner |
| 3,762,418 A | 10/1973 | Wasson |
| 3,834,599 A | 9/1974 | Herr |
| 3,835,912 A | 9/1974 | Kristensen et al. |
| 3,910,282 A | 10/1975 | Messer et al. |
| 3,951,261 A | 4/1976 | Mandel et al. |
| 3,972,418 A | 8/1976 | Schuler et al. |
| 4,027,608 A | 6/1977 | Arbuckle |
| 4,074,732 A | 2/1978 | Wilkens |
| 4,235,177 A | 11/1980 | Arbuckle |
| 4,327,655 A | 5/1982 | Addy et al. |
| 4,331,277 A | 5/1982 | Green |
| 4,437,465 A | 3/1984 | Nomoto et al. |
| 4,509,945 A | 4/1985 | Kramann et al. |
| 4,527,564 A | 7/1985 | Eguchi et al. |
| 4,557,265 A | 12/1985 | Andersson |
| 4,621,640 A | 11/1986 | Mulhollan et al. |
| 4,841,888 A | 6/1989 | Mills et al. |
| 4,899,746 A | 2/1990 | Brunk |
| 4,957,502 A | 9/1990 | Takase |
| 5,080,663 A | 1/1992 | Mills et al. |
| 5,089,012 A | 2/1992 | Prou |
| 5,174,300 A | 12/1992 | Bales et al. |
| 5,201,760 A | 4/1993 | West |
| 5,210,376 A | 5/1993 | Caviar |
| 5,269,806 A | 12/1993 | Sardelis et al. |
| 5,305,281 A | 4/1994 | Lubeck |
| 5,306,281 A | 4/1994 | Beurrier |
| 5,308,353 A | 5/1994 | Beurrier |
| 5,318,566 A | 6/1994 | Miller |
| 5,318,578 A | 6/1994 | Hasson |
| 5,330,502 A | 7/1994 | Hassler et al. |
| 5,344,061 A | 9/1994 | Crainich |
| 5,358,498 A | 10/1994 | Shave |
| 5,364,408 A | 11/1994 | Gordon |
| 5,373,101 A | 12/1994 | Barabolak |
| 5,376,101 A | 12/1994 | Green et al. |
| 5,387,221 A | 2/1995 | Bisgaard |
| 5,403,344 A | 4/1995 | Allen |
| 5,437,681 A | 8/1995 | Meade et al. |
| 5,454,819 A | 10/1995 | Knoepfler |
| 5,462,558 A | 10/1995 | Kolesa et al. |
| 5,472,081 A | 12/1995 | Kilgrow et al. |
| 5,474,568 A | 12/1995 | Scott |
| 5,478,344 A | 12/1995 | Stone et al. |
| 5,478,345 A | 12/1995 | Stone et al. |
| 5,480,409 A | 1/1996 | Riza |
| 5,503,266 A | 4/1996 | Kalbfeld et al. |
| 5,514,159 A | 5/1996 | Matula et al. |
| 5,540,705 A | 7/1996 | Meade et al. |
| 5,571,119 A | 11/1996 | Atala |
| 5,575,800 A | 11/1996 | Gordon |
| 5,578,044 A | 11/1996 | Gordon et al. |
| 5,643,295 A | 7/1997 | Yoon |
| 5,645,552 A | 7/1997 | Sherts |
| 5,665,096 A | 9/1997 | Yoon |
| 5,665,109 A | 9/1997 | Yoon |
| 5,669,490 A | 9/1997 | Colligan et al. |
| 5,675,961 A | 10/1997 | Cerwin et al. |
| 5,709,693 A | 1/1998 | Taylor |
| 5,713,910 A | 2/1998 | Gordon et al. |
| 5,715,942 A | 2/1998 | Li et al. |
| 5,741,277 A | 4/1998 | Gordon et al. |
| 5,755,729 A | 5/1998 | De La Torre et al. |
| 5,759,188 A | 6/1998 | Yoon |
| 5,766,186 A | 6/1998 | Faraz et al. |
| 5,814,069 A | 9/1998 | Schulze et al. |
| 5,814,071 A | 9/1998 | McDevitt et al. |
| 5,830,234 A | 11/1998 | Wojciechowicz et al. |
| 5,833,695 A | 11/1998 | Yoon |
| 5,860,992 A | 1/1999 | Daniel et al. |
| 5,891,160 A | 4/1999 | Williamson, IV et al. |
| 5,906,273 A | 5/1999 | Pohle et al. |
| 5,908,426 A | 6/1999 | Pierce |
| 5,908,428 A | 6/1999 | Scirica et al. |
| 5,911,727 A | 6/1999 | Taylor |
| 5,954,733 A | 9/1999 | Yoon |
| 5,968,077 A | 10/1999 | Wojciechowicz et al. |
| 5,993,466 A | 11/1999 | Yoon |
| 6,016,905 A | 1/2000 | Gemma et al. |
| 6,036,694 A | 3/2000 | Goble et al. |
| 6,048,351 A | 4/2000 | Gordon et al. |
| 6,053,908 A | 4/2000 | Crainich et al. |
| 6,056,771 A | 5/2000 | Proto |
| 6,071,289 A | 6/2000 | Stefanchik et al. |
| 6,096,051 A | 8/2000 | Kortenbach et al. |
| 6,126,666 A | 10/2000 | Trapp et al. |
| 6,135,385 A | 10/2000 | Martinez De Lahidalga |
| 6,136,010 A | 10/2000 | Modesitt et al. |
| 6,159,224 A | 12/2000 | Yoon |
| 6,261,307 B1 | 7/2001 | Yoon et al. |
| 6,270,508 B1 | 8/2001 | Klieman et al. |
| 6,322,581 B1 | 11/2001 | Fukuda et al. |
| 6,332,888 B1 | 12/2001 | Levy et al. |
| 6,346,111 B1 | 2/2002 | Gordon et al. |
| 6,443,962 B1 | 9/2002 | Gaber |
| 6,454,777 B1 | 9/2002 | Green |
| 6,454,778 B2 | 9/2002 | Kortenbach |
| 6,494,888 B1 | 12/2002 | Laufer et al. |
| 6,506,196 B1 | 1/2003 | Laufer |
| 6,558,400 B2 | 5/2003 | Deem et al. |
| 6,656,194 B1 | 12/2003 | Gannoe et al. |
| 6,663,639 B1 | 12/2003 | Laufer et al. |
| 6,719,763 B2 | 4/2004 | Chung et al. |
| 6,719,764 B1 | 4/2004 | Gellman et al. |
| 6,746,460 B2 | 6/2004 | Gannoe et al. |
| 6,755,843 B2 | 6/2004 | Chung et al. |
| 6,835,200 B2 | 12/2004 | Laufer et al. |
| 6,877,352 B1 | 4/2005 | Schlereth |
| 6,908,427 B2 | 6/2005 | Fleener et al. |
| 6,923,819 B2 | 8/2005 | Meade et al. |
| 6,955,643 B2 | 10/2005 | Gellman et al. |
| 7,004,951 B2 | 2/2006 | Gibbens, III |
| 7,033,370 B2 | 4/2006 | Gordon et al. |
| 7,041,111 B2 | 5/2006 | Chu |
| 7,144,401 B2 | 12/2006 | Yamamoto et al. |
| 7,166,116 B2 | 1/2007 | Lizardi et al. |
| 7,338,504 B2 | 3/2008 | Gibbens et al. |
| 7,615,060 B2 | 11/2009 | Stokes et al. |
| 7,628,796 B2 | 12/2009 | Shelton, IV et al. |
| 7,637,909 B2 | 12/2009 | Lechot et al. |
| 7,766,925 B2 | 8/2010 | Stokes et al. |
| 7,828,812 B2 | 11/2010 | Stokes et al. |
| 7,833,236 B2 | 11/2010 | Stokes et al. |
| 7,846,169 B2 | 12/2010 | Shelton, IV et al. |
| 7,862,572 B2 | 1/2011 | Meade et al. |
| 7,887,554 B2 | 2/2011 | Stokes et al. |
| 7,976,533 B2 | 7/2011 | Larsson |
| 7,976,555 B2 | 7/2011 | Meade et al. |
| 7,993,354 B1 | 8/2011 | Brecher et al. |
| 8,066,737 B2 | 11/2011 | Meade et al. |
| 8,123,764 B2 | 2/2012 | Meade et al. |
| 8,469,973 B2 | 6/2013 | Meade et al. |
| 8,500,756 B2 | 8/2013 | Papa et al. |
| 8,623,048 B2 | 1/2014 | Brecher et al. |
| 8,641,728 B2 | 2/2014 | Stokes et al. |
| 8,702,732 B2 | 4/2014 | Woodard, Jr. et al. |
| 8,906,043 B2 | 12/2014 | Woodard, Jr. et al. |
| 9,125,645 B1 | 9/2015 | Martin et al. |
| 9,173,655 B2 | 11/2015 | Martin |
| 9,220,496 B2 | 12/2015 | Martin et al. |

(56) References Cited

U.S. PATENT DOCUMENTS

| | | |
|---|---|---|
| 9,357,998 B2 | 6/2016 | Martin et al. |
| 9,370,354 B1* | 6/2016 | Martin ............... A61B 17/0625 |
| 9,375,212 B2 | 6/2016 | Martin et al. |
| 9,398,905 B2 | 7/2016 | Martin |
| 9,427,226 B2 | 8/2016 | Martin et al. |
| 9,427,227 B2 | 8/2016 | Martin et al. |
| 9,445,807 B2 | 9/2016 | John et al. |
| 9,451,948 B2 | 9/2016 | Meade et al. |
| 9,474,522 B2 | 10/2016 | Deck et al. |
| 9,474,523 B2 | 10/2016 | Meade et al. |
| 9,486,209 B2 | 11/2016 | Martin et al. |
| 9,498,207 B2 | 11/2016 | Martin et al. |
| 9,526,495 B2 | 12/2016 | Martin et al. |
| 10,070,858 B2 | 9/2018 | Shelton, IV et al. |
| 10,238,381 B1 | 3/2019 | Martin et al. |
| 2002/0107530 A1 | 8/2002 | Sauer et al. |
| 2002/0173800 A1 | 11/2002 | Dreyfuss et al. |
| 2003/0105475 A1 | 6/2003 | Sancoff et al. |
| 2003/0171760 A1 | 9/2003 | Gambale |
| 2003/0181924 A1 | 9/2003 | Yamamoto et al. |
| 2003/0233104 A1 | 12/2003 | Gellman et al. |
| 2004/0034369 A1 | 2/2004 | Sauer et al. |
| 2004/0044354 A1 | 3/2004 | Gannoe et al. |
| 2004/0082963 A1 | 4/2004 | Gannoe et al. |
| 2004/0088008 A1 | 5/2004 | Gannoe et al. |
| 2004/0122473 A1 | 6/2004 | Ewers et al. |
| 2004/0138682 A1 | 7/2004 | Onuki et al. |
| 2004/0147941 A1 | 7/2004 | Takemoto et al. |
| 2004/0147958 A1 | 7/2004 | Lam et al. |
| 2004/0162568 A1 | 8/2004 | Saadat et al. |
| 2004/0181243 A1 | 9/2004 | Chu et al. |
| 2004/0194790 A1 | 10/2004 | Laufer et al. |
| 2004/0210243 A1 | 10/2004 | Gannoe et al. |
| 2004/0260344 A1 | 12/2004 | Lyons et al. |
| 2005/0015101 A1 | 1/2005 | Gibbens, III et al. |
| 2005/0035007 A1 | 2/2005 | Kennedy et al. |
| 2005/0055038 A1 | 3/2005 | Kelleher et al. |
| 2005/0070931 A1 | 3/2005 | Li et al. |
| 2005/0075653 A1 | 4/2005 | Saadat et al. |
| 2005/0262984 A1 | 12/2005 | Hetcher et al. |
| 2006/0224184 A1 | 10/2006 | Stefanchik et al. |
| 2006/0282097 A1 | 12/2006 | Ortiz et al. |
| 2006/0282098 A1 | 12/2006 | Shelton, IV et al. |
| 2006/0282099 A1 | 12/2006 | Stokes et al. |
| 2007/0135838 A1 | 6/2007 | Meyer |
| 2007/0239177 A1* | 10/2007 | Stokes ............... A61B 17/0469 606/144 |
| 2008/0132919 A1 | 6/2008 | Chui et al. |
| 2008/0140091 A1 | 6/2008 | DeDeyne et al. |
| 2010/0036415 A1 | 2/2010 | Cabezas |
| 2010/0049219 A1 | 2/2010 | Cronin et al. |
| 2010/0130990 A1 | 5/2010 | Saliman |
| 2014/0171977 A1 | 6/2014 | Martin et al. |
| 2014/0171979 A1 | 6/2014 | Martin et al. |
| 2014/0172015 A1 | 6/2014 | Martin et al. |
| 2015/0133967 A1 | 5/2015 | Martin |
| 2015/0351745 A1 | 12/2015 | Mumaw et al. |
| 2015/0351746 A1 | 12/2015 | Martin et al. |
| 2015/0351749 A1 | 12/2015 | Martin et al. |
| 2015/0351756 A1 | 12/2015 | Martin et al. |
| 2016/0030036 A1 | 2/2016 | Belman et al. |
| 2016/0317148 A1 | 11/2016 | Martinez |
| 2016/0331374 A1 | 11/2016 | Martin et al. |
| 2016/0345958 A1 | 12/2016 | Martin et al. |
| 2016/0346827 A1 | 12/2016 | Martin et al. |
| 2016/0361055 A1 | 12/2016 | Martin et al. |
| 2016/0367238 A1 | 12/2016 | Deck et al. |
| 2016/0367239 A1 | 12/2016 | Mumaw et al. |
| 2016/0367243 A1 | 12/2016 | Martin et al. |
| 2017/0095235 A1* | 4/2017 | Harrison ............ A61B 17/0483 |
| 2018/0256160 A1* | 9/2018 | Kurd ................. A61B 17/0491 |
| 2019/0117215 A1* | 4/2019 | Belman ............. A61B 17/0625 |

FOREIGN PATENT DOCUMENTS

| | | |
|---|---|---|
| DE | 4310315 A1 | 10/1993 |
| EP | 0556270 A1 | 8/1993 |
| EP | 0648474 A1 | 4/1995 |
| EP | 1733685 A1 | 12/2006 |
| EP | 1839591 A1 | 10/2007 |
| EP | 2103262 A1 | 9/2009 |
| EP | 2292157 A2 | 3/2011 |
| EP | 2308391 A1 | 4/2011 |
| EP | 2370002 A2 | 10/2011 |
| EP | 1791476 B1 | 12/2015 |
| FR | 2540377 A1 | 8/1984 |
| GB | 18602 | 9/1908 |
| JP | S55151956 A | 11/1980 |
| JP | H07178100 A | 7/1995 |
| JP | H07328021 A | 12/1995 |
| JP | H11276492 A | 10/1999 |
| JP | 2000139931 A | 5/2000 |
| JP | 2005080761 A | 3/2005 |
| JP | 2005253987 A | 9/2005 |
| WO | WO-9609796 A2 | 4/1996 |
| WO | WO-9729694 A1 | 8/1997 |
| WO | WO-9912482 A1 | 3/1999 |
| WO | WO-9940850 A1 | 8/1999 |
| WO | WO-9947050 A2 | 9/1999 |
| WO | WO-0112084 A1 | 2/2001 |
| WO | WO-02102226 A2 | 12/2002 |
| WO | WO-03028541 A2 | 4/2003 |
| WO | WO-2004012606 A1 | 2/2004 |
| WO | WO-2004021894 A1 | 3/2004 |
| WO | WO-2004028402 A2 | 4/2004 |
| WO | WO-2004086986 A1 | 10/2004 |
| WO | WO-2006034209 A2 | 3/2006 |
| WO | WO-2007089603 A2 | 8/2007 |
| WO | WO-2008147555 A2 | 12/2008 |
| WO | WO-2010062380 A2 | 6/2010 |

OTHER PUBLICATIONS

Decision on Petition for Inter Partes Review of U.S. Pat. No. 6,923,819, filed Apr. 28, 2016, IPR2016-00071, 17 pages.

English Translation of Office Action mailed Jan. 4, 2011 for Japanese Application No. JP2007-532595, 2 pages.

Ethicon Exhibit 1001 in IPR Case No. 2016-00071; U.S. Pat. No. 6,923,819, issued Aug. 2, 2005, 32 pages.

Ethicon Exhibit 1002 in IPR Case No. 2016-00071; Prosecution History of U.S. Appl. No. 10/127,254, filed Apr. 22, 2002, 359 pages.

Ethicon Exhibit 1003 in IPR Case No. 2016-00071; Expert Declaration of Kevin L. Houser, M.S., dated Oct. 22, 2015, 105 pages.

Ethicon Exhibit 1004 in IPR Case No. 2016-00071; U.S. Pat. No. 5,437,681, issued Aug. 1, 1995, 15 pages.

Ethicon Exhibit 1005 in IPR Case No. 2016-00071; U.S. Pat. No. 5,306,281, issued Apr. 26, 1994, 12 pages.

Ethicon Exhibit 1006 in IPR Case No. 2016-00071; U.S. Pat. No. 4,557,265, issued Dec. 10, 1985, 4 pages.

Ethicon Exhibit 1007 in IPR Case No. 2016-00071; U.S. Pat. No. 6,053,908, issued Apr. 25, 2000, 9 pages.

Ethicon Exhibit 1008 in IPR Case No. 2016-00071; U.S. Pat. No. 5,911,727, issued Jun. 15, 1999, 12 pages.

Ethicon Exhibit 1009 in IPR Case No. 2016-00071; N. Chironis, Mechanisms, Linkages, and Mechanical Control, 5th ed. 1965, 8 pages.

Ethicon Exhibit 1010 in IPR Case No. 2016-00071; "Webster's New Universal Unabridged Dictionary," 2nd Edition 1983, 4 pages.

Examination Report issued by Hungarian IP Office on behalf of Singapore IP Office dated Feb. 8, 2012 in connection with Singapore Application No. 200907505-2.

Exhibit 2001 in IPR Case No. 2016-00071; U.S. Pat. No. 5,709,693, issued Jan. 20, 1998, 7 pages.

Extended European Search Report for Application No. EP05797831.4, mailed on Feb. 25, 2011, 7 pages.

Extended European Search Report for Application No. 07762862.6, mailed on Mar. 11, 2011, 11 pages.

(56) References Cited

OTHER PUBLICATIONS

Extended European Search Report for Application No. 12822057.1, mailed on Jun. 5, 2015, 10 pages.
Extended European Search Report for Application No. EP10009831.8, mailed on Feb. 21, 2011, 7 pages.
Extended European Search Report for Application No. EP10009832.6, mailed on Feb. 9, 2011.
Extended European Search Report for Application No. EP11830008.6, mailed on Aug. 14, 2015, 08 pages.
Extended European Search Report for Application No. 09829467.1., mailed on Nov. 29, 2012, 6 pages.
International Preliminary Report on Patentability for Application No. PCT/US05/33507, mailed on Jun. 13, 2008, 5 pages.
International Search Report for Application No. PCT/US09/006212, mailed Jul. 5, 2010, 4 pages.
International Search Report and Written Opinion for Application No. PCT/US11/054334, mailed Apr. 24, 2012, 8 pages.
International Preliminary Report on Patentability and Written Opinion for Application No. PCT/US07/02204, mailed on Jan. 27, 2006, 7 pages.
International Preliminary Report on Patentability for Application No. PCT/US08/006674, mailed on Nov. 24, 2009, 5 pages.
International Preliminary Report on Patentability for Application No. PCT/US02/12560, mailed on Mar. 12, 2004, 6 pages.
International Preliminary Report on Patentability for Application No. PCT/US12/049979, mailed on Feb. 11, 2014, 4 pages.
International Search Report and Written Opinion for Application No. PCT/US05/33507, mailed on Jun. 13, 2008, 5 pages.
International Search Report and Written Opinion for Application No. PCT/US08/006674, mailed on Jan. 5, 2009, 6 pages.
International Search Report and Written Opinion for Application No. PCT/US02/12560, mailed on Mar. 3, 2003.
International Search Report and Written Opinion for Application No. PCT/US09/06212, mailed on Jul. 5, 2010, 8 pages.
International Search Report and Written Opinion for International Application for Application No. PCT/US07/002204, mailed on Nov. 1, 2007, 7 pages.
Non-Final Office Action mailed Nov. 7, 2012 for U.S. Appl. No. 15/260,094, filed Jan. 17, 2017, 14 pages.
Office Action dated Jul. 1, 2014 from Corresponding Japanese Application No. 2013-138559, 4 pages.
Office Action mailed Oct. 18, 2011 for Japanese Application No. 2008-552444, 11 pages.
Office Action mailed Oct. 18, 2017 for Japanese Application No. 2016-187970.
Patent Owner's Preliminary Response, filed Jan. 29, 2016, 1PR2016-00071, 49 pages.
Petition for Inter Partes Review of U.S. Pat. No. 6,923,819, filed Oct. 22, 2015, 64 pages.
Preliminary Amendment mailed Nov. 3, 2010 for U.S. Appl. No. 15/260,094, filed Nov. 18, 2016, 7 pages.
Search Report for SG Application No. 200805426-4 dated May 20, 2010, 3 pages.
Supplementary European Search Report of Application No. 02725747.6, mailed on Oct. 9, 2006, 6 pages.
Supplementary European Search Report of Application No. 02725747.6, mailed on Mar. 23, 2007, 6 pages.
Supplementary European Search Report of Application No. EP140654.5, mailed on Mar. 15, 2007, 5 pages.
Written Opinion for Singapore Application No. 200907505-2, mailed on Jan. 11, 2011, 8 pages.
U.S. Appl. No. 08/180,662; U.S. Pat. No. 5,437,681, filed Jan. 13, 1994.
U.S. Appl. No. 08/445,359; U.S. Pat. No. 5,540,705, filed May 19, 1995.
U.S. Appl. No. 10/127,254; U.S. Pat. No. 6,923,819, filed Apr. 22, 2002.
U.S. Appl. No. 11/121,810 (abandoned), filed May 4, 2005.
U.S. Appl. No. 11/387,127; U.S. Pat. No. 8,066,737, filed Mar. 22, 2006.
U.S. Appl. No. 13/197,698; U.S. Pat. No. 8,623,048, filed Aug. 3, 2011.
U.S. Appl. No. 13/197,870; U.S. Pat. No. 9,445,807, filed Aug. 4, 2011.
U.S. Appl. No. 15/260,094; U.S. Pat. No. 9,649,107, filed Sep. 8, 2016.
U.S. Appl. No. 15/377,373 (abandoned), filed Dec. 13, 2016.
U.S. Appl. No. 15/377,425 (abandoned), filed Dec. 13, 2016.
U.S. Appl. No. 15/404,394 (abandoned), filed Jan. 12, 2017.
U.S. Appl. No. 15/404,405; U.S. Pat. No. 9,693,770, filed Jan. 12, 2017.
U.S. Appl. No. 15/476,531; U.S. Pat. No. 9,743,923, filed Mar. 31, 2017.
U.S. Appl. No. 15/476,958; U.S. Pat. No. 9,743,925, filed Mar. 31, 2017.
U.S. Appl. No. 15/476,968; U.S. Pat. No. 9,717,495, filed Mar. 31, 2017.
U.S. Appl. No. 15/490,539; U.S. Pat. No. 9,717,493, filed Apr. 18, 2017.
U.S. Appl. No. 15/490,611; U.S. Pat. No. 9,730,688, filed Apr. 18, 2017.
U.S. Appl. No. 15/490,619; U.S. Pat. No. 9,737,296, filed Apr. 18, 2017.
U.S. Appl. No. 15/638,412; U.S. Pat. No. 9,962,152, filed Jun. 30, 2017.
U.S. Appl. No. 15/640,436; U.S. Pat. No. 9,943,307, filed Jun. 30, 2017.
U.S. Appl. No. 15/640,442; U.S. Pat. No. 9,943,308, filed Jun. 30, 2017.
U.S. Appl. No. 15/667,459; U.S. Pat. No. 9,936,945, filed Aug. 2, 2017.
U.S. Appl. No. 15/794,572; U.S. Pat. No. 10,045,774, filed Oct. 26, 2017.
U.S. Appl. No. 15/942,515; U.S. Pat. No. 10,792,032, filed Mar. 31, 2018.
U.S. Appl. No. 11/231,135; U.S. Pat. No. 7,862,572, filed Sep. 20, 2005.
U.S. Appl. No. 11/982,174 (abandoned), filed Nov. 1, 2007.
U.S. Appl. No. 12/592,174; U.S. Pat. No. 8,123,762, filed Nov. 20, 2009.
U.S. Appl. No. 13/361,444; U.S. Pat. No. 8,821,519, filed Jan. 30, 2012.
U.S. Appl. No. 14/472,090; U.S. Pat. No. 9,451,948, filed Aug. 28, 2014.
U.S. Appl. No. 14/796,642; U.S. Pat. No. 9,474,523, filed Jul. 10, 2015.
U.S. Appl. No. 15/265,650; U.S. Pat. No. 9,597,071, filed Sep. 14, 2016.
U.S. Appl. No. 15/357,375; U.S. Pat. No. 9,700,301, filed Nov. 21, 2016.
U.S. Appl. No. 15/357,533; U.S. Pat. No. 9,700,302, filed Nov. 21, 2016.
U.S. Appl. No. 15/358,210; U.S. Pat. No. 9,642,613, filed Nov. 22, 2016.
U.S. Appl. No. 15/377,502; U.S. Pat. No. 9,642,614, filed Dec. 13, 2016.
U.S. Appl. No. 15/480,561; U.S. Pat. No. 9,795,376, filed Apr. 6, 2017.
U.S. Appl. No. 15/480,915; U.S. Pat. No. 9,795,377, filed Apr. 6, 2017.
U.S. Appl. No. 15/480,933; U.S. Pat. No. 9,808,238, filed Apr. 6, 2017.
U.S. Appl. No. 15/480,945; U.S. Pat. No. 9,936,944, filed Apr. 6, 2017.
U.S. Appl. No. 15/640,452; U.S. Pat. No. 9,962,153, filed Jun. 30, 2017.
U.S. Appl. No. 15/661,924; U.S. Pat. No. 9,962,154, filed Jul. 27, 2017.
U.S. Appl. No. 15/671,450; U.S. Pat. No. 9,962,155, filed Aug. 8, 2017.
U.S. Appl. No. 15/885,509; U.S. Pat. No. 10,111,654, filed Jan. 31, 2018.

(56) References Cited

OTHER PUBLICATIONS

U.S. Appl. No. 16/051,027; U.S. Pat. No. 11,253,249, filed Jul. 31, 2018.
U.S. Appl. No. 16/905,758; U.S. Pat. No. 11,172,922, filed Jun. 18, 2020.
U.S. Appl. No. 17/576,338 (pending), filed Jan. 14, 2022.
U.S. Appl. No. 12/218,633; U.S. Pat. No. 8,469,973, filed Jul. 17, 2008.
U.S. Appl. No. 13/900,991 (abandoned), filed May 23, 2013.
U.S. Appl. No. 15/256,079; U.S. Pat. No. 9,962,152, filed Sep. 2, 2016.
U.S. Appl. No. 15/656,655; U.S. Pat. No. 9,986,997, filed Jul. 21, 2016.
U.S. Appl. No. 15/828,171 (abandoned), filed Nov. 30, 2017.
U.S. Appl. No. 15/828,398; U.S. Pat. No. 10,307,155, filed Nov. 30, 2017.
U.S. Appl. No. 15/828,422; U.S. Pat. No. 11,033,262, filed Nov. 30, 2017.
U.S. Appl. No. 15/857,618; U.S. Pat. No. 10,383,622, filed Dec. 29, 2017.
U.S. Appl. No. 17/344,563 (pending), filed Jun. 10, 2021.
U.S. Appl. No. 12/175,442; U.S. Pat. No. 7,976,555, filed Jul. 17, 2008.
U.S. Appl. No. 15/828,431; U.S. Pat. No. 10,098,630, filed Nov. 30, 2017.
U.S. Appl. No. 12/909,606; U.S. Pat. No. 7,993,354, filed Oct. 21, 2010.
U.S. Appl. No. 13/204,820; U.S. Pat. No. 9,775,600, filed Aug. 8, 2011.
U.S. Appl. No. 13/205,056 (abandoned), filed Aug. 8, 2011.
U.S. Appl. No. 15/377,562; U.S. Pat. No. 9,675,339, filed Dec. 13, 2016.
U.S. Appl. No. 15/610,277; U.S. Pat. No. 9,962,151, filed May 31, 2017.
U.S. Appl. No. 15/942,509; U.S. Pat. No. 10,792,031, filed Mar. 31, 2018.
U.S. Appl. No. 16/236,966; U.S. Pat. No. 10,881,392, filed Dec. 31, 2018.
U.S. Appl. No. 17/100,922 (pending), filed Nov. 22, 2020.
U.S. Appl. No. 15/720,853 (abanoned), filed Sep. 29, 2017.
U.S. Appl. No. 16/384,640; U.S. Pat. No. 11,253,250, filed Apr. 15, 2019.
U.S. Appl. No. 17/567,138 (pending), filed Jan. 2, 2022.
U.S. Appl. No. 15/661,463; U.S. Pat. No. 10,292,698, filed Jul. 27, 2017.
U.S. Appl. No. 16/289,685; U.S. Pat. No. 11,039,829, filed Mar. 21, 2019.
U.S. Appl. No. 17/833,845 (pending), filed Jun. 6, 2022.

* cited by examiner

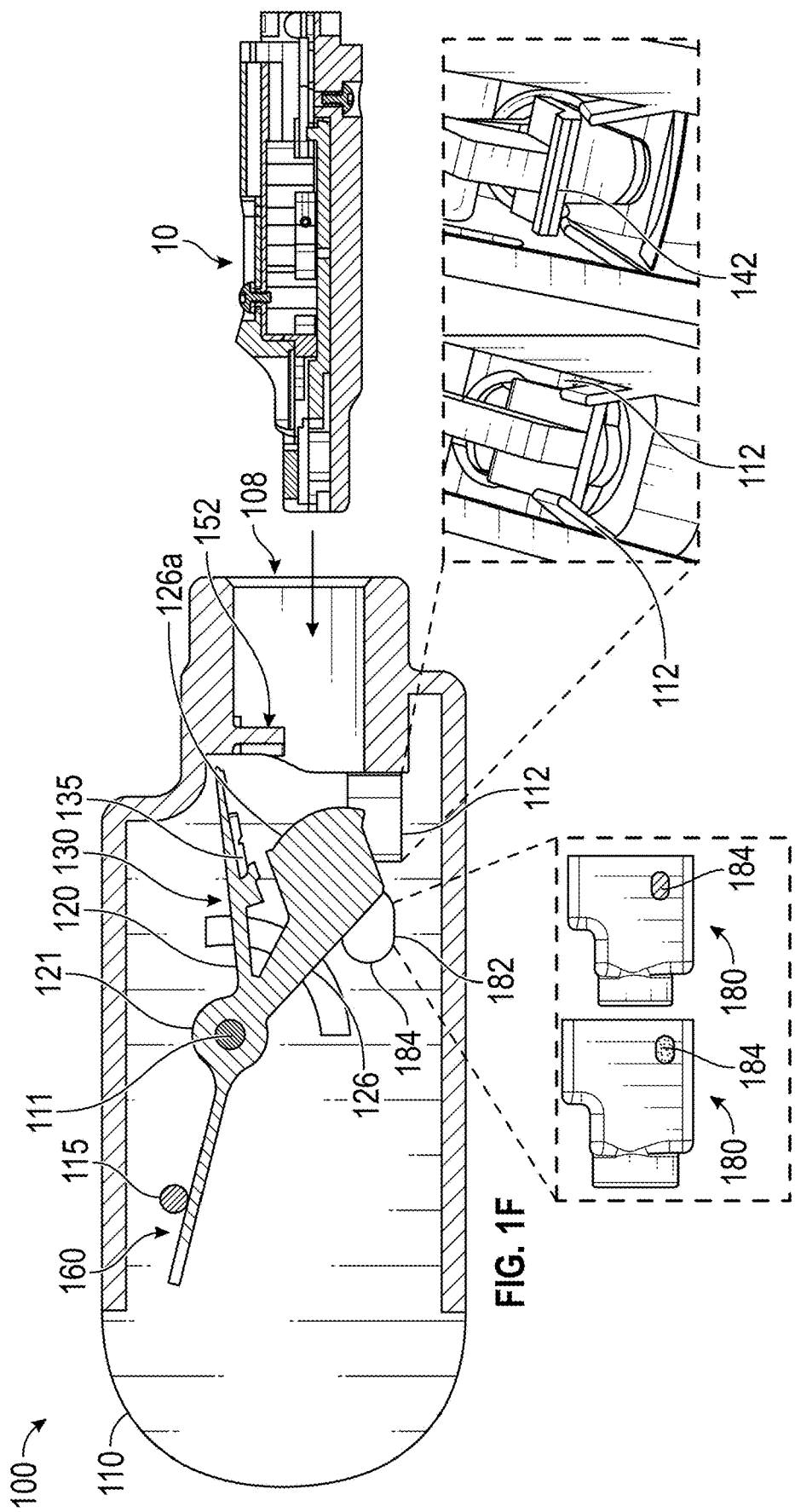

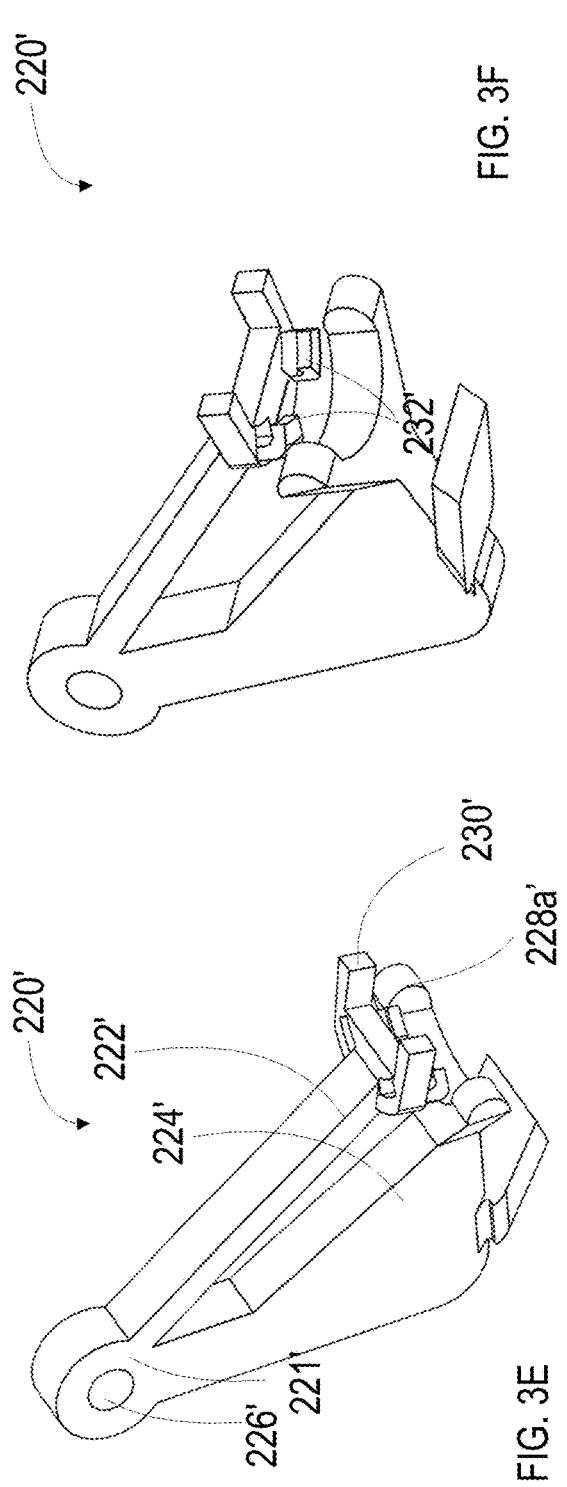
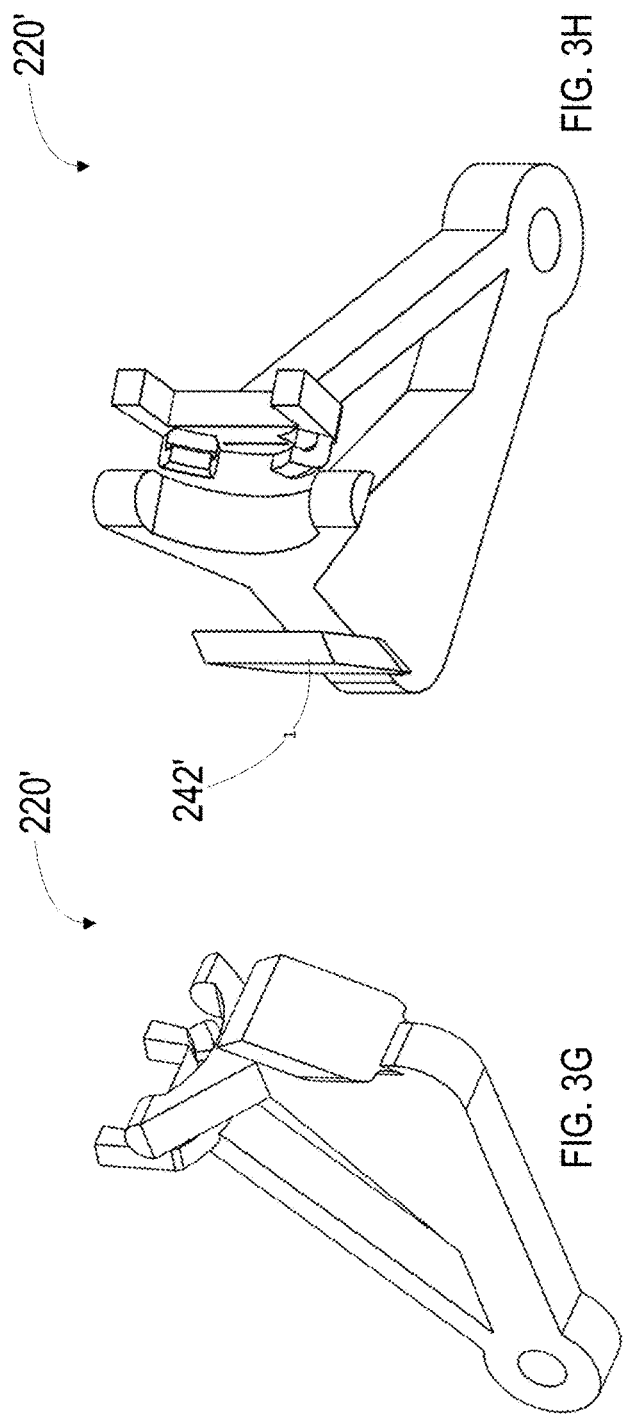

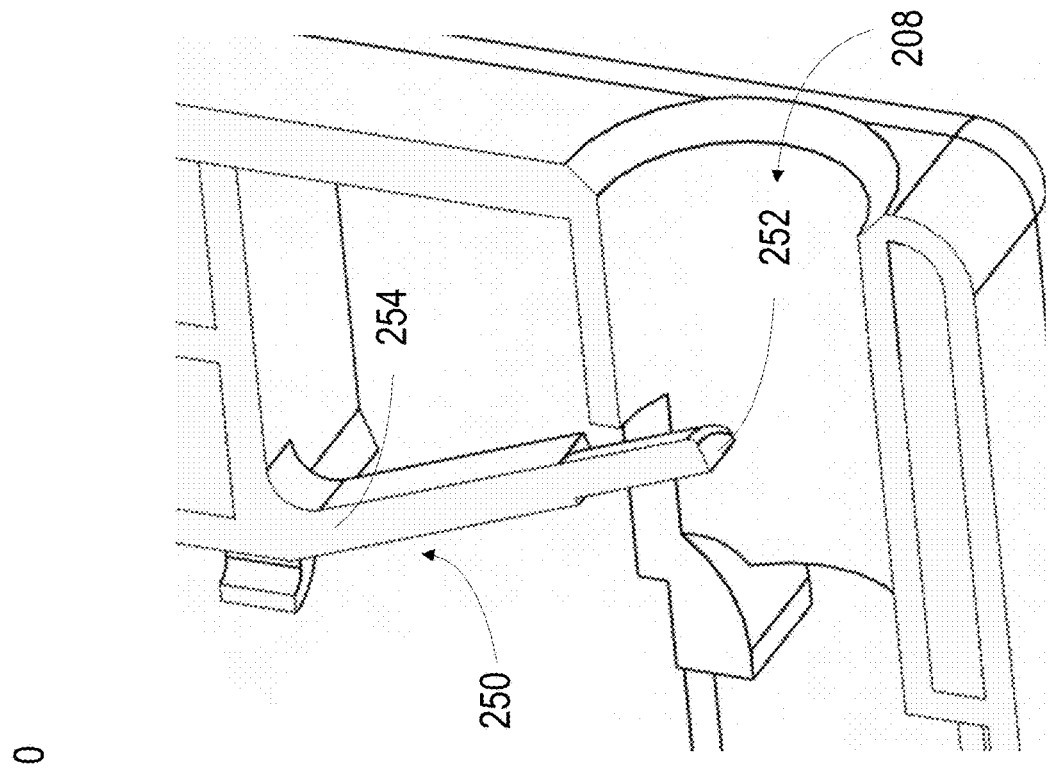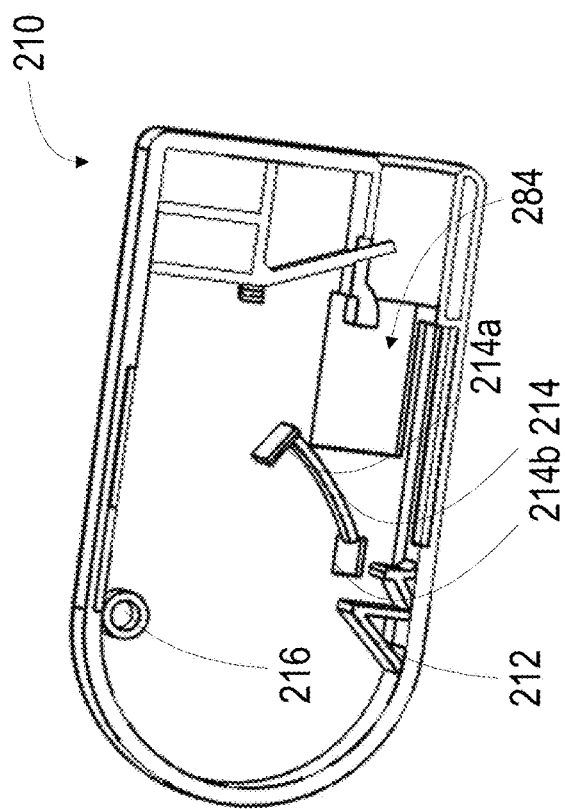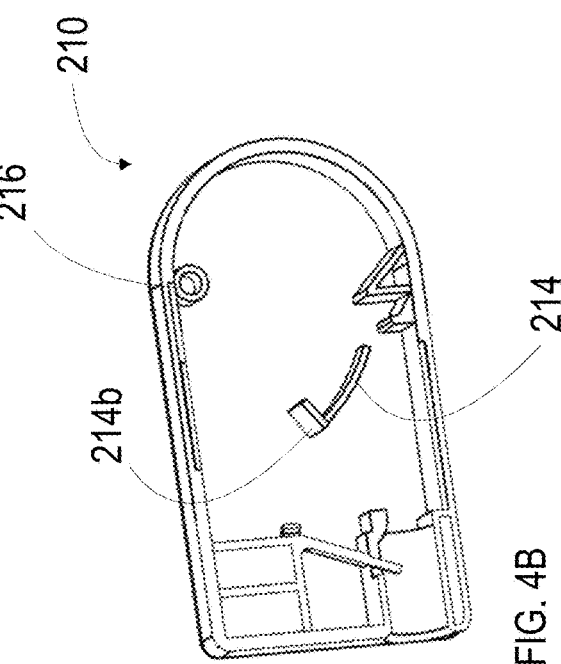

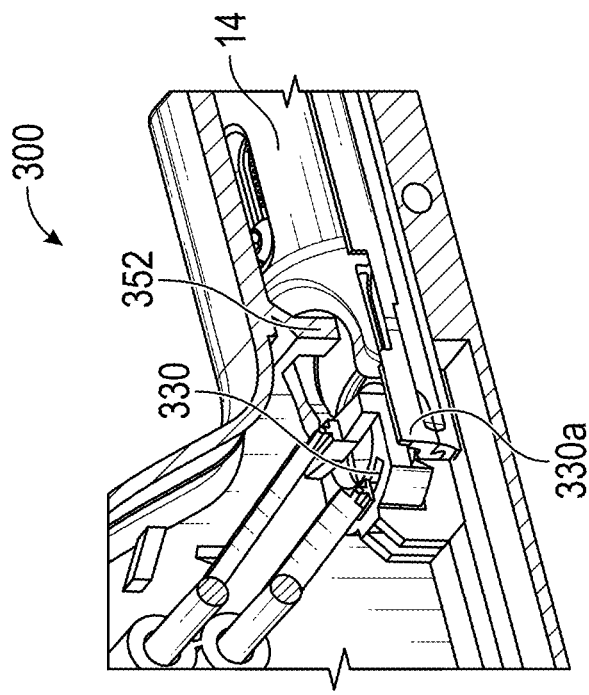
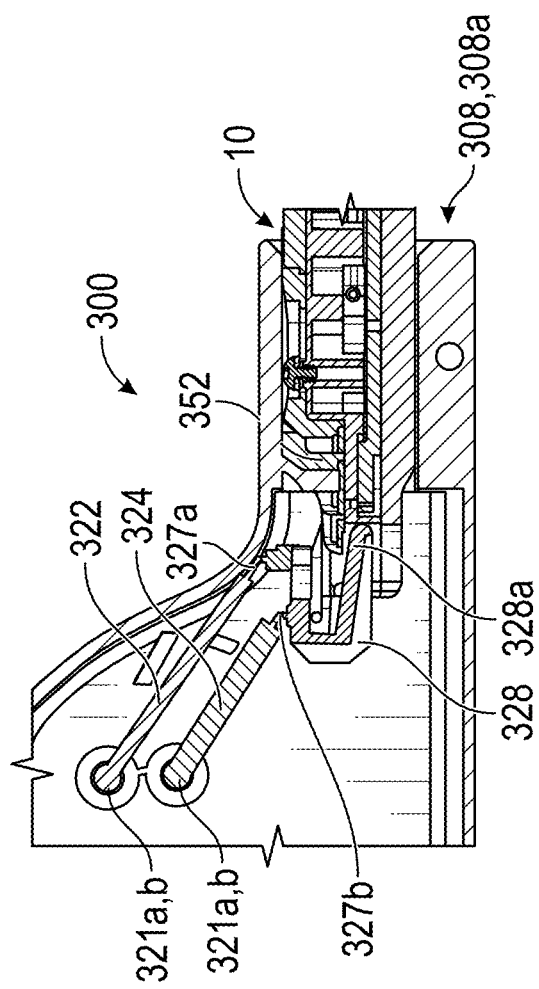
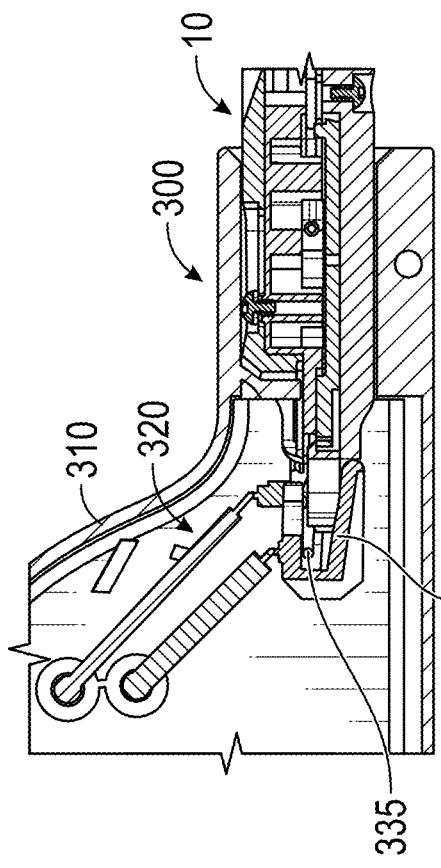
FIG. 5C
FIG. 5A
FIG. 5B

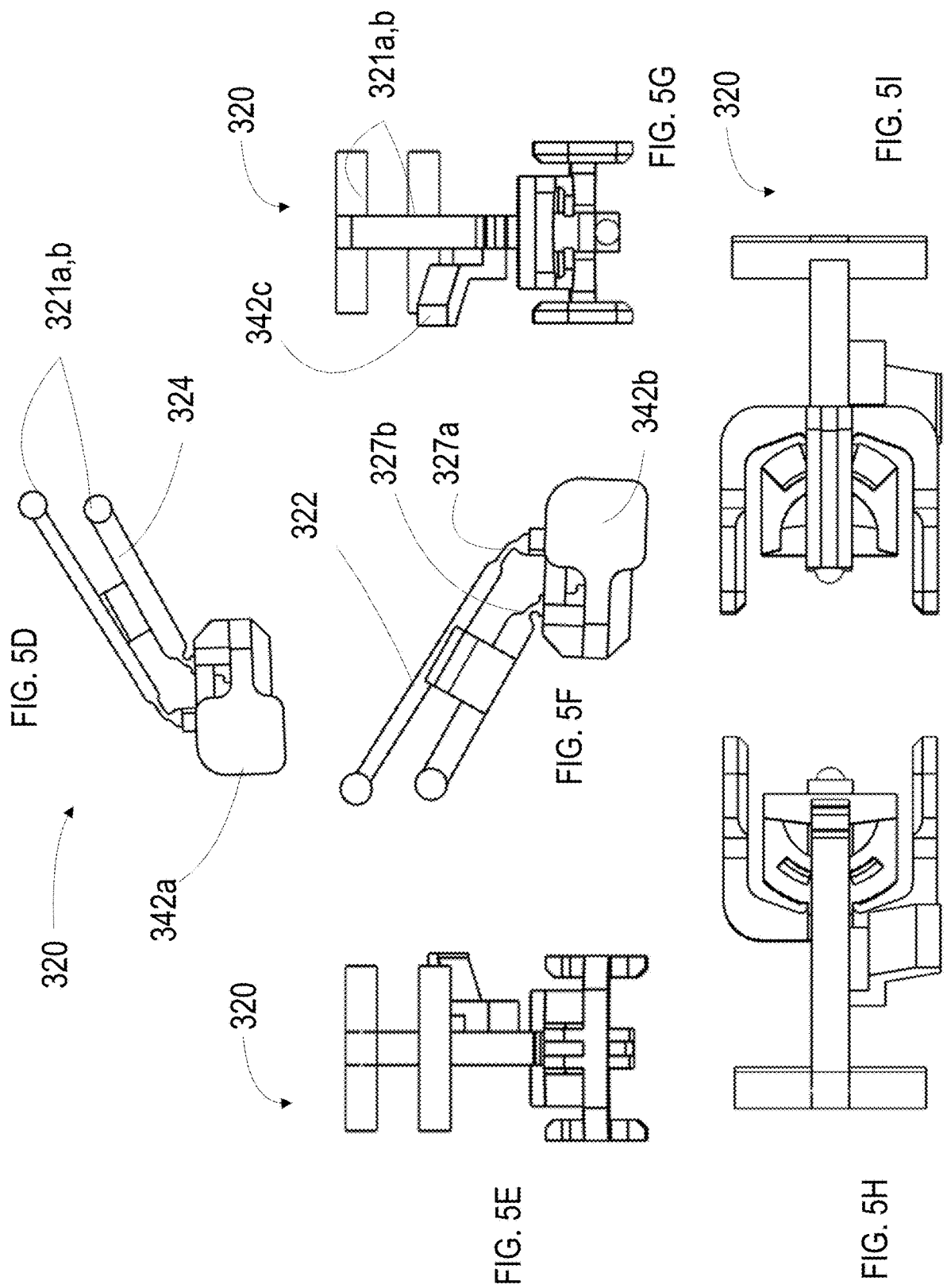

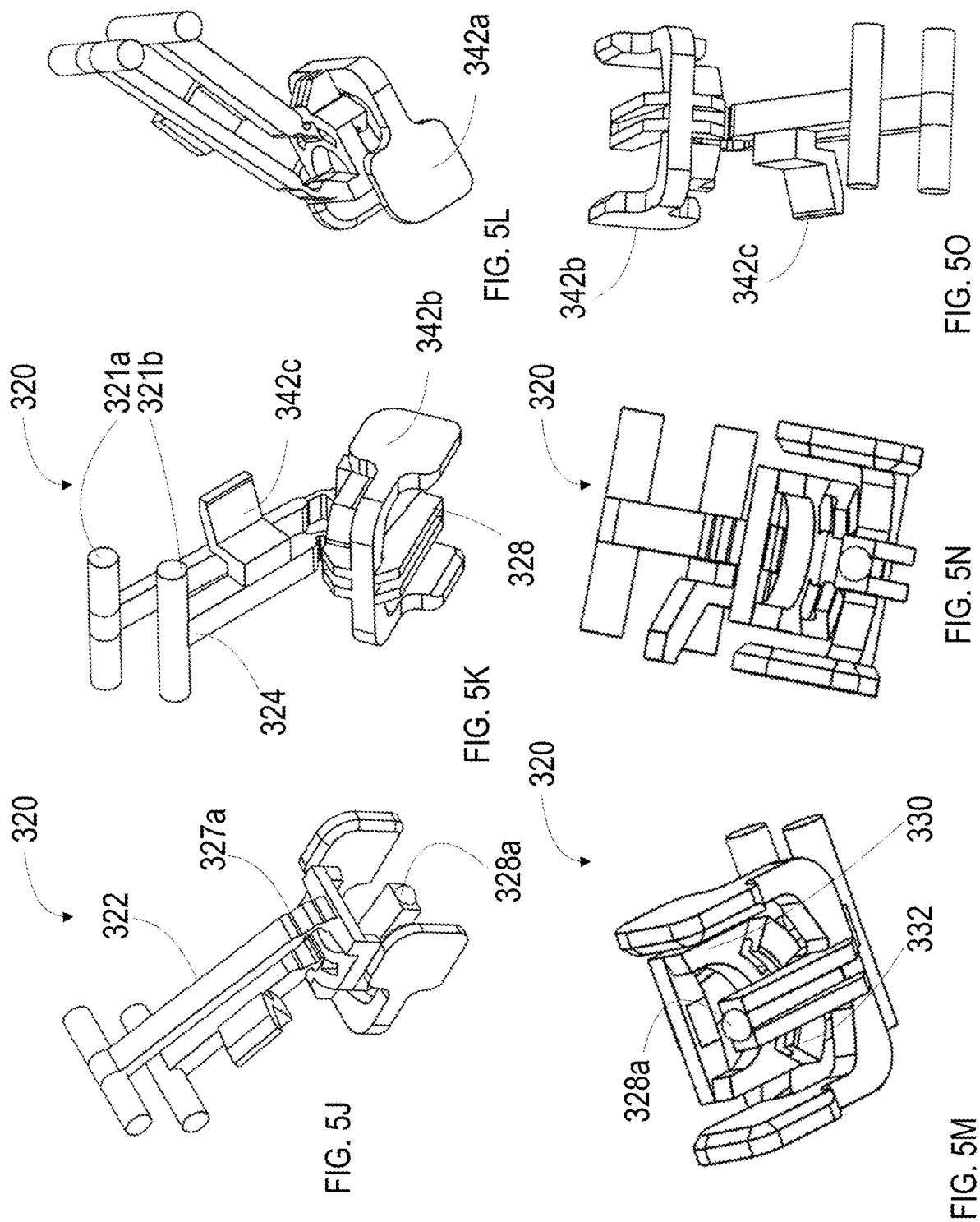

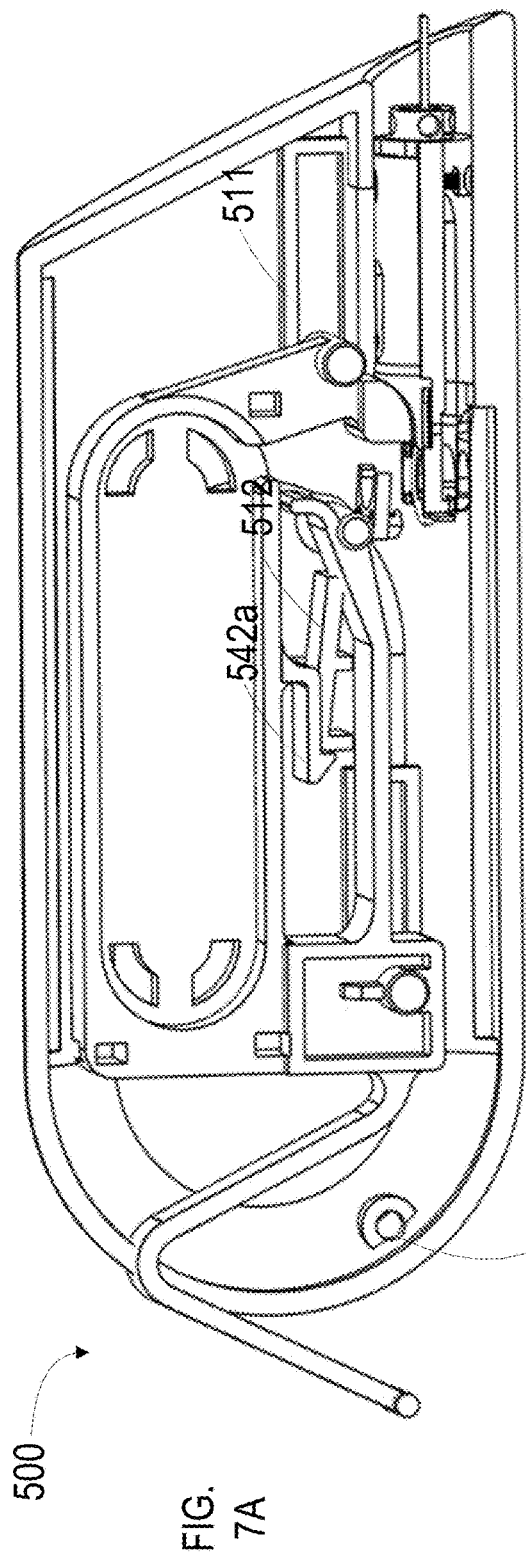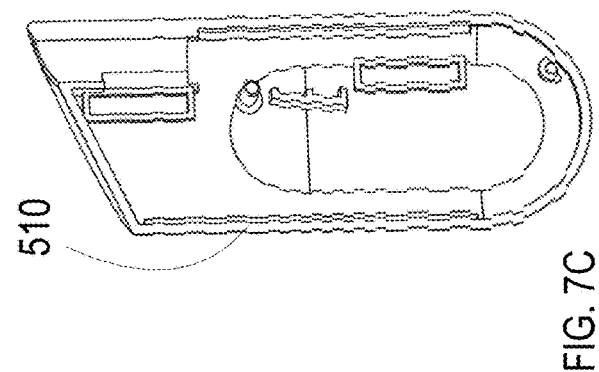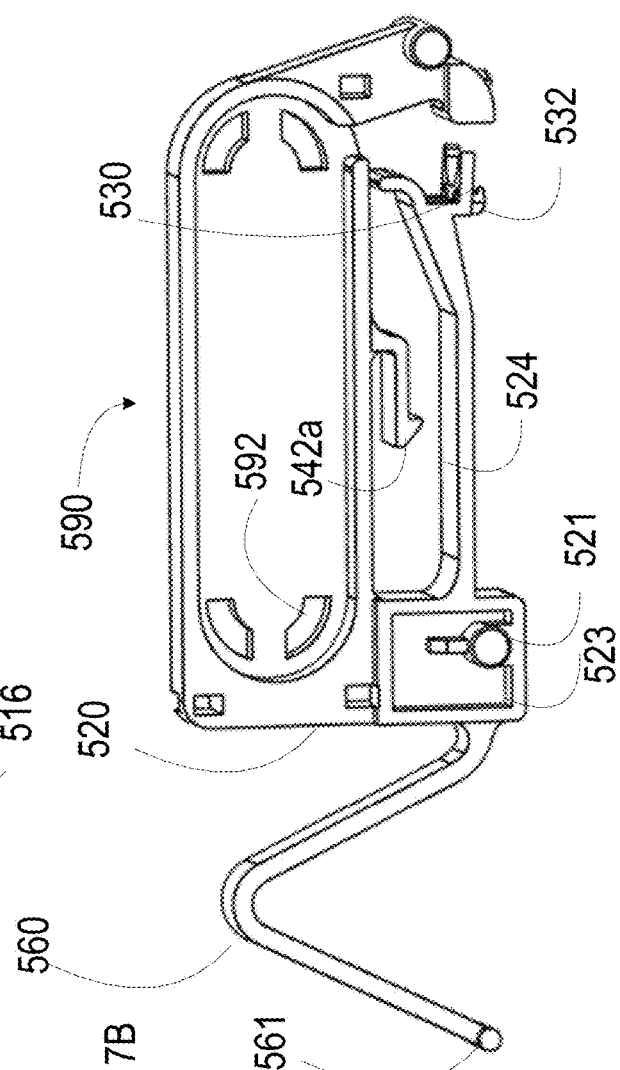

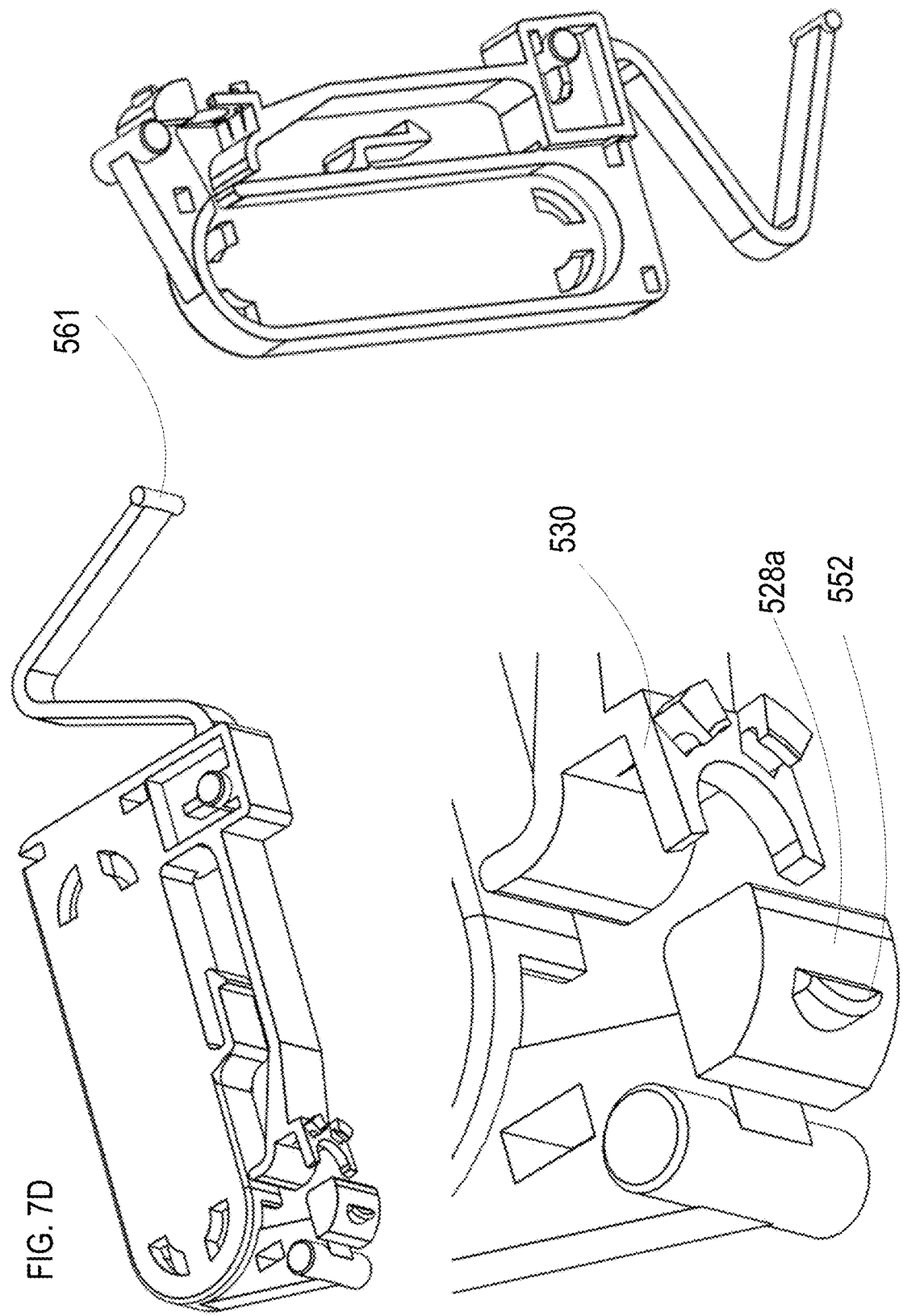

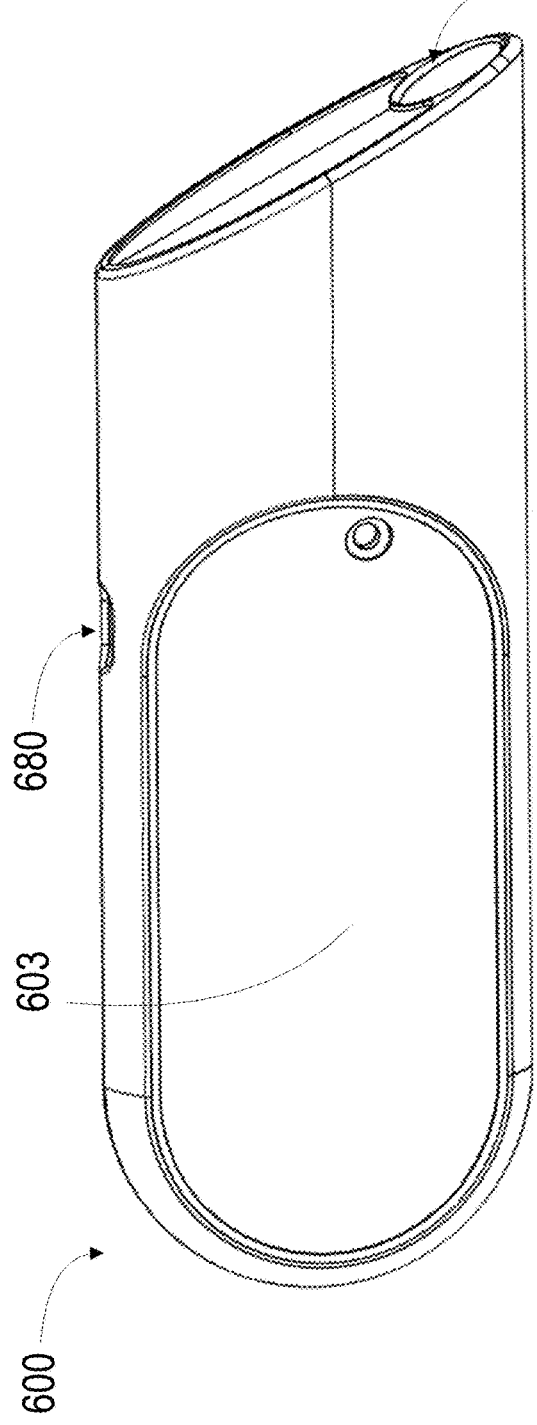
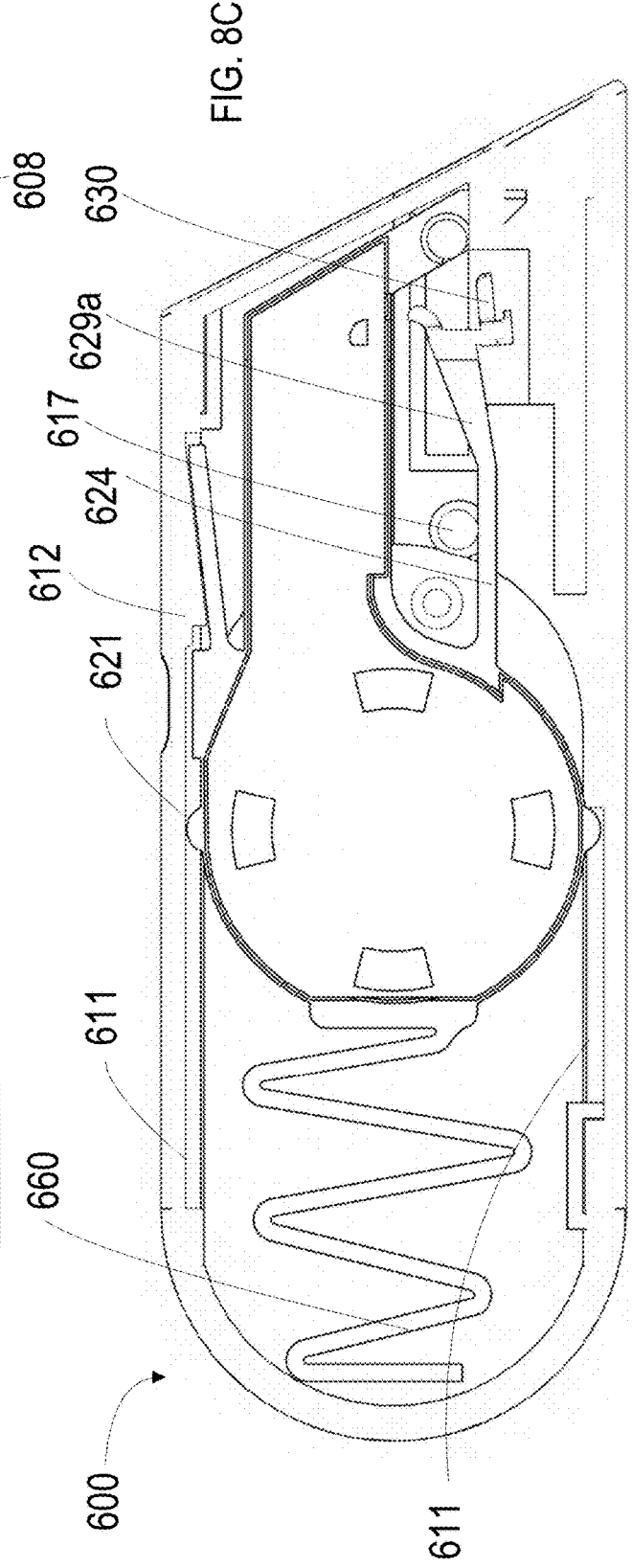

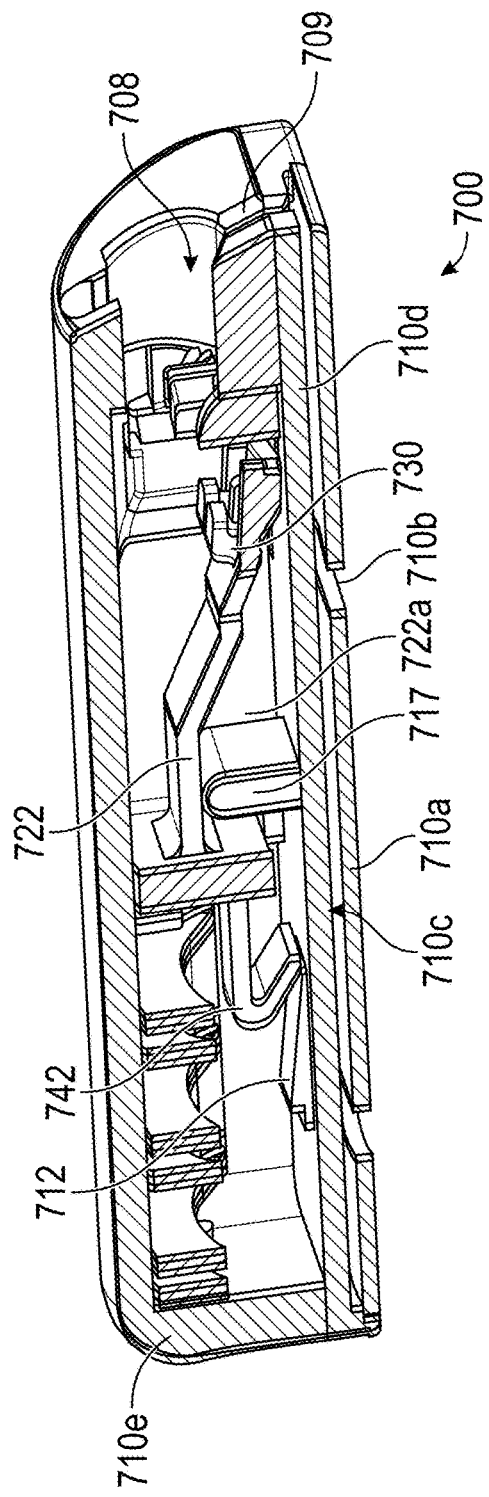
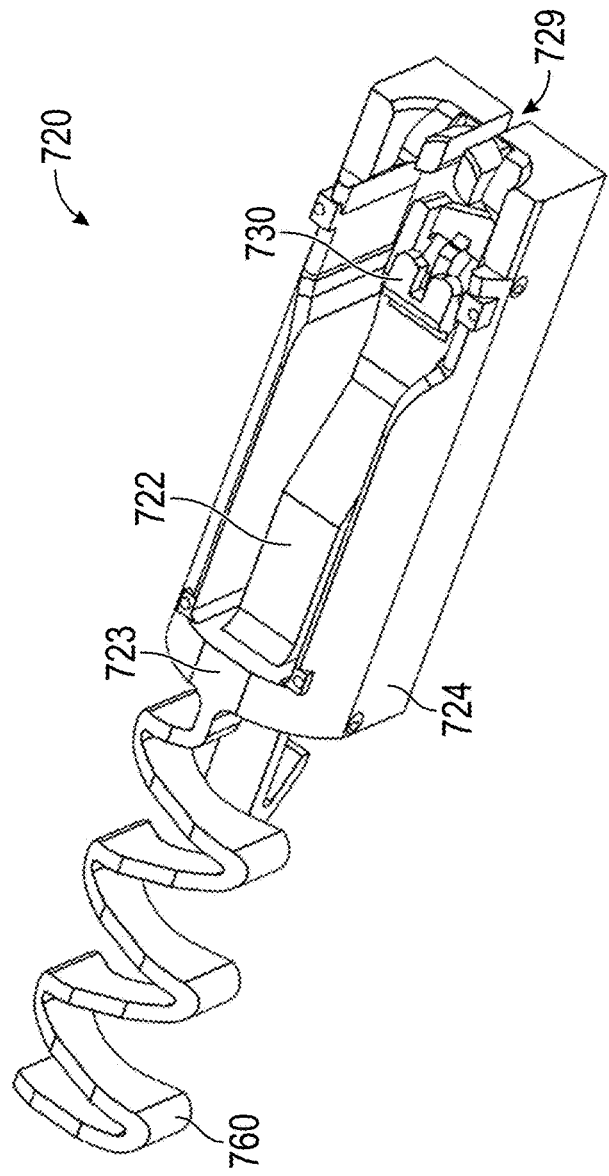
FIG. 9C
FIG. 9D

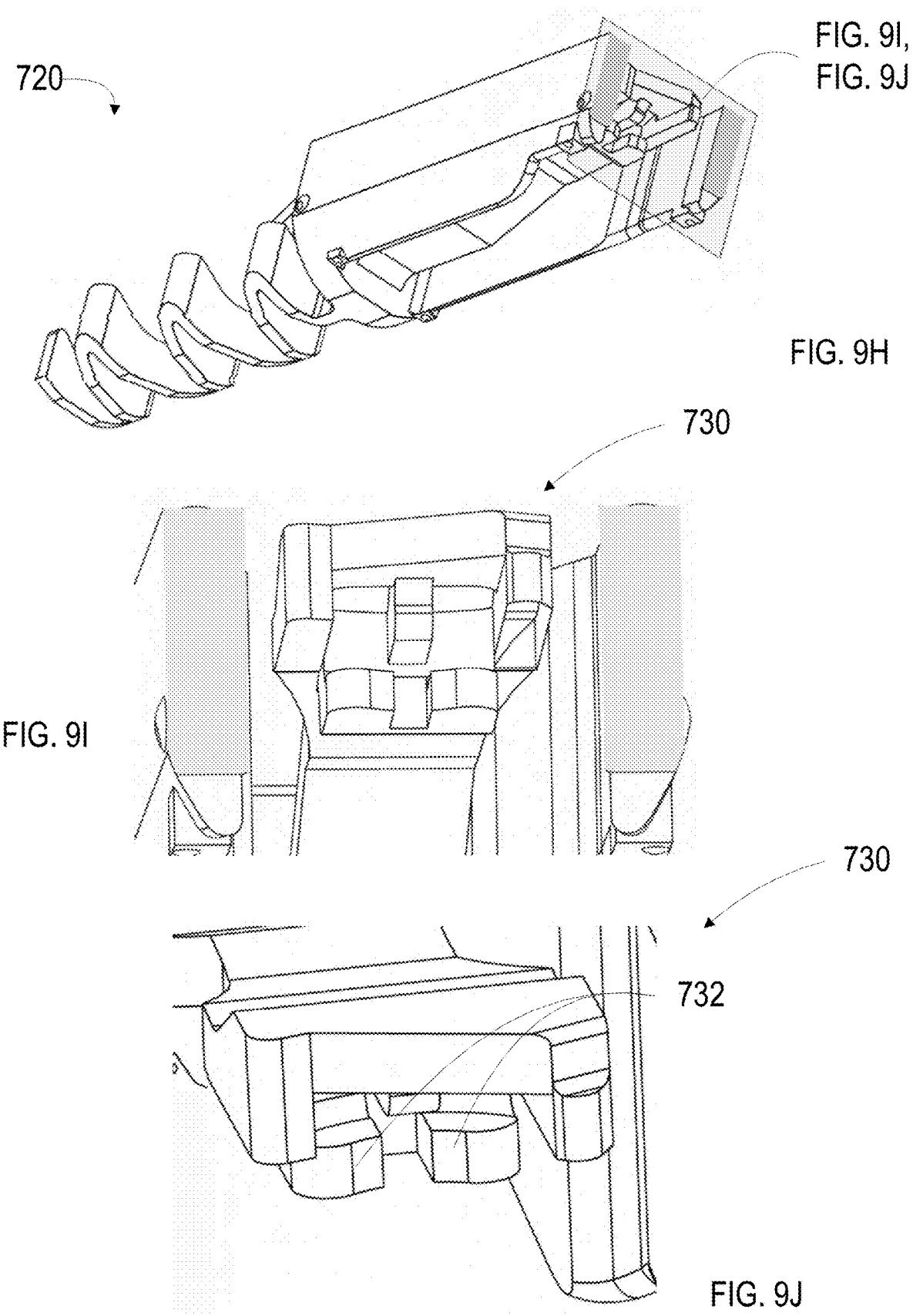

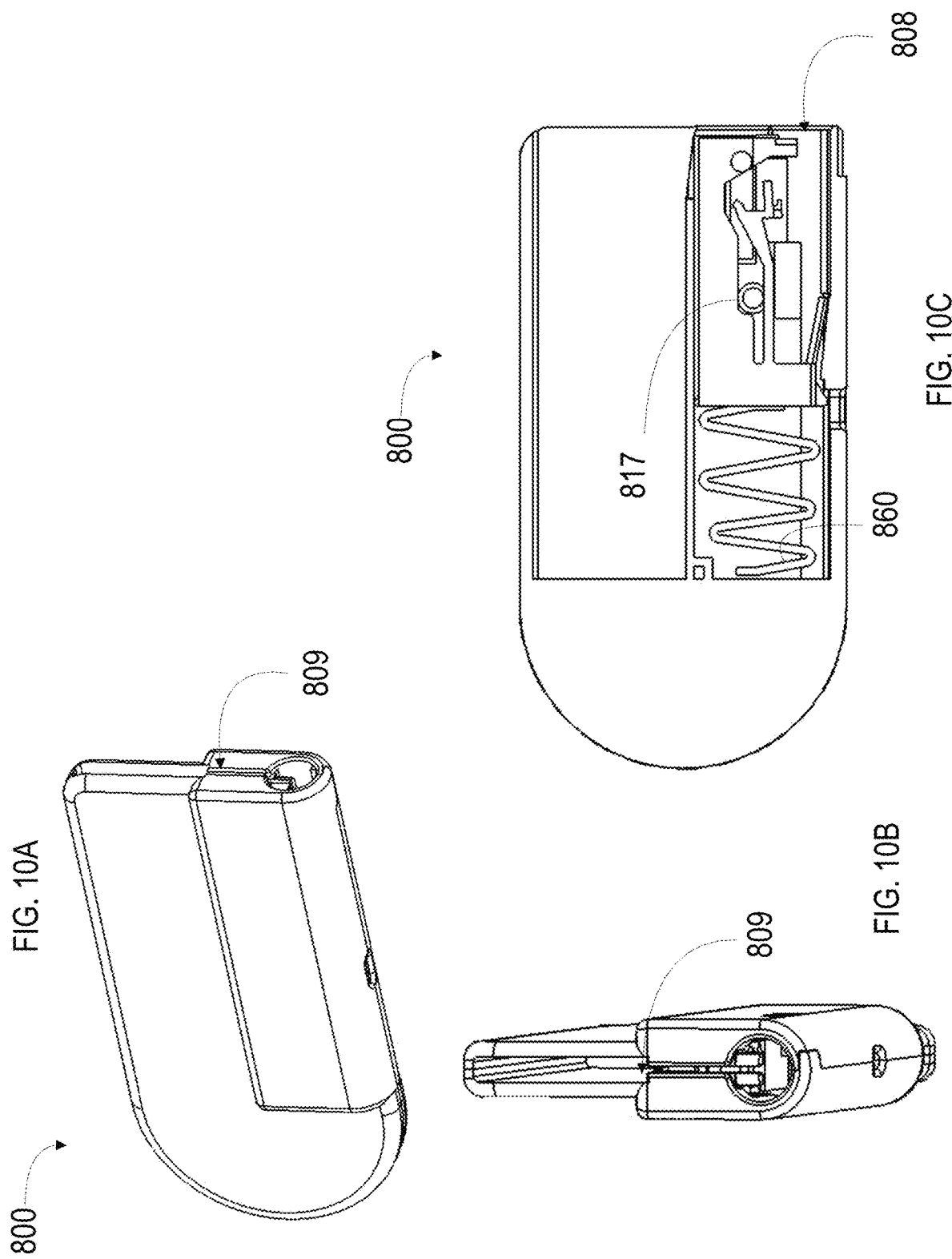

NEEDLE LOADER DEVICES AND RELATED SYSTEMS AND METHODS

CROSS-REFERENCE TO RELATED APPLICATIONS

The present patent application claims the benefit of priority to U.S. Provisional Patent Application No. 63/197,786, filed Jun. 7, 2021. The content of the aforementioned patent application is incorporated by reference herein in its entirety for all purposes.

TECHNICAL FIELD

Aspects of the present disclosure relate to devices, systems, and methods for performing a suturing procedure. For example, aspects of the present disclosure relate to needle loader devices including, but not limited to, for example, devices configured to receive a suturing device to load a suturing needle therein in support of remote surgical, diagnostic, therapeutic, and other treatment procedures. Further aspects of the disclosure relate to methods of operating such devices.

INTRODUCTION

Sutures are used in a variety of surgical and other applications, such as closing ruptured or incised tissue, soft tissue attachment, attachment of grafts, etc. Additionally, sutures may have other medical and/or non-medical uses. Conventionally, suturing is accomplished by penetrating tissue with the sharpened tip of a suturing needle that has a thread of suturing material attached to the opposite blunt end of the needle. The needle is then pulled through the tissue, causing the attached thread of suturing material to follow the path of the needle. Typically, a knot is tied at the trailing end of the thread to anchor the first stitch. This action is performed repetitively with application of tension to the needle to pull a length of the thread through the tissue using subsequent stitches until the tissue is sutured as desired with one or more stitches.

While the above-described suturing process can be performed manually, automated suturing systems also exist. Such systems can include a needle driver device that has an open, C-shaped portion into which tissue segments are introduced. The C-shaped portion defines two arms, each with an entry/exit point for a curved needle. The curved needle is driven around a track (generally following the C-shaped portion) and across the opening in the C-shaped portion to draw a thread of suturing material into the needle driver device through the tissue segments, similar to the manual suturing process discussed above. It is desirable to provide needle driver devices that occupy a minimal amount of space relative to a size (e.g., gauge and/or radius) of the needle. Such tools are useful in space-limited applications, such as in the case of minimally invasive surgery, for example laparoscopic surgery including both manual and computer-assisted surgery.

A need exists to provide reliable devices and techniques to load a suturing needle into these types of devices. While some approaches have been proposed and used, there is considerable room for improvement to provide safe and reliable devices.

SUMMARY

Example embodiments of the present disclosure may solve one or more of the above-mentioned problems and/or may demonstrate one or more of the above-mentioned desirable features. Other features and/or advantages may become apparent from the description that follows.

In accordance with some aspects of the present disclosure, a needle loader is provided. The needle loader includes a housing, a movable arm or assembly disposed within the housing, and a needle mount, which can optionally be defined on the movable arm or be located nearby, to releasably attach to an arced suturing needle.

In accordance with at least another aspect of the present disclosure, a needle loader can be provided that additionally or alternatively includes an arced needle releasably attached to the needle mount. The needle can be held in place attached to the needle mount by way of an interference fit or other suitable technique.

In accordance with at least another aspect of the present disclosure, a needle loader can be provided wherein the needle mount is defined on a surface of the movable arm that faces an arced needle track of a suturing device when loading an arced suturing needle in the needle track of the suturing device.

In accordance with further aspects of the present disclosure, a needle loader can be provided wherein the needle loader is configured to removably engage with a distal portion of a suturing device, wherein the suturing device typically includes an arced needle track.

In accordance with further aspects of the present disclosure, a needle loader can be provided wherein a movable arm is movable from a first position wherein the needle mount is spaced apart from a distal portion of the suturing device to a second position wherein the needle mount is adjacent an arced needle track of the suturing device. In some implementations, the movable arm can deform or flex as the needle mount approaches the second position. For example, the movable arm can flex against a distal portion of a suturing device as the needle mount approaches the second position.

In accordance with another aspect of the present disclosure, a needle loader can be provided wherein a needle mount of the needle loader includes one or more inclined surfaces that cause an arced needle mounted on the needle mount to approach a distal portion of a suturing device as the needle mount moves from a first position wherein the needle mount is spaced apart from the distal portion of the suturing device to a second position wherein the needle mount is adjacent to an arced needle track of the suturing device. For example, if desired, the needle mount and/or inclined surface can be configured to permit the inclined surface to slide over a boss as the needle mount moves from the first position to the second position. This can cause an arced needle mounted on the needle mount to approach a distal portion of a suturing device.

In accordance with at least another aspect of the present disclosure, a needle loader can be provided wherein a needle mount or movable arm can lock in position after it has reached a second, or displaced position. For example, the needle mount or movable arm can lock in position after it has reached a second position by action of a locking element. A spring-loaded barb or pawl coupled to the movable arm can pass over a boss defined on the housing of the needle loader. In another implementation, the needle mount or movable arm can be locked in position after it has reached the second position by a surface defined on the movable arm passing over a pawl defined in the housing of the needle loader. In some implementations, the needle mount movable arm can define a locking surface thereon to engage a retention surface defined by the housing when the movable arm has reached the second position. The engagement of the locking surface and the retention surface can prevent the movable arm from returning to the first position.

In accordance with another aspect of the present disclosure, a needle loader can be provided that includes a spring that urges against motion of a movable arm as the movable arm moves from a first position to a second position. For example, such a spring can comprise a leaf spring, a compression spring or a tension spring. In some implementations, the movable arm can be coupled to the spring. In some implementations, the movable arm can include a first end coupled to a rotatable hub and a second free end including the needle mount. In some implementations, the spring can also be coupled to the rotatable hub. In some implementations, the spring can comprise a deflectable hinge. In some implementations, the spring can be integrally formed with the needle mount.

In accordance with still another aspect of the present disclosure, a needle loader can be provided having a movable arm that includes a cam surface that is configured to slide over a distal portion of a suturing device to be loaded with an arced suturing needle as the movable arm approaches the second position.

In accordance with yet another aspect of the present disclosure, a needle loader can be provided wherein movement of a movable arm of the needle loader from a first position to a second position can activate an indicator confirming that the movable arm has reached the second position. The indicator can confirm that the movable arm has reached the second position by emitting a sound, a tactile signal, and/or by displaying one or more visual indicia. The indicator can confirm that the movable arm has reached the second position by moving from a first indicator position to a second indicator position. The movable arm can include a boss that slides in a guide track formed into an inner surface of the housing.

In accordance with additional aspects of the present disclosure, a needle loader can be provided that comprises a protrusion that extends into a path of a suturing device to be loaded with a needle from the needle loader. The protrusion can cause an arced needle track of the suturing device to be exposed as the suturing device is advanced along the path.

In accordance with additional aspects of the present disclosure, a needle loader can be provided wherein a housing of the needle loader further defines an opening therein for receiving the suturing device. The opening can at least in part define the path to insert and load the needle into the suturing device.

In accordance with additional aspects of the present disclosure, a needle loader can be provided that can receive a suturing device that includes a retractable cover to cover the needle track. A boss, protrusion, or other feature can retract the retractable cover of the suturing device to expose an arced needle track or other feature to receive an arced suturing needle from the needle loader. In some implementations, the protrusion or other feature can be coupled to the needle mount. In other implementations, the protrusion can be coupled to the housing.

In accordance with additional aspects of the present disclosure, a needle loader can be provided having a slidable arm, or a movable arm that can be rotatable about at least one pivot point between a first position and a second position to load an arced needle into a suturing device. In some implementations, the movable arm can comprise a four-bar linkage. The four-bar linkage of the movable arm can be rotatable about two pivot points. In some implementations, the four-bar linkage can comprise two generally parallel pivotable arms, wherein each generally parallel pivotable arm includes a first end and a second end, and further wherein a respective first end of each of the parallel pivotable arms can be rotatably coupled to the housing. In some implementations, a respective second end of each of the parallel pivotable arms can be coupled to the needle mount by a hinge.

In accordance with additional aspects of the present disclosure, a needle loader can be provided that comprises a needle mount that in turn comprises a first surface defining a boss or retainer thereon to receive an arced needle. The needle mount can further include a second surface that faces the first surface of the needle mount. The first surface of the needle mount and the second surface of the needle mount can cooperate to define a gap to receive a distal portion of the suturing device. At least one of the first surface of the needle mount and the second surface of the needle mount can comprise a ramped surface to guide an arced needle track of a suturing device toward an arced needle mounted on the needle loader as the suturing device is advanced along a path of travel with respect to the needle loader.

In accordance with additional aspects of the present disclosure, a needle loader can be provided comprising a needle mount that can be slidably disposed within a housing. For example, a needle mount can be slidably movable from a first position wherein the needle mount is not engaged with a distal portion of a suturing device to a second position wherein the needle mount is engaged with the distal portion of the suturing device.

In accordance with additional aspects of the present disclosure, a needle loader can be provided that comprises a suture compartment to receive a length of suture coupled to an arced needle. The length of suture can be, for example, between about six and about 24 inches in length. In some implementations, the suture compartment can be coupled to a movable needle mount. If desired, the suture compartment can be integrally formed with the needle mount. In some implementations, the suture compartment can be configured to slide with or without the needle mount within the housing. If desired, the suture compartment can comprise at least one boss that is slidably received in a respective track formed into the housing. In some implementations, the suture compartment can be oblong in shape. In some implementations, the suture compartment can be defined by a peripheral curved wall. The peripheral curved wall is circular in shape, elliptical in shape, or a combination of different shapes. In some implementations, the suture compartment can be located in a first compartment defined by the housing that is distinct and at least partially separated from a second compartment that houses the movable arm. The first compartment and the second compartment can be joined by a groove, and a suture coupled to an arced suturing needle that is coupled to the needle mount disposed in the second compartment can extend through the groove to a predetermined length of suture in the first compartment.

In accordance with additional aspects of the present disclosure, the housing of the needle loader can define one or more gripping surfaces to facilitate gripping by a user to hold the needle loader.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are illustrative and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure and are incorporated in and constitute a part of this specification. The drawings illustrate one or more embodiments of the present teachings and together with the description explain certain principles and operation. In the drawings, FIGS. 1A-1H depict views of a needle loader device in accordance with some embodiments of the present disclosure, or aspects thereof.

FIGS. 5A-5O depict views of a needle loader device in accordance with some embodiments of the present disclosure, or aspects thereof.

FIGS. 8A-8C depict views of a needle loader device in accordance with some embodiments of the present disclosure, or aspects thereof.

FIG. 12 is a perspective view of a manipulator system according to an illustrative embodiment of the disclosure.

FIG. 13 is a partial schematic view of an embodiment of a manipulator system having a manipulator arm with two instruments in an installed position according to the present disclosure.

DETAILED DESCRIPTION

The present disclosure provides various embodiments of needle loader devices, systems, and methods. Needle loader devices according to various embodiments of the present disclosure include features that facilitate the loading of a suturing device with an arced suturing needle.

In accordance with some aspects of the present disclosure, a needle loader is provided. The needle loader includes a housing, a movable arm disposed within the housing, and a needle mount defined on the movable arm to releasably attach to an arced suturing needle.

For purposes of illustration, and not limitation, a representative implementation of a needle loader is presented in FIGS. 1A-1H. Further embodiments of needle loaders, or aspects thereof, are illustrated in FIGS. 2A-11F.

Figure 1A:
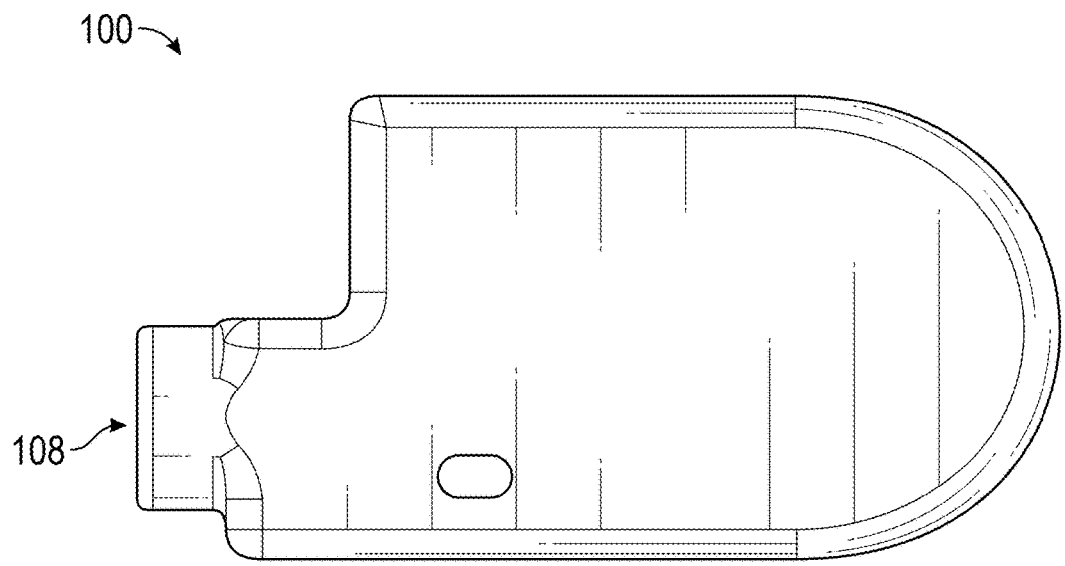
Figure 1B:
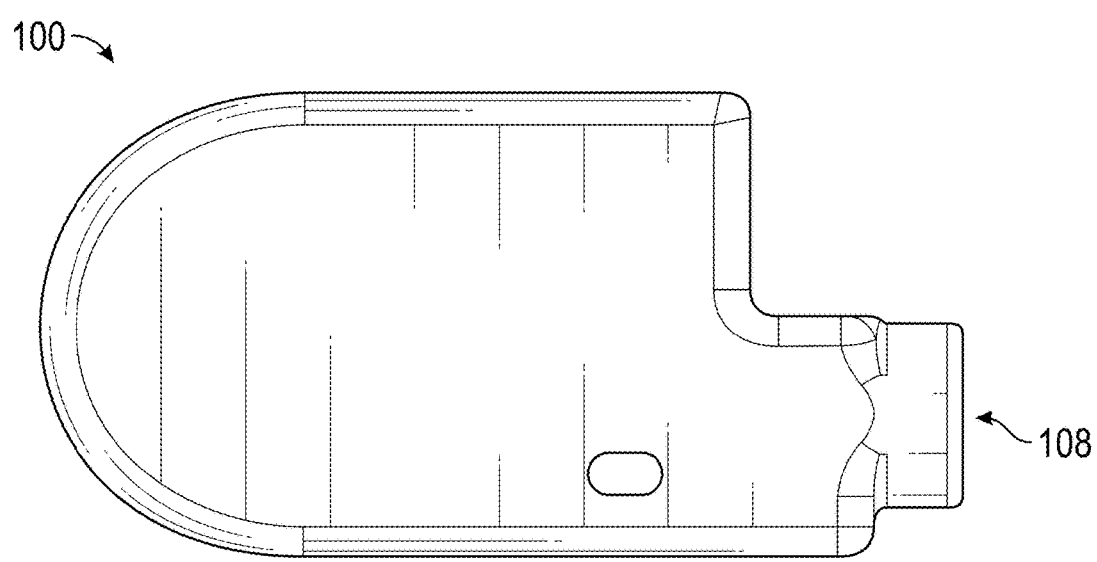
Figure 1C:
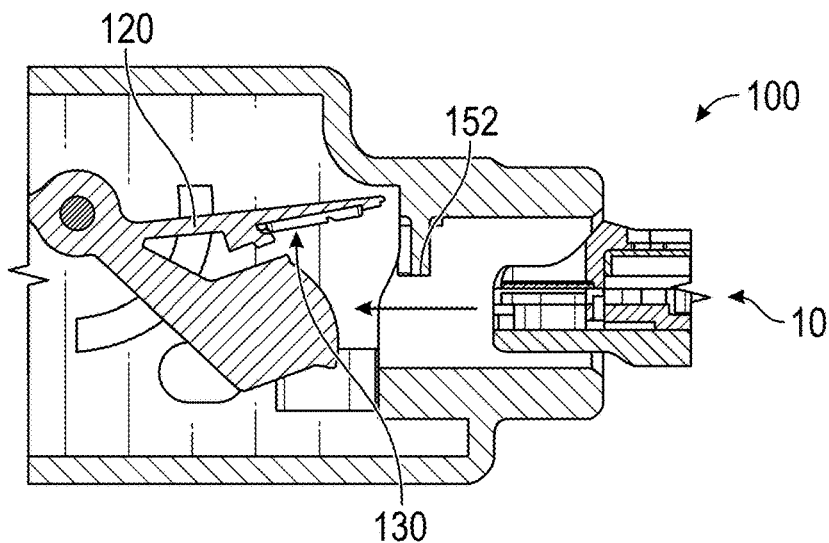
Figure 1D:
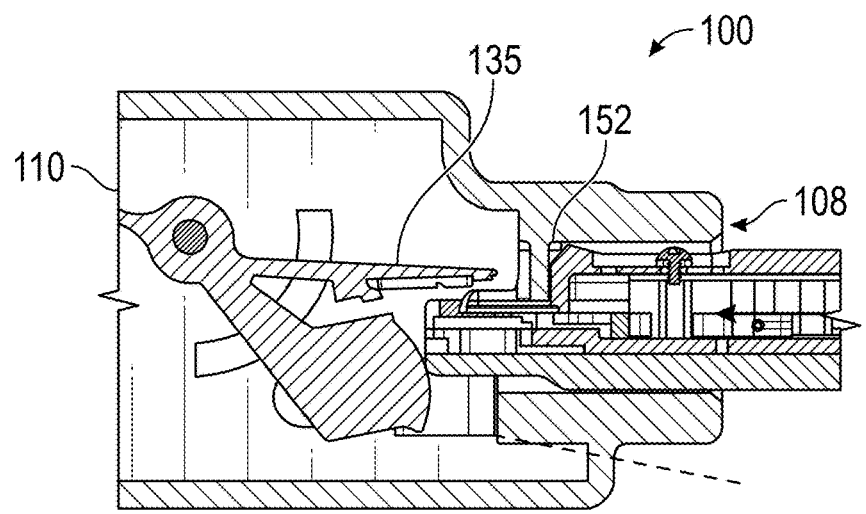
Figure 1E:
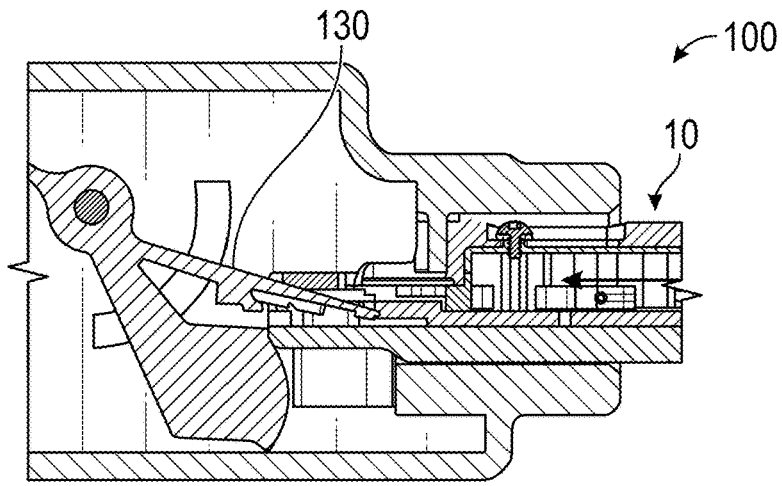

The needle loader 100 of FIGS. 1A-1H includes a housing 110, a movable arm 120 disposed within the housing 110, and a needle mount 130 defined on the movable arm 120 to releasably attach or releasably couple to an arced suturing needle 135. FIGS. 1A-1B illustrate a right-side elevational view and left side elevational view, respectively, of needle loader 100. FIGS. 1C-1E illustrate interior views of the needle loader 100. As described in further detail below, the housing 110 is configured to receive a portion of a suturing device 10 such that insertion of the suturing device 10 into the housing 110 causes the needle mount 130 to move from a first position to a second position and transfer (e.g., load) the suturing needle 135 into engagement with the suturing device 10.

Referencing FIG. 1F, with respect to embodiment 100, needle loading is accomplished by way of rotary motion of a movable arm, or arm assembly 120, about a boss or axle 111. Specifically, forward motion of a suturing device 10 into an opening 108 of a housing 110 of the device urges against a portion (e.g., 126a) of the arm or arm assembly 120 to cause the arm or arm assembly 120 to rotate clockwise (with regard to FIG. 1F) so that a mount 130 including the needle 135 mounted thereon moves from a first location wherein it is out of alignment with a path of travel of the suturing device 10 to a second location wherein the mount 130 and needle 135 engage with the suturing device 10, such that continued forward motion of the device 10 into passage 108 then causes the needle to align with and be pressed into an arcuate needle track of the suturing device so that the needle 135 becomes engaged with the needle track. Optionally, at the same time, the continued motion of the arm or arm assembly 120 about the boss or axle 111 can cause a lock 142 to engage, to prevent backward rotation, or movement of the arm or arm assembly 120 about the boss or axle 111. As such, once this engagement has occurred, the needle 135 is trapped by the needle track of the suturing device 10, and the device can be withdrawn.

It will be appreciated that a number of the embodiments disclosed herein provide a tunnel or passageway (e.g., 108) into which a suturing device 10 is inserted. This passageway, in cooperation with the supporting housing (e.g., 110), act to isolate the needle 135 from a user that is loading the needle onto the suturing device 10 during the loading process. And, optionally, the needle loader 100 can be further configured to permit the suturing device 10 to close over the needle track containing the needle 135 as the suturing device 10 is withdrawn from the needle loader, still further isolating the needle from inadvertent contact. Furthermore, the needle mount 130 holds the needle 135 in the needle loader 100, and mounts the needle 135 to the suturing device 10 in an orientation whereby the sharp end and the second end of the needle 135 are wholly contained within the needle track of the suturing device such that, when the suturing device 10 is extracted from the needle loader 100, only the middle of the body of the needle 135 is exposed in the gap of the suturing device 10. In some embodiments, optionally, each end of the needle may be fully covered and surrounded by the needle track and sliding cover of the suturing device 10. The needle can then be advanced to a starting position within the suturing device 10 by cycling the drive system to advance the needle to a relative position within the needle track of the suturing device 10 wherein the entire needle, including both ends, is situated within the suturing device and the sharp leading end of the suturing device is protected so that it will prevent accidental needle contact.

It will be appreciated that the needle loader 100 containing the needle 135 with suture material coupled thereto can be provided in a sterile kit surrounded by a removable envelope and/or container that is ready to be opened upon use in a procedure. The kit may be a single use device, or may be reprocessed and reloaded with a new/sterilized needle as desired.

The arced needle 135 can be releasably held in place attached to the needle mount 130 by way of an interference fit. The needle mount 130 may include needle engagement portions configured to releasably hold the surface of the arced needle 135. For example, a flexible member, such as one or more cleats, clips or fingers that can flex and release the needle after delivery can be used. Other suitable techniques can be used, such as a magnetic needle mount 130 with a ferritic needle 135. Alternatively, a deformable material can be provided as a part of the needle mount 130, or a relatively high friction or tacky surface. It will be appreciated that these techniques can be used to hold a needle in place in the other implementations described herein.

As depicted, the needle mount 130 is defined on a surface of the movable arm 120 that faces an arced needle track of a suturing device 10 when loading an arced suturing needle 135 in an arcuately shaped needle track of the suturing device 10. An example of a suturing device suitable for being loaded by needle loader 100 can include, for example, those described in U.S. Pat. No. 7,862,572, which is incorporated by reference herein in its entirety for all purposes.

As depicted, the arm 120 is pivotally mounted to the housing 110. In the illustrated embodiment, the arm 120 is mounted to a hub 121 defining a passage therethrough that is rotatably received on a boss or axle 111 defined by the housing 110. As such, the movable arm 120 includes a first end coupled to the rotatable hub 121 and a second free end coupled to the needle mount 130, which in turn releasably holds the needle 135.

As depicted in FIG. 1F, in some embodiments, a spring, such as a leaf spring 160, may extend outwardly from the hub 121. The spring 160 is deflectable and can bend. In operation, a lower arm, or boom 126 extends downwardly from the hub 121 (e.g., relative to the position of the arm 120), and defines a cam surface 126a thereon.

As mentioned above, to load the needle 135 into the suturing instrument 10, the suturing instrument 10 is inserted into a cavity, or opening, 108 of the needle loader 100, and the distal end or end region of the suturing device 10 urges against the cam surface 126a of the boom 126. This causes the hub 121 including arm 122 and needle mount 130 with needle 135 to rotate in a clockwise direction (relative to the orientation shown in FIGS. 1C-1E), resulting in the needle 135 being caused to approach the distal end region of the suturing device 10. As this is occurring, the leaf spring 160 contacts and begins to flex against boss 115 defined by the housing 110 to provide a countervailing force that resists the forward insertion movement of the suturing device 10 into the housing 110. In so doing, the spring 160 urges against motion of the movable arm 120 as the movable arm 120 moves from a first position to a second position.

In the event that the movable arm 120 does not move entirely to its second position, such as when the user only partially inserts the suturing device 10 but does not load the needle into the suturing device 10, the spring 160 also functions as a way for the needle loader 100 to reset itself to the first position. This feature is also set forth in the other embodiments herein.

It will be appreciated that the spring 160 can be configured in various manners. For example, the spring can comprise a leaf spring, a compression spring or a tension spring, among others. As illustrated in the needle loader 100, the movable arm 120 is integrally formed with the spring 160 in a single molding, but these components can be separated or provided as individual components. Likewise, in other implementations, one or more springs can be provided that are not coupled to a needle carrying component of the device.

As depicted in FIGS. 1C-1E, in operation the movable arm 120 of the needle loader 100 can be movable from a first position, such as that in FIG. 1C, wherein the needle mount 130, and needle 135 are spaced apart from the distal portion of the suturing device 10 to a second position, such as that in FIG. 1E, wherein the needle mount is adjacent the arced needle track of the suturing device 10. In the embodiment of FIGS. 1C-1E, the arm 120 of the needle loader 100, and/or the needle mount 130 of the needle loader 100, can be configured to bend, or flex, as the needle mount 130 with the needle 135 mounted thereon approaches the second position illustrated in FIG. 1E. Specifically, in the embodiment of FIG. 1E, the arm 120 can flex against the distal portion of the suturing device 10 as the needle mount 130 approaches the second position, while the leaf spring is also flexing against boss 115.

As further illustrated in FIGS. 1F and 1H, optionally, in some embodiments, the needle mount 130 and movable arm 120 are configured to lock in position after, or as, the needle 135 is loaded into the needle track of the suturing device 10. This can prevent the needle mount 130 and movable arm 120 from moving from the second position to the first position when, for example, the instrument 10 is removed from the needle loader 100. For example, a portion of the needle mount 130, movable arm 120, and/or spring 160 may include one or more locking surfaces configured to engage one or more retention surfaces of the housing 110 to prevent backwards movement of the assembly to the first position. These or similar locking surface features can also be included in the other embodiments of needle loaders discussed herein.

As illustrated in FIGS. 1F and 1H, a boss 142 may be provided on either side of the boom 126 to facilitate locking of the needle mount 130 during or after needle loading. The hub 121, arm 120, boom 126, and spring 160 form a movable assembly that may be locked in position by the bosses 142 engaging respective tabs, barbs, or pawls 112 formed into the housing 110. As the bosses 142 move relative to the tabs 112, the bosses 142 may deflect the tabs 112 out of the way, and the tabs 112 may then snap back in place after the bosses 142 pass the tabs 112, thereby preventing the assembly from rotating backward. At this point, the needle 135 is loaded into the suturing device 10 and the suturing device can be removed from the housing 110. In some implementations, the needle mount 130, movable arm 120, boom 126 and/or spring 160 can define additional or alternative locking surface thereon to engage one or more retention surfaces defined by the housing when the movable arm has reached the second position and the needle has been loaded into the suturing device 10. As will be appreciated by those of skill in the art, the engagement of the locking surface of the movable component and the retention surface of the housing (or vice-versa) can prevent the movable arm 120 from returning to the first position to ensure delivery of the needle 135 to the suturing device 10.

In accordance with a further aspect of the present disclosure, optionally, movement of the movable arm to the second position can activate an indicator confirming that the movable arm has reached the second position. This can indicate to a user that a needle loader 100 has been used and does not contain a sterile needle available for loading into a suturing device 10. For example, with reference to FIG. 1G, an indicator 180 is provided that is formed by the cooperative position of a window 182 and a portion of the movable assembly (e.g., 120) bearing visual indicia 184. For example, the boom 126 can include indicia formed on the side thereof, such as indicia of two different colors (e.g., green/red), or patterns (e.g., stripes/dots), or characters (e.g., ½, A/B) and the like. One of the two indicia may be displayed through the window prior to the needle 135 being loaded onto the suturing device 10 to signify that the needle loader 100 contains a sterile needle and is ready for use (e.g., via display of a "green" color or the like). The other indicia (e.g., display of a "red" color or the like) may only become visible after the needle is in position to be loaded into the suturing device, or after the needle has actually been loaded into the suturing device. Thus, the visual indicia 180 can confirm that the loading is complete.

It will be appreciated that indicia can be provided in different locations and by way of using different mechanisms. For example, a different portion of the movable assembly including arm 120 can include indicators in different locations that can be viewable through windows similar to window 184 in different locations. For example, visual indicia can be provided additionally or alternatively on spring 160 that can be visible through a designated window in the housing 110. If desired, other portions of boom 126, needle mount 130, or hub 121 can be provided with such indicia. By way of further example, a portion of the movable arm assembly 120 can cause a visual or tactile indicator formed into the housing 110 to move from a first position to a second position. For example, spring 160 or another movable component coupled to hub 121 can be configured to move a second element, such as a movable stop (e.g., if boss 115 were movable from a first position to a second position) from a first position to a second position. Such movement can include moving a movable button from a first position wherein the button is located inside the housing 110 to a second position wherein the button extends from the housing. Alternatively, the movable assembly can be provided with indicia in multiple locations to provide a plurality of indicators so that at least one of the indicia is visible when viewing the needle loader from multiple angles.

Regardless, after needle loading is complete, the suturing device 10 can then be removed with the needle 135, and the visual indicia can confirm to personnel that the needle loader has already been used. The needle loader 100 can then be discarded (if the device is a single-use device) or the needle loader 100 can be sent for reprocessing and loading of a new suture needle (if the device is a multi-use device). By way of further example, the indicator 180 can confirm that the movable arm 120 has reached the second position by emitting a sound, a tactile signal, and/or by displaying visual indicia as described. Likewise, the snapping of a lock over a pawl as previously described can also provide an aural indication that the needle 135 has been loaded into the suturing device. The indicator 180 can include a portion that confirms by tactile feel that the movable arm 120 has reached the second position by moving from a first indicator position to a second indicator position such as by protruding through the housing after the needle is loaded. It will be appreciated by those of skill in the art that, if desired, the other embodiments described herein (200, 300, 400, 500, 600, 700, 800) may also include visual and/or audible or tactile indicia indicating that a needle has been loaded into an inserted suturing device and/or indication of a spent/used needle loader.

It will be appreciated that the suturing device 10 can be provided in a variety of configurations. Optionally, in some implementations, the suturing device can be provided with a door, hatch or removable cover that can be displaced or removed to expose a needle track of the suturing device, and/or a location in which an arced suturing needle can be deposited by a needle loader. In such cases, the door, hatch or removable cover may be displaced to permit the needle loader to deposit the needle on or in the suturing device.

In one example, the suturing device can optionally include a retractable cover that covers the needle track when in a closed position. As a consequence of engaging the needle loader with the suturing device, the retractable cover may be retracted to facilitate loading of the needle into the track. For example, in accordance with additional aspects of the present disclosure, the needle loader can further comprise a protrusion that extends into a path of a suturing device to be loaded with a needle from the needle loader, wherein the protrusion causes an arced needle track of the suturing device to be exposed as the suturing device is advanced along the path. It will be appreciated by those of skill in the art that the needle loaders described herein can be provided with one or more structural features (bosses, arms, and the like) that facilitate exposing a target location in a suturing device in which to deposit a needle, such as a needle track.

However, it will be appreciated that such a feature is optional. The needle loaders described herein can be configured to engage a suturing device that does not include a retractable cover or door or the like. For example, a suturing device can be provided with a receiving portion for receiving a needle that is configured to deflect or deform to permit the needle to be inserted. For example, the needle may be received by a resilient material disposed on a portion of a suturing device. Alternatively, the needle (e.g., 135) can include ferromagnetic material, and the suturing device may include a magnetized portion that attracts and retains the needle in the suturing device with or without the use of a cover to keep the needle from falling out of the device. In another example, a suturing device may have a manually removable cover that is configured to be manually removed by a user or tool before loading the suturing device with a needle.

For purposes of illustration, and not limitation, with reference to FIGS. 1C and 1D, the housing 110 of the needle loader 100 can further define an opening 108 therein for receiving the suturing device 10, wherein the opening 108 at least in part defines the path to insert and load the needle 135 into the suturing device 10. In some implementations, such as the depicted embodiment, the suturing device 10 can include a retractable cover (illustrated as a sliding cover) to cover the needle track, and the protrusion 152 can retract the retractable cover of the suturing device 10 to expose the arced needle track. The sliding cover of the suturing device 10 is preferably spring loaded so that the cover slides back into place after being withdrawn from the needle loader 100. In some implementations discussed in further detail below, the protrusion can be coupled to the needle mount instead of the housing 110. In other implementations, the protrusion can be coupled to the housing (e.g., 110).

Figure 2A:
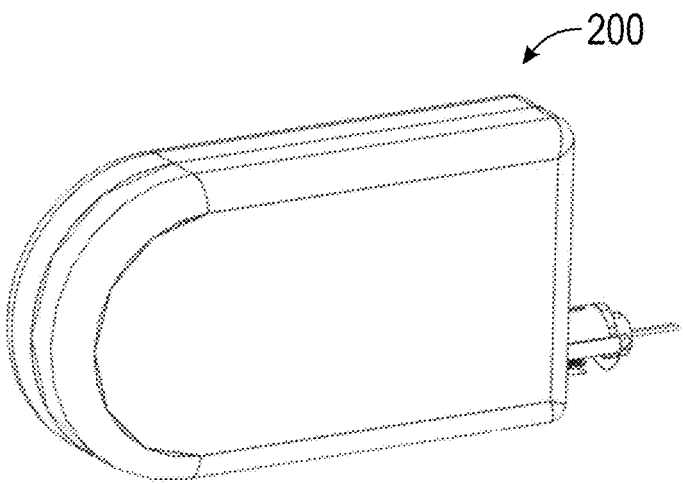
FIGS. 2A-4E depict views of a needle loader device in accordance with some embodiments of the present disclosure, or aspects or variations thereof.
Figure 2B:
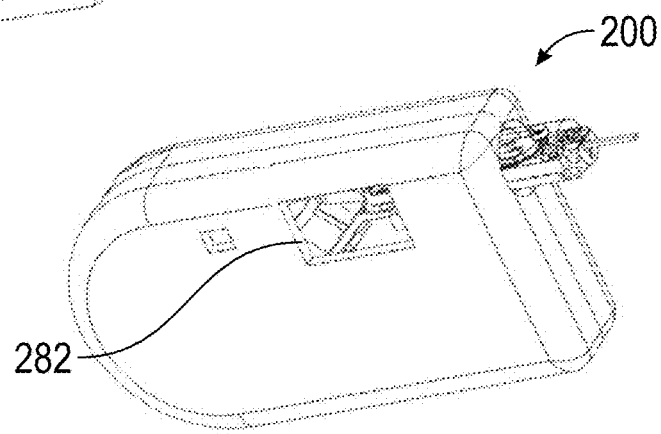
Figure 2C:
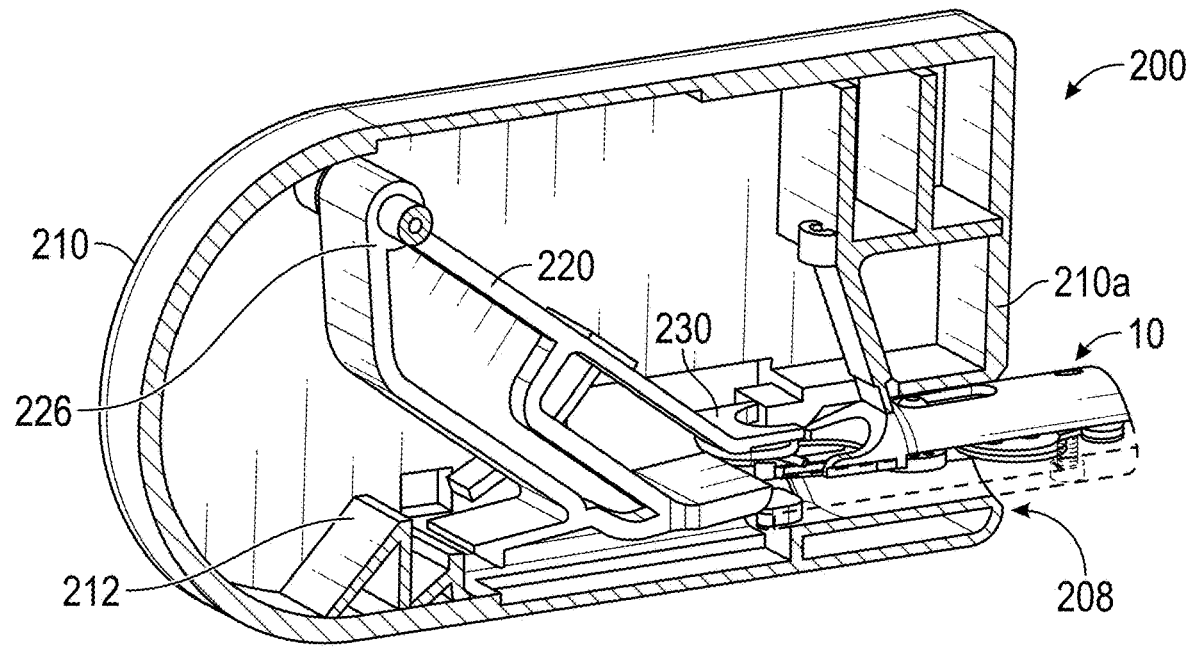

FIGS. 2A and 2B depict isometric exterior views of a representative embodiment of a needle loader 200 in accordance with the present disclosure. FIG. 2C illustrates a view of needle loader 200 that removes a portion of the external housing to view interior components of the loader 200.

It will be apparent that loader 200 shares a number of features with loader 100 described above. For example, similar to needle loader 100 described above, insertion of the suturing device 10 into needle loader 200 causes pivoting motion of a movable assembly of the needle loader 200 to cause loading of suturing needle 235 into the suturing device 10. For example, an arm 220 pivots about an axle 226 between a first position wherein a needle mount 230 is spaced apart from a needle track of a suturing device 10 to a second position wherein the needle mount is adjacent the needle track of the suturing device 10 for needle loading. The needle loader 200 includes a housing 210 that defines an elongate passage 208 to receive the suturing device 10. The elongate passage 208 begins at a first external surface 210a of the needle loader 200 and is directed inwardly toward the needle mount 230 of the needle loader.

With continuing reference to 2A-2C and 3A-3D, in operation, insertion of the suturing device 10 into the needle loader 200 causes the arm assembly 220 including arm 222 with a needle mounted thereon to pivot from a first position where the needle is spaced from the suturing device to a second position that causes the needle to be loaded into the suturing device. As the needle is being loaded into the device, a locking feature 242 engages a catch 212 of the housing 210 of the suturing device 200 to hold the needle mount in place. The suturing instrument (e.g., 10) can then be withdrawn from the needle loader 200 with the needle loaded therein.

Figure 3A:
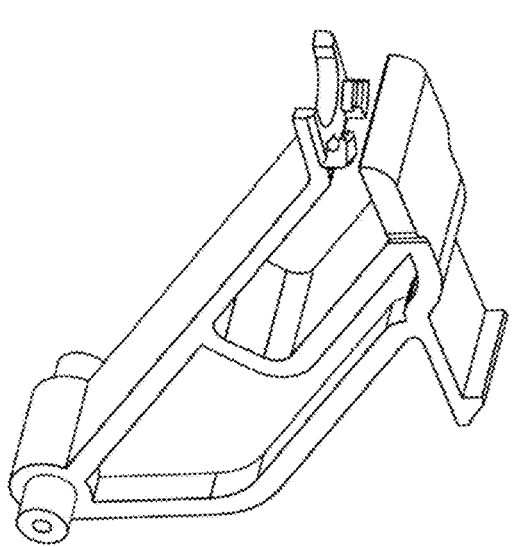
Figure 3B:
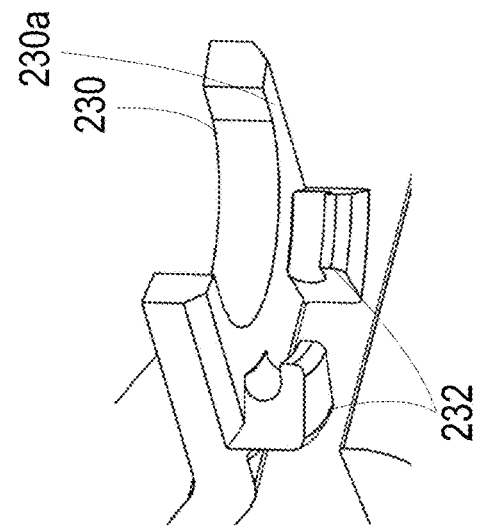
Figure 3C:
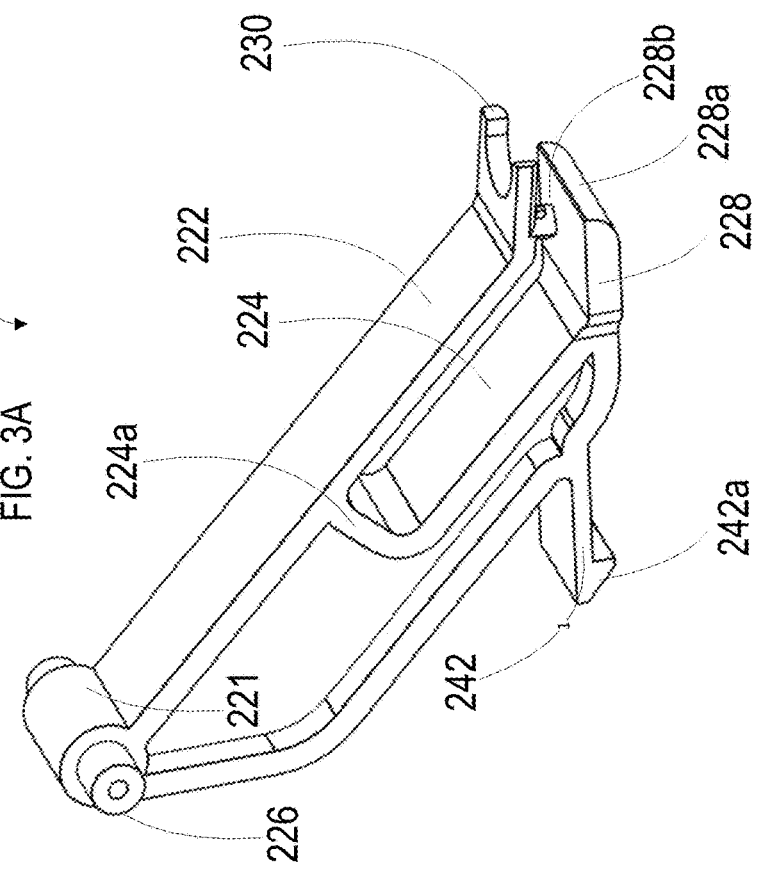
Figure 3D:
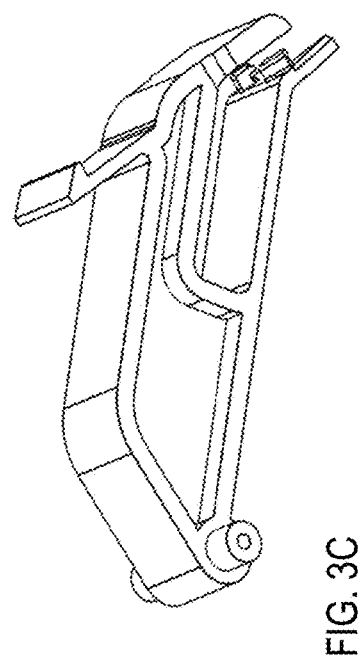
Figure 4D:
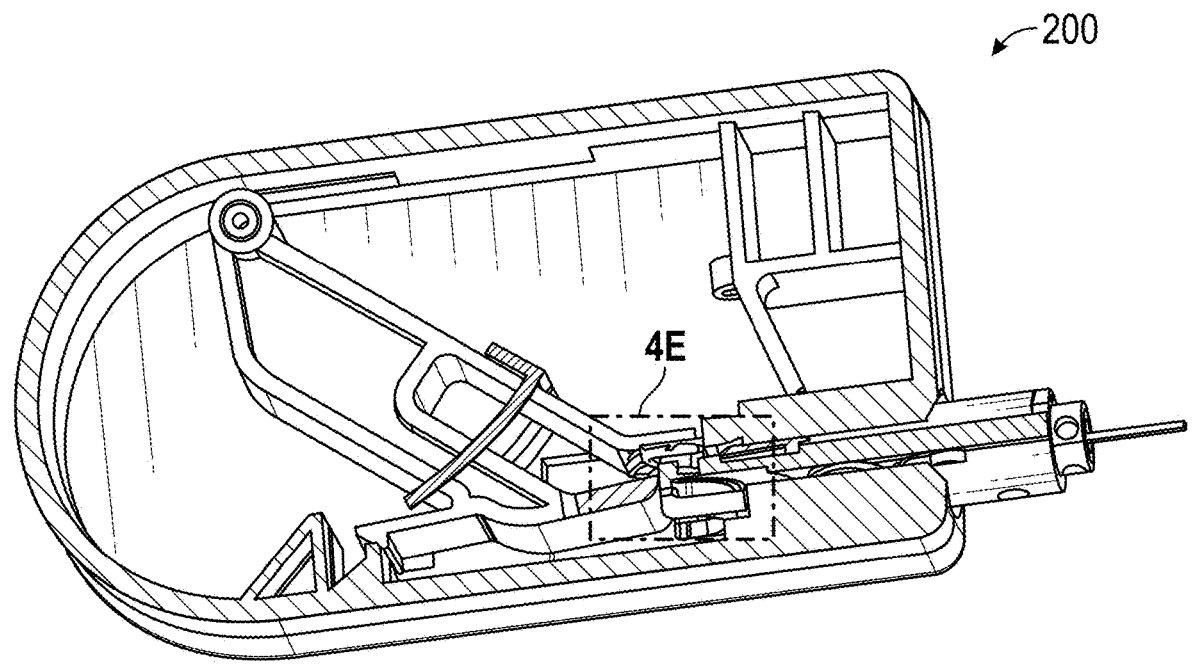
Figure 4E:
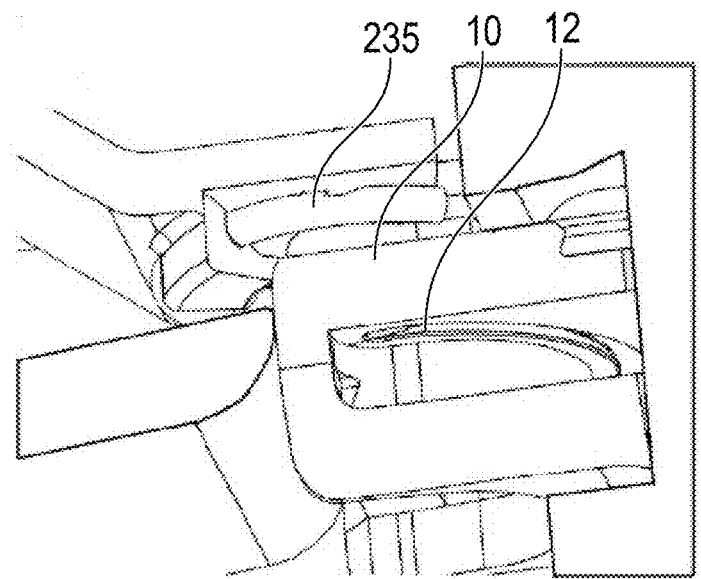

More particularly, and with reference to FIGS. 3A-3D, the arm 220 includes an upper arm portion 222 that extends away from hub 221 and terminates in needle mount 230. Needle mount 230 defines thereon a plurality of needle engagement portions 232, which can include one or more cleats, clips, or the like, to receive a suturing needle therein. Each cleat 232 is mounted on a surface of the mount 230 that faces a needle track 12 of a suturing device 10 as the suturing device 10 approaches the needle 235 as depicted in FIG. 4E. With reference to FIG. 3A, needle arm 220 further includes a second arm 224 that extends outwardly and downwardly from a middle region of arm 222. Arm 224 then executes a bend and traverses a path that is generally parallel to arm 222.

A lock, or locking feature, 242, includes a resilient cantilevered arm that extends in a direction opposite from a cam feature 228, and that terminates in a downwardly extending barb 242a. Needle loader 200 does not include a discrete spring member (e.g., 160) but could be modified to include such a spring member to resist forward movement of the suturing device 10 as the suturing device 10 is being loaded. The arm of locking feature 242 deflects upwardly about the point where it is mounted to arm assembly 220 as it passes over catch 212 of housing 210, and this deflection creates some resistance as the suturing device 10 engages the needle 235 attached to mount 230.

Arm 224 terminates in a cam feature 228 at the edge of a platform that traverses a path that is generally parallel to and beneath the needle mount 230. As depicted in FIG. 3A, the upper surface 228b of section 228 that faces the needle bearing surface 230a of the needle mount is actually angled toward that surface to some extent. With reference to FIG. 2C, the barb 242a of the locking feature 242 slides over a boss, or catch (or another barb) 212 defined in housing 210 as the arm 220 is pushed backwardly. This backward movement is caused by a distal end or end portion of the suturing device 10 urging against a curved or cam surface 228a. As arm 220 is pushed back by suturing device being advanced along passage 208 of needle loader 200, the spacing, or gap, between surfaces 228b and 230a expands, permitting a distal end portion of the suturing device 10 including needle track 12 to enter the spacing or gap between surfaces 228b and 230a. This permits the needle 235 mounted in cleats 232 to align with the needle track 12 of suturing device 10. Surface 230a then is able to align and contact, if desired, an upper surface of suturing device 10 that defines needle track 12 therein. Once so aligned, opposing first and second end sections of needle 235 align with and are received by the needle track 12, while the cleats 232 continue to hold the needle 235 in place with respect to surface 230a by way of an interference fit. However, once the first and second end portions of the arcuate needle are received by first and second ends of the arcuate needle track 12, this provides a sufficient interface to grip the needle so that the suturing device can be withdrawn and release needle 235 from the needle engagement features 232, illustrated here as fingers, but may include one or more cleats or clips.

The locking feature 242, in cooperation with catch 212 prevents the needle loader 200 from moving from the second position, wherein the needle is deposited in the suturing device 10, back to the first position. As such, the needle arm 220 remains in the second position and does not "follow" the suturing device 10 as the suturing device 10 is withdrawn from needle loader 200 because, at this point, barb 242a has engaged catch 212, locking arm 220 in place. To accommodate the movement of locking against catch 212, the arm of lock 242 deflects upwardly to permit the barb 242a to clear the catch, or cleat 212.

FIG. 2C presents an isometric view showing the relative positioning of components as suturing device 10 is advanced along passageway 208 prior to contacting cam surface 228a of arm 224. FIG. 4D shows an overall view from a lower perspective showing device 10 after suturing device 10 has contacted surface 228a, and FIG. 4E shows an enlarged view of a portion of FIG. 4D illustrating relative positioning of the needle 235 with respect to the needle track 12 of the suturing device.

FIGS. 4A and 4B show isometric views of the inner surfaces of the two halves of the housing 210. Each housing half is characterized by an inwardly facing wall including components (tabs, ridges, and the like) extending therefrom to support and guide operation of components of the needle loader 200. Each housing half defines a socket 216 to receive a respective end of axle 226 of arm 220. Each side of the housing includes an arcuate ridged guide 214 that extends inwardly from each side of the housing to support the movement of arm 220 as it pivots and prevents the arm 220 from buckling out of its intended plane of travel. One half of the housing 210 includes first and second tabs 214a, 214b to act as stops for the arm 220 to limit its range of travel. Window 284 is provided in one of the housing portions to permit a user to view engagement of the needle 235 with the needle track 12 of the suturing device 10.

For purposes of illustration, and not limitation, with reference to FIGS. 4A-4C, the housing 210 of the needle loader 200 can further define an opening leading to a passageway 208 thereinto to receive the suturing device 10. In the depicted embodiment of a needle loader 200, optionally, the suturing device 10 can include a retractable cover (illustrated as a sliding cover) to cover the needle track, and a tip 252 of a protrusion 250 coupled to an inner portion of the housing 210 can cause the retractable cover of the suturing device 10 to be retracted to expose the arced needle track for needle loading. More particularly, and with continuing reference to FIG. 4C, protrusion 250 is provided that extends in a cantilevered fashion extending downwardly from the housing from a fixed end 254 and at an angle toward the opening that leads to passageway 208 so as to intercept the suturing device 10 as the suturing device proceeds into the needle loader 200 along the path defined by the passage 208. A free end including a tip 252 of the protrusion 250 is located to contact an optionally slidably displaceable cover of the suturing device 10 to force the cover of the suturing device to retract backwardly as the suturing device 10 is advanced into passage. Protrusion 250 is canted against the direction of travel of the suturing device 10, and may flex about location 254, which can function as a hinge and deflect backwardly to some extent without being pushed out of the way and bent fully backward by advancement of the suturing device 10. Needle loader 200 can be provided with any desired features as described elsewhere herein, including but not limited to an indicator to indicate that the needle has been loaded, and/or that the needle loader has been used, as with the embodiment of FIG. 1.

An alternative embodiment of an arm assembly 220' is depicted in FIGS. 3E-3H that can be used in combination with a suitably configured housing of a needle loader similar to housing 210 of needle loader 200. It will be appreciated that corresponding components of housing 210 would need to be relocated or reconfigured somewhat to receive arm assembly 220', and that arm assembly 220' is not configured to be a drop-in replacement for arm assembly 220. In operation, arm assembly 220' functions similarly in a number of respects to arm assembly 220. Insertion of the suturing device 10 into a needle loader including arm assembly 220' including arm 222' with a needle mounted thereon causes arm assembly 220' to pivot from a first position where the needle is spaced from the suturing device to a second position that causes the needle to be loaded into the suturing device. As the needle is being loaded into the device 10, a locking feature 242' engages a catch (similar to catch 212 of the housing 210) to hold the needle mount 230' in place against a distal end portion of the suturing device 10. The suturing device (e.g., 10) can then be withdrawn from the needle loader 200 with the needle loaded therein.

More particularly, and with continuing reference to FIGS. 3E-3H, the arm 220' includes an upper arm portion 222' that extends away from a hub 221' and terminates in needle mount 230'. Needle mount 230' defines thereon a plurality of needle engagement portions 232', which can include one or more cleats, clips, or the like, to receive a suturing needle therein. Each needle engagement portion 232' is mounted on a surface of the mount 230' that faces a needle track 12 of a suturing device 10 as the suturing device 10 approaches the needle. Arm assembly 220' further includes a second arm 224' that extends outwardly and downwardly from a hub 221'. Hub 221' serves as a mounting point for arms 222' and 224' and defines a bearing surface or bore hole 226' to be received by a corresponding axle or boss of a housing of a needle loader (not shown).

A lock, or locking feature, 242', includes a resilient cantilevered arm that extends in a direction that is the same as from a cam feature 228a', and that terminates in a downwardly extending tip. Needle arm assembly 220' does not include a discrete spring member (e.g., 160) but can be modified to include such a spring member to resist forward movement of the suturing device 10 as the suturing device 10 is being loaded. The cantilevered arm, or paddle, of locking feature 242' deflects upwardly about the point where it is mounted to lower arm 224' so that, as the free end of feature 242' passes over a bump or a catch of a matching housing, the feature 242' passes over the bump or catch and then snaps in place behind it as the suturing device 10 engages a needle attached to mount 230'.

Arm 224' terminates in a pair of cam features 228a' that traverses a path that is generally parallel to and beneath the needle mount 230'. The cam features interact with (and are pushed by) a distal face of the suturing device 10 as the device is advanced into the needle loader, causing the arm assembly 220' to move downwardly until the needle is deposited in the suturing device 10. As the locking feature 242' slides over a respective boss or catch, a needle mounted in clips or cleats 232' aligns with the needle track 12 of suturing device 10. Once so aligned, opposing first and second end sections of the needle align with and are received by the needle track, while the cleats 232' continue to hold the needle in place. However, once the first and second end portions of the arcuate needle are received by first and second ends of the arcuate needle track, this provides a sufficient interface to grip the needle so that the suturing device can be withdrawn and release needle from the needle engagement features 232.

The locking feature 242', in cooperation with a corresponding catch in a housing (not shown) prevent the arm assembly 220' from moving from the second position, wherein the needle is deposited in the suturing device, back to the first position. As such, the needle arm assembly 220' remains in the second position and does not "follow" the suturing device as the suturing device is withdrawn from needle loader because, at this point, locking feature 242' has engaged a corresponding catch, locking arm assembly 220' in place.

FIGS. 5A-5O depict aspects of an embodiment of a needle loader 300 in accordance with the present disclosure. Embodiment 300 includes various similarities to needle loader 200. As depicted, housing 310 is divided into two halves that can each be individually molded, and include various structures to facilitate operation of the device 300, such as guide, bosses, sockets, and the like. The movable arm 320 of the needle loader 320 is depicted as being rotatable about a plurality of pivot points 321a, 321b between a first position wherein a needle mount 330 including a needle 335 is displaced from a needle track 12 of a suturing device, and a second position (e.g., FIG. 5C). Arm 320, as depicted comprises a four-bar linkage, wherein two bars of the linkage are formed by each of arms 322 and 324, a third bar is formed by the portion of housing 310 that connects the two sockets that rotatably receive first, upper ends of arms 322, 324, and the fourth bar is comprised of needle mount 330, which is hingedly coupled to arms 322, 324 at hinge points 327a, 327b. The four-bar linkage of the movable arm 320 is rotatable about two pivot points coincident with axles 321a, 321b that are received in corresponding sockets in housing 310, and as a consequence, rotation about those pivot points permits the arms 322, 324 to remain largely parallel when the arm 320 is articulated, and also helps keep the needle bearing surface of mount 330 to be parallel to the needle track 12 of the suturing device 10.

In operation, needle loader 300 receives a suturing device by way of an elongate passage 308 that initiates at an outer (preferably circular) opening 308a defined in an outer surface of the housing 310 of the needle loader 300. The suturing device 10 is advanced along passage 308 until a free end 352 of a protrusion extending from an inner wall of the housing into the passage 308 contacts concave outer surface of a retractable cover 14 of suturing device 10. This causes the cover 14 to be held in place while the other portions of the suturing device 10 continue to advance toward the needle 335 disposed on the needle mount 330. As a curved or ramped distal end face surface 328a of lower platform 328 contacts a distal region of the suturing device 10, the orientation of surface 328a causes arm 320 to be pushed backward and downward. Surface 328a remains in contact with a concave end face of the suturing device as loading is occurring. At this point, the downwardly facing surface 330a of the needle mount, which can hold the needle in place with cleats or other suitable means, comes into close proximity with the suturing device, and the needle 335 is received in the needle track 12 of the suturing device 10.

FIGS. 5A and 5B present cross-sectional views of this procedure, wherein the cross section is viewed down the longitudinal center of the suturing device 10 to illustrate how end face 328a (see also FIG. 5J) is received into an arcuate gap defined at the end of the suturing device 10, and how surface 328a contacts the concave surface at the apex of the arcuate gap of the suturing device 10. As is visible in the drawings, the needle mount 330 comprises a first surface 330a defining a boss or retainer thereon to receive the arced needle 335. Surface 328b faces the first surface 330a of the needle mount. The surface 330a and surface 328b therefore cooperate to define a gap therebetween to receive a distal portion of the suturing device 10. Surface 328b comprises a ramped surface to guide the arced needle track 12 of the suturing device 10 toward the arced needle 335 mounted on the needle mount 330 as the suturing device 10 is advanced along a path of travel with respect to the needle loader 300. After receiving the needle 335, the suturing device 10 can be withdrawn from the needle loader 300.

FIGS. 5D-5I provide additional views of the arm assembly 320 from a variety of views. FIGS. 5D-5I present a right-side elevational view, a back elevational view, a left-side elevational view, a front elevational view, a top plan view, and a bottom plan view, respectively. FIGS. 5J-5O present a front left upper isometric view, a bottom left isometric view, a top right isometric view, a bottom isometric view, a lower front isometric view, and a lower back isometric view, respectively. Corresponding components of arm assembly 320 are labeled with identical reference numbers.

With continuing reference to FIGS. 5D-5O, arm assembly 320 includes a first axle 321a coupled to upper arm (relatively upper per FIG. 5A) and a lower axle 322b coupled to lower arm 324. As is shown in FIGS. 5J and 5M, surface 328a includes a convex surface to engage a distally facing surface within the concavity of suturing device 10. Locking features 342a, 342b and 342c are also visible. Locking features 342a and 342b are locking features in the form of deflectable paddles, wherein each paddle extends from an arm that wraps around element 328. Specifically, a bent arm, or elbow extends laterally out of each side of element 328 that wraps around and enlarges. During operation of needle loader 300, the free ends of the locking features 342a, 342b slide past a catch, cleat or boss (not shown) inside of housing 310. If desired, the locking features 342a, 342b can be captured by a window defined in either wall of the housing (not shown) to verify when the needle and needle mount have reached a second position wherein the needle is able to engage the suturing device 10. Each outwardly facing surface of each paddle 342a, 342b can additionally be provided with visual indicia such that the indicia could be caused to overlap with an opening in the housing, as described above with respect to embodiment 100, to indicate if the needle loader 300 has been used, or whether it has already been used, and can be processed further to reload or dispose of it. It will be further appreciated that paddle 342a, 342b may simply be used as stabilizers to slide against inner walls of the housing 310 and not act as a locking mechanism. With continuing reference to FIGS. 5D-5O, arm assembly 320 can further include an additional locking feature 342c that can be configured to pass over a boss or a catch or a cleat after the arm assembly 320 has moved from the first position to the second position.

Needle loader 300 can be provided with any desired features as described elsewhere herein, including but not limited to a lock to lock the arm 320 in place after the needle has been loaded onto the suturing device, and an indicator to indicate that the needle has been loaded, and/or that the needle loader has been used, as with the embodiment of FIG. 1.

In further accordance with the disclosure, needle loader devices can be provided that utilize a sliding action to translate an arm assembly bearing a suturing needle from a first position to a second position. For example, insertion of the suturing device can cause a movable assembly or arm assembly of the needle loader to be moved relative to the housing along guide tracks defined in the needle loader housing to effectuate needle loading. This can be accomplished in a variety of ways.

For example, as illustrated in FIGS. 6A-6E a further embodiment of a needle loader 400 is presented in accordance with the present disclosure, or aspects thereof. Embodiment differs from the previous embodiments (100, 200, 300) in several respects. For example, needle loader includes a slidable arm, or arm assembly, 420 having bosses or guides 421 that slide in and are guided by one or more tracks 411 (FIG. 6D) defined by the housing 410. While the tracks 411 are depicted as being linear to provide linear motion, the track 411 can also be curved or arced, as desired. The arm assembly 420 moves from a first position (FIG. 6A) wherein the arm assembly 420 is closer to the opening 408a that partially defines the passageway 408, to a second position (FIGS. 6B, 6C) wherein the arm 420 has slid along the tracks 411 on guides 421 and the needle has been loaded into the suturing device 10.

Figure 6A:
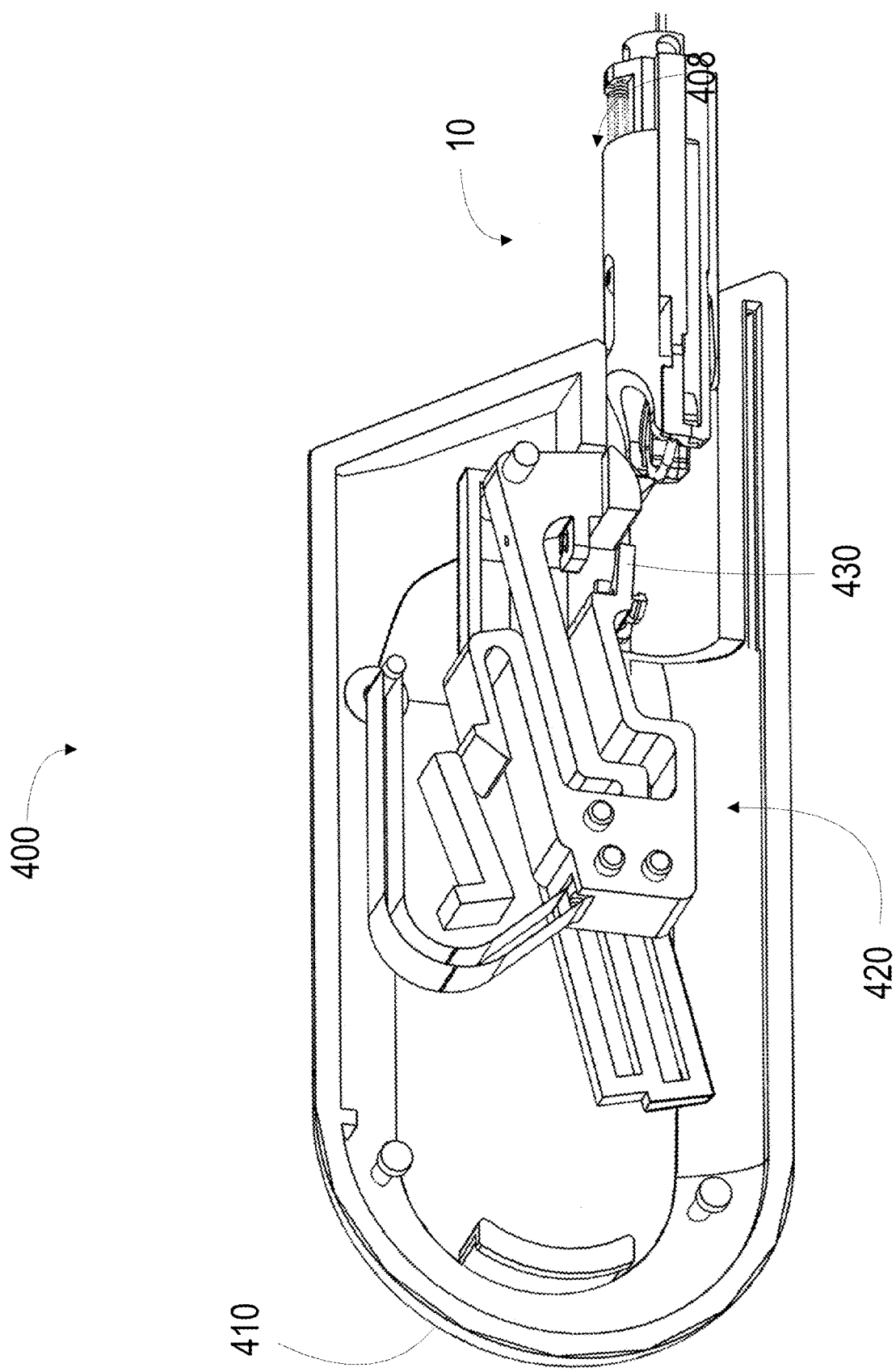
FIGS. 6A-6E depict views of a needle loader device in accordance with some embodiments of the present disclosure, or aspects thereof.
Figure 6B:
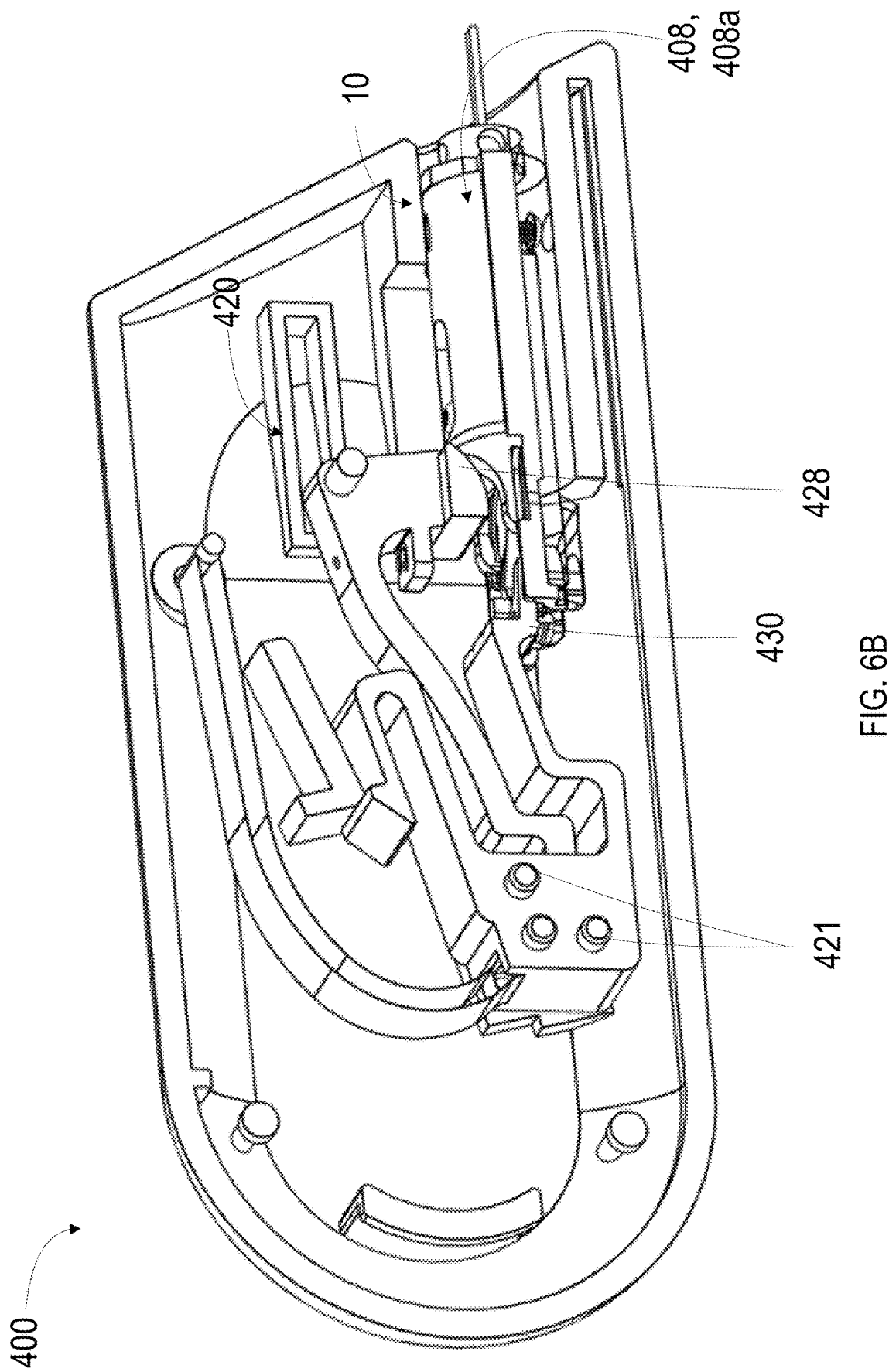
Figure 6C:
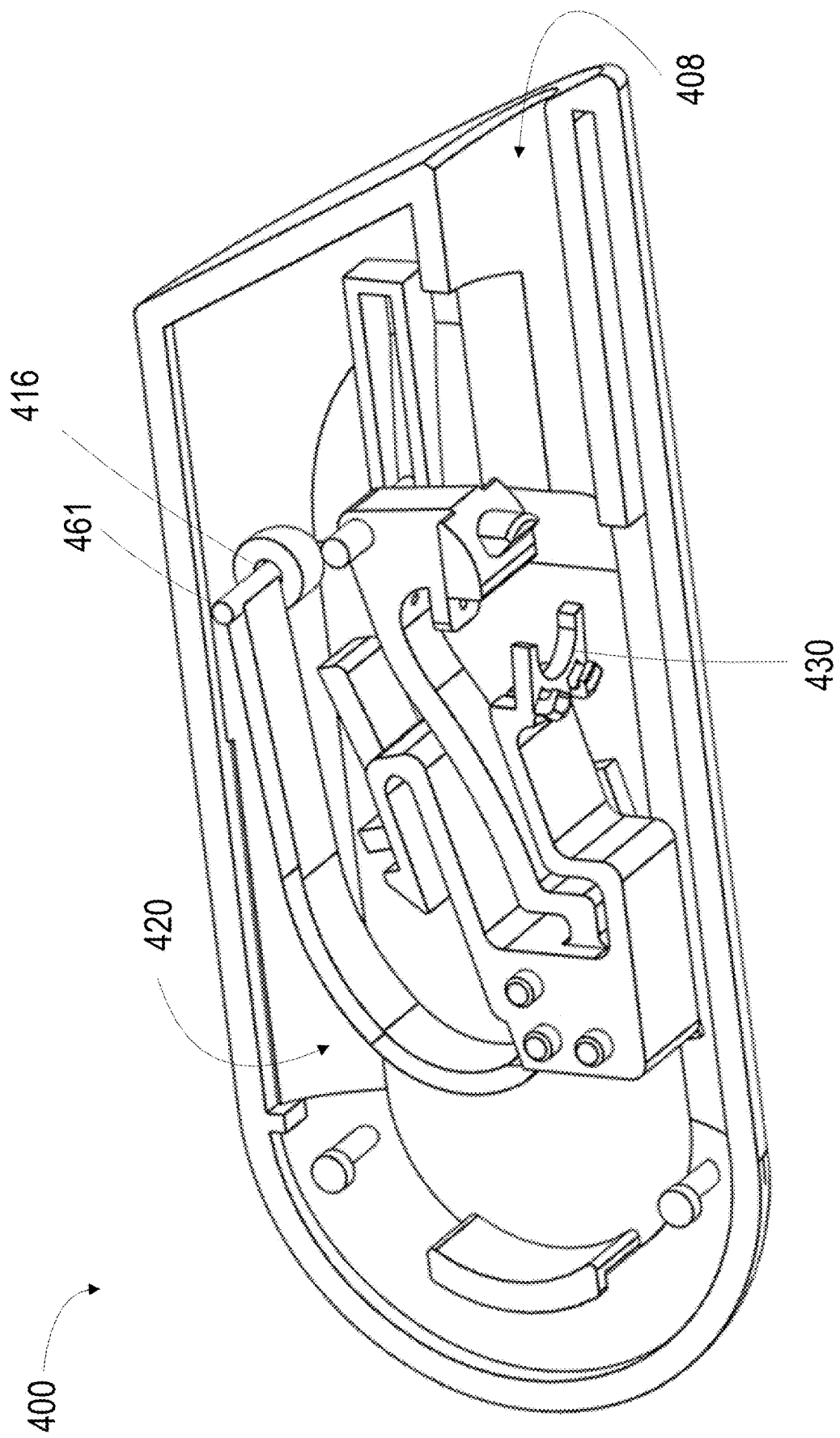
Figure 6D:
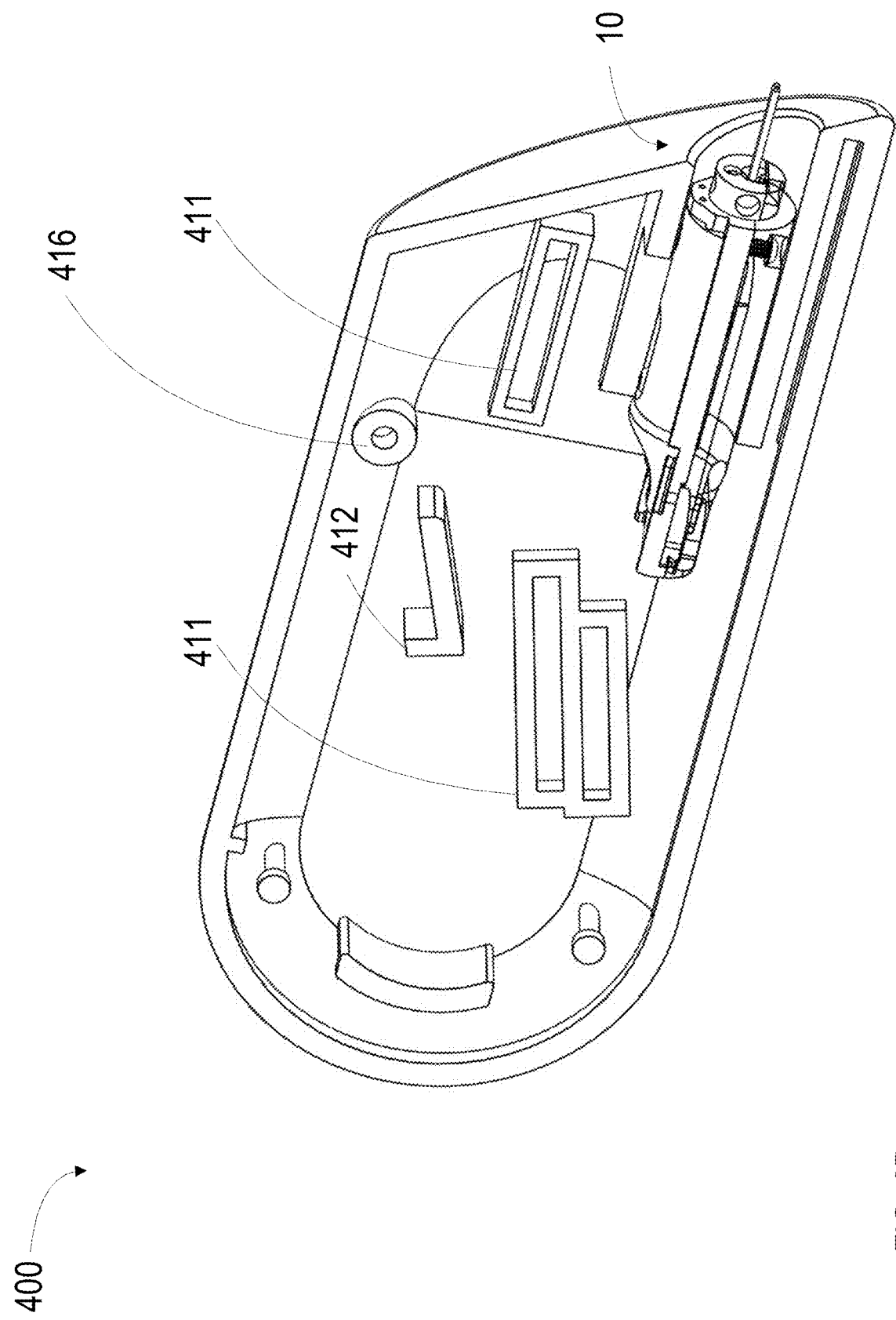
Figure 6E:
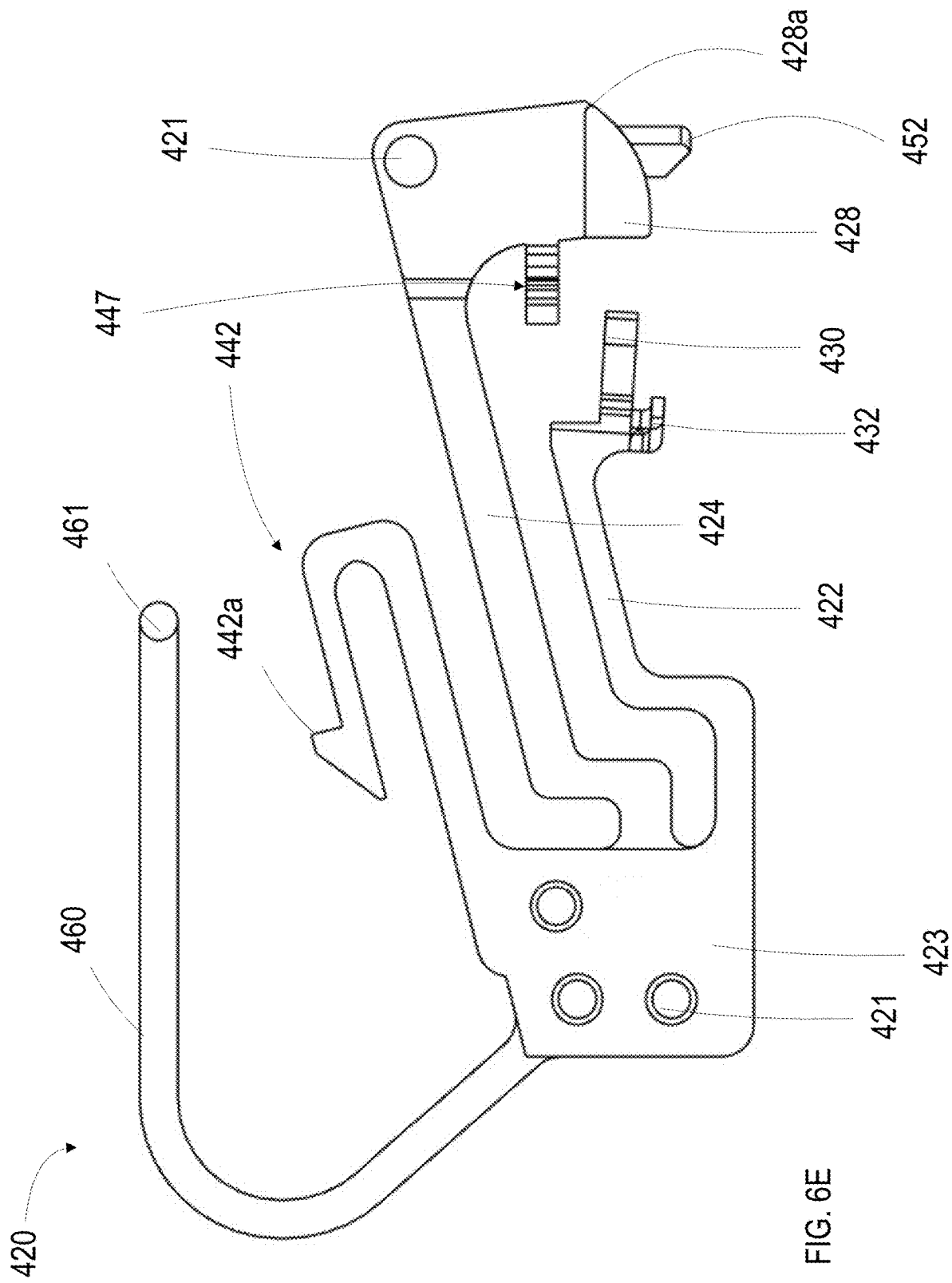

With reference to FIG. 6E, arm or arm assembly 420 includes a main hub 423 that includes a plurality of bosses defined on each side thereof to be guided by corresponding tracks defined in the housing 410. Hub 423 includes a plurality of arms extending therefrom. An arm 422 extends from a lower portion of the hub 423 that terminates in a needle mount 430 having one or more needle retention features, such as fingers, clips or cleats 432 to hold a suturing needle (not shown) in place. A suture retention feature, clip, finger or cleat 447 can be provided to hold the suture that is attached to the suturing needle to help hold the suture out of the way as the needle loader 400 is loading a suturing device with a suturing needle. A second arm 424 extends outwardly from the hub 423 and extends over and around arm 422 and the needle mount 430. Arm 424 then extends downwardly and terminates in a curved surface 428a that rides over the top of the distal end of the suturing device 10 when it is inserted, and downwardly extending protrusion 452 acts to engage the cover of the suturing device to cause the cover to be pushed back to expose the needle track. Arm 442 also extends outwardly from the hub 423 and terminates in a locking feature 442a, which may be in the form of a barb to engage with cleat or boss 412 defined in the housing 410 (FIGS. 6C, 6D).

A fourth arm, or spring, 460 also extends outwardly from the hub, and terminates in axle 461 that is received within sockets 416 defined in the housing. FIG. 6C shows the barb 442a engaged with the cleat 412, but shows axle and spring 460 displaced with hub 423 for purposes of illustration. In actual operation of the needle loader 400, the axle 461 remains in sockets 416, so that as the hub 423 and arms are pushed further into the housing by suturing device 10 along tracks 411, spring 460 is stretched and deformed to provide a countervailing force against the advancement of the suturing device 10. As further shown in FIG. 6E, arm 424 can be provided with a guide or boss 421 to ride in a dedicated track 411 defined in the inner surface of the housing 410. Tracks 411 are illustrated in FIG. 6D. FIG. 6B shows the arm assembly 420 at its starting point. FIG. 6A shows the relative position of the arm assembly 420 and the suturing device 10 after the needle has been delivered to the suturing device 10, but illustrates the spring axle 461 as not being engaged with the socket 416.

In use, needle loader 400 is used by inserting a distal end of the suturing device 10 into the opening 410 until surface 428*a* contacts the sliding cover of the suturing instrument 10. It should be appreciated that the sliding cover is optional and may not be present in some embodiments. The further advancement of suturing device 10 along passage 408 pushes arm assembly 420 further into the housing (to the left as illustrated in the drawings) against the force of spring 460, which is being deformed and straightened in the process, thereby acting as a tension spring, and the slanted directionality of the tracks 411 cause the arm assembly 420 to move downward as well as along the direction of travel of the suturing device 10. As the needle mount 430 travels in this matter, it approaches the needle track along a vertical direction until the needle is pushed into the arced needle track of the suturing device. By this time, barb 442*a* has slid along and engaged boss 412, preventing backward movement of the arm assembly 420 as the suturing device is withdrawn.

Needle loader 400 can be provided with any desired features as described elsewhere herein, including but not limited to an indicator to indicate that the needle has been loaded, and/or that the needle loader has been used, as with the embodiment of FIG. 1.

In further accordance with the disclosure, further embodiments of a needle loader are provided wherein insertion of the suturing device into the needle loader causes sliding movement of an arm assembly that includes a suturing needle to be loaded into the suturing device from a first position to a second position. Optionally, such devices can be configured to facilitate removal or retraction of a cover of a needle track of the suturing device. Also, optionally, the needle loader can include a predetermined length of suturing material of various types (conventional, barbed, absorbable, and the like) that may be held in place in a suture compartment and/or wound around one or more bosses. The other embodiments herein can be provided with suturing material disposed in a suture compartment and/or wound around a predetermined path within a portion of the needle loader.

Figure 7G:
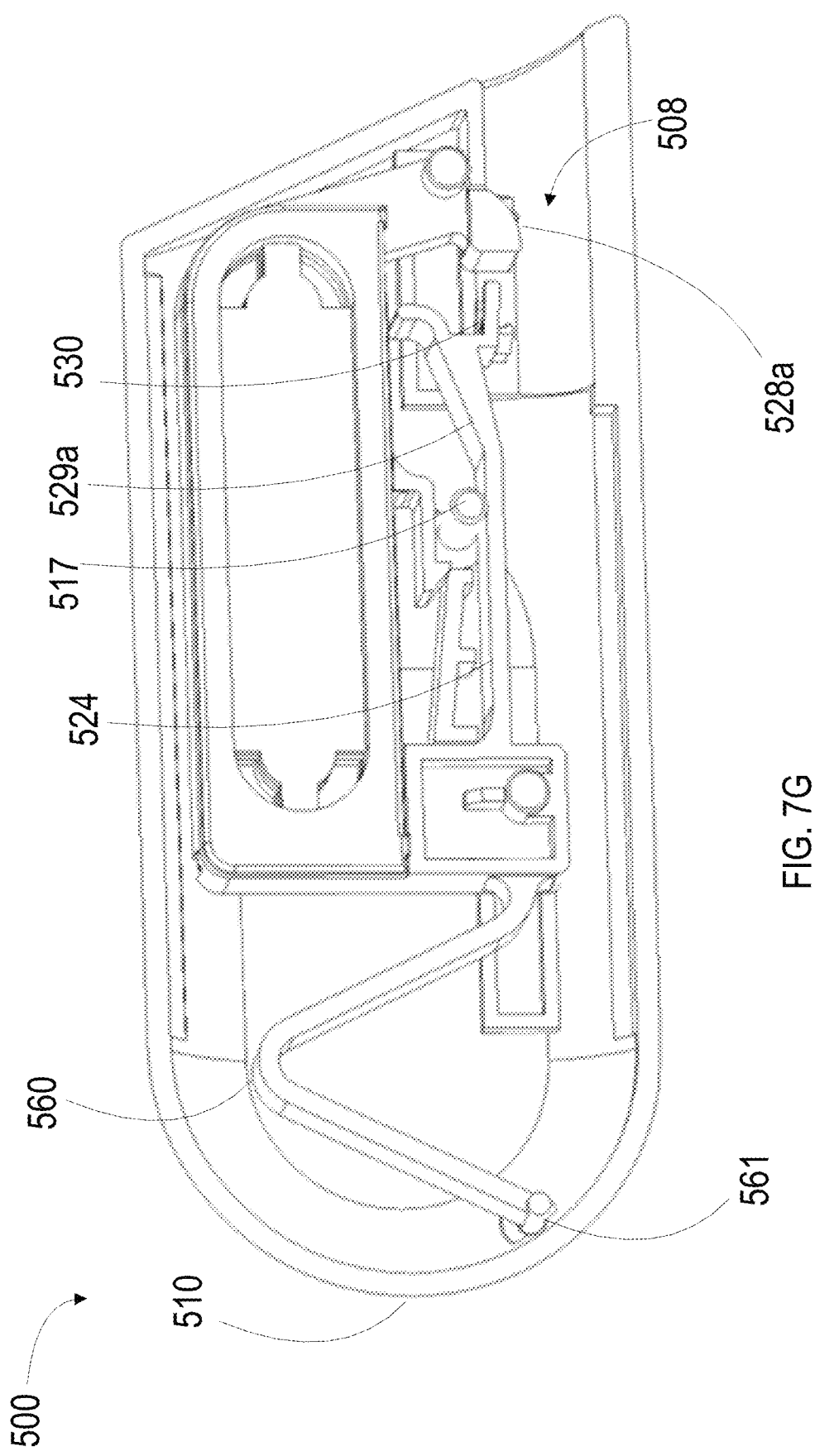
FIGS. 7A-7N depict views of a needle loader device in accordance with some embodiments of the present disclosure, or aspects thereof.
Figure 7I:
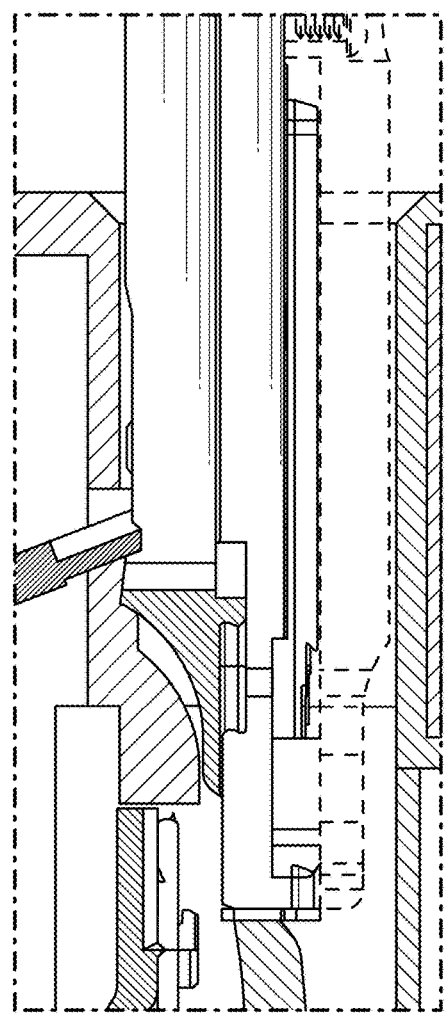
Figure 7H:
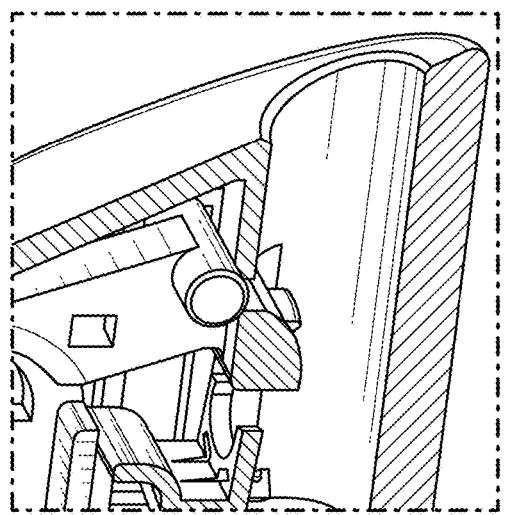
Figure 7J:
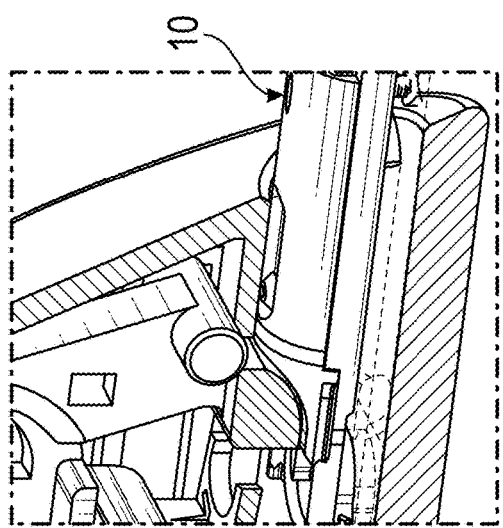
Figure 7L:
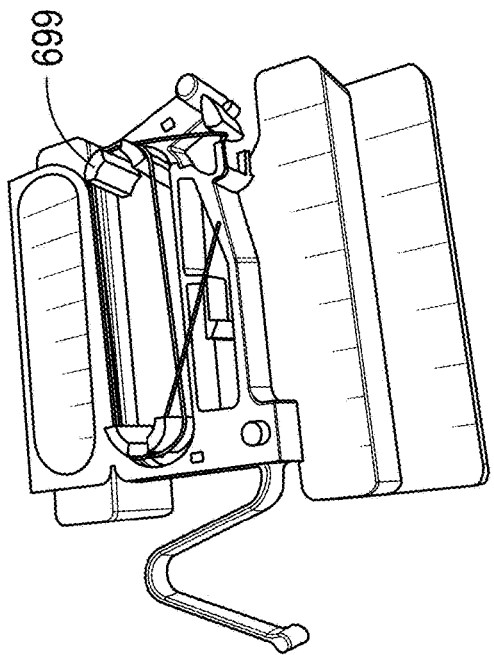
Figure 7N:
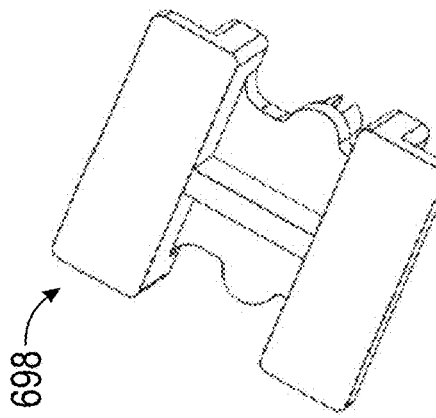

For purposes of illustration only, and not for purposes of limitation, FIGS. 7A-7N illustrate another embodiment of a needle loader 500 in accordance with the present disclosure, or aspects thereof. Needle loader 500 is generally similar in a number of aspects to the previous embodiments. In particular, the general configuration of loader 500 greatly resembles loader 400, in that loader 500 includes an arm assembly 520 with guides or bosses 521 that ride in corresponding tracks 511 formed in the housing 510 of the loader 500.

However, needle loader 500 additionally includes a suture compartment 590 to hold a length of suture that is coupled to the arced needle that is disposed in the loader 500. The length of suture can be, for example, between about six and about 24 inches in length. As illustrated, the suture compartment 590 is coupled to the hub 523 of the arm assembly 520. In the illustrated embodiment, the suture compartment is integrally formed with the arm assembly 520, but compartment may instead be formed into the housing 510, or may be a separate component. The suture compartment 590 can be coupled to the needle mount 530, if desired. If desired, the suture compartment 590 can be integrally formed with the needle mount. As depicted, the suture compartment 590 can be oblong in shape. In some implementations, the suture compartment can be defined by a peripheral curved wall. The peripheral curved wall can be circular in shape, elliptical in shape, or a combination of different shapes. An example of such an elliptical or circular suture compartment 690 can be seen with reference to needle loader 600 depicted in FIGS. 8A-8C, discussed in further detail below.

FIG. 7G illustrates relative placement of components in the needle loader 500 prior to insertion of the suturing device 10 therein. When the instrument 10 is inserted into passageway 508, surface 528*a* urges against the suturing device 10 and the arm assembly 520 is pushed further into the housing 510, which also causes spring 560 to start compressing and urges against the suturing device 10 with a force that increases as the suturing device is inserted further into passageway 508. The protrusion 552 (FIG. 7E) then engages the optional cover of the device 10, causing the cover to be retracted due to the force delivered by the spring 560. As the suturing device is pushed still further in to passageway, upper surface 529*a* begins to ride along boss 517, and the upwardly inclined angle of surface 529 then causes arm 524 and needle mount 530 to be pushed downward toward the needle track of the suturing device, resulting in alignment of the needle with the needle track, and then deposition of the needle into the needle track of the suturing device 10 Relative placement of the suturing device and the loader 500 can be seen in FIGS. 7H-7J. A locking feature 542*a*, which may be in the form of a barb (see FIG. 7B), then slides over a corresponding cleat 512 formed into the housing 510. Engagement of this locking mechanism thereby prevents the arm assembly 520 from moving with the suturing device 10 as the suturing device is withdrawn. Similar to embodiment 400, spring 560 includes an axle 561 that is received by one or more sockets 516 defined in the housing. However, spring 560 functions as a compression spring, rather than a tension spring.

Figure 7K:
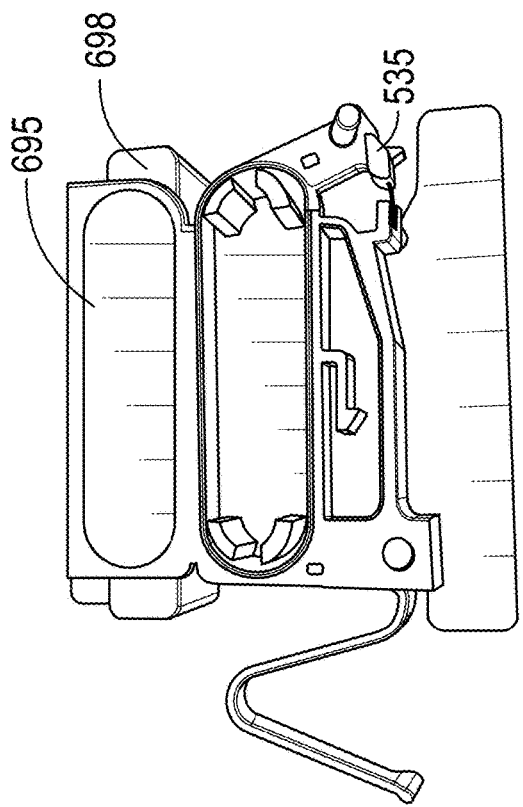
Figure 7M:
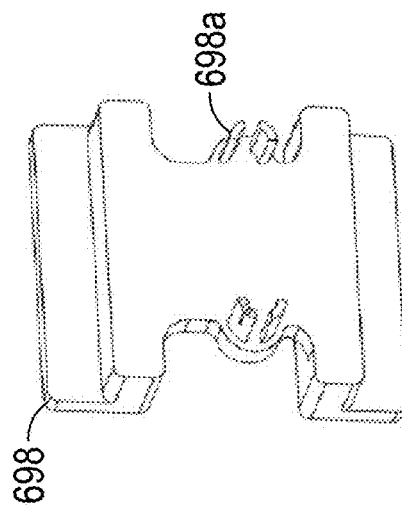

FIG. 7A illustrates relative lateral placement of the arm assembly 520, but does not illustrate deflection of arm 524 with respect to boss 517 for purposes of illustration. As illustrated, FIG. 7B shows the relative location of hub 523 to boss or guide 521, and illustrates openings 592 in suture compartment to receive a suture winding fixture 698 as illustrated in FIGS. 7K-7N to dispose suture 699 in the suture compartment 590. The suture compartment 590 of FIG. 7K is illustrated showing a hinged cover 595 attached thereto that can be closed upon suture being deposited therein that is attached to a needle 535. The cover 595 can also be a separate component. Winding bosses 698*a* are defined on winding fixture 698, which are slid through openings 592 in suture compartment 690. Suture 699 is then wrapped around the bosses 698*a* to properly align suture in the compartment 590. The fixture 698 can be configured to snap over the suture compartment or simply align with it. Once the suture is wrapped, the fixture can be removed, and the cover 595 can be closed, and the loader 500 can be assembled, packaged and sterilized.

Figure 8A:
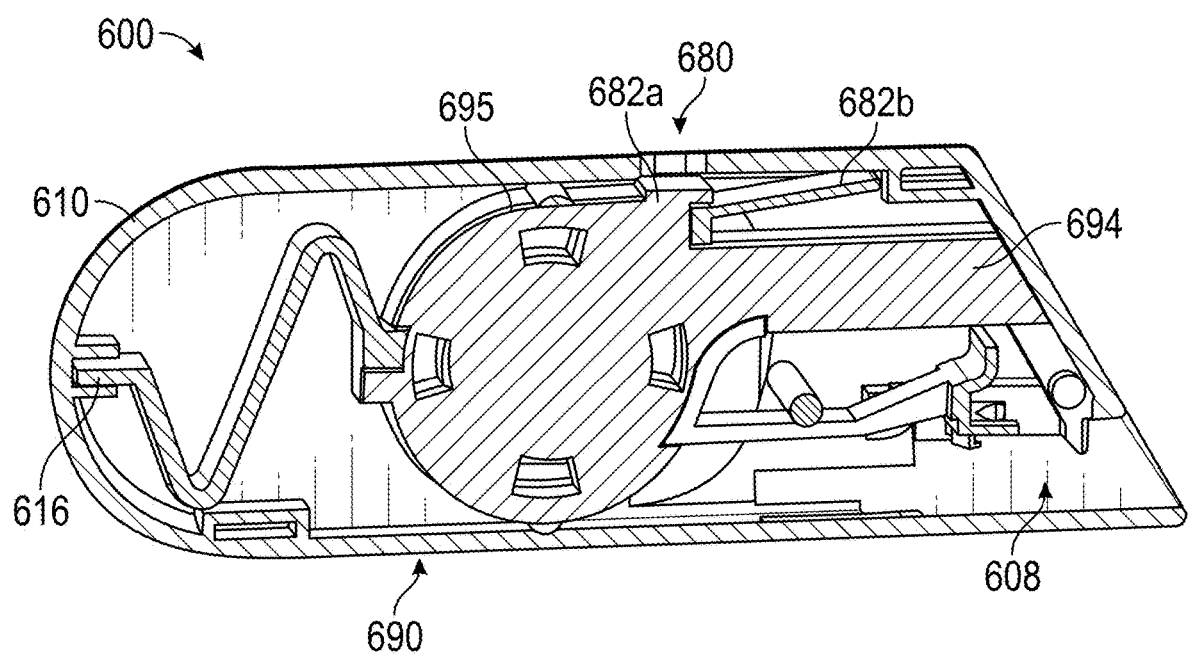

FIGS. 8A-8C present a needle loader 600 that is a variation of loader 500. For example, loader 500 provided an oblong suture compartment 590, whereas embodiment 600 provides a modified design that is generally circular in shape. If desired, the compartment can be elliptically shaped. Needle loader 600 can include one or more contoured gripping surfaces 603 formed into the housing 610 to facilitate gripping needle loader 600 by a user when installing a needle on suturing device 10.

In addition, needle loader 600 illustrates an optional visual indicator 680 at a top edge thereof, wherein a first indicator 682a having indicia reflecting that the loader 600 has not been used, is aligned with a window through the housing 610 prior to using the loader. When the suturing device has been inserted into opening 608 and the loader is used, the assembly including the arm 624 and the suture compartment 690 is slid to the left (with respect to FIG. 8A), and a second indicia 682b is visible through the window, indicating that the loader 600 has been used. Indicia 682b is formed onto a deflectable paddle that passes over a cleat 612 formed into the housing (FIG. 8C), and holds the inner assembly of the loader 600 in place. A spring 660 is also provided in the form of a compressive spring that can have any one of a variety of shapes. For example, the spring 660 need not rigidly anchor to the housing 610 because it is being compressed. Thus, while a socket 616 can be provided to receive a free end of the spring 660, the spring can be configured as illustrated in FIG. 8B and urge against the inner surface of the housing 610 of the loader 600. The arm 624 is deflected by sliding over boss 617 to help advance the needle mount 630 downwardly toward the needle track 12 of the suturing device 10 in a manner similar to embodiment 500. Suture compartment 690 includes guides or bosses 621 thereon to ride in tracks 611 defined on an interior surface of the housing 610.

Figure 9A:
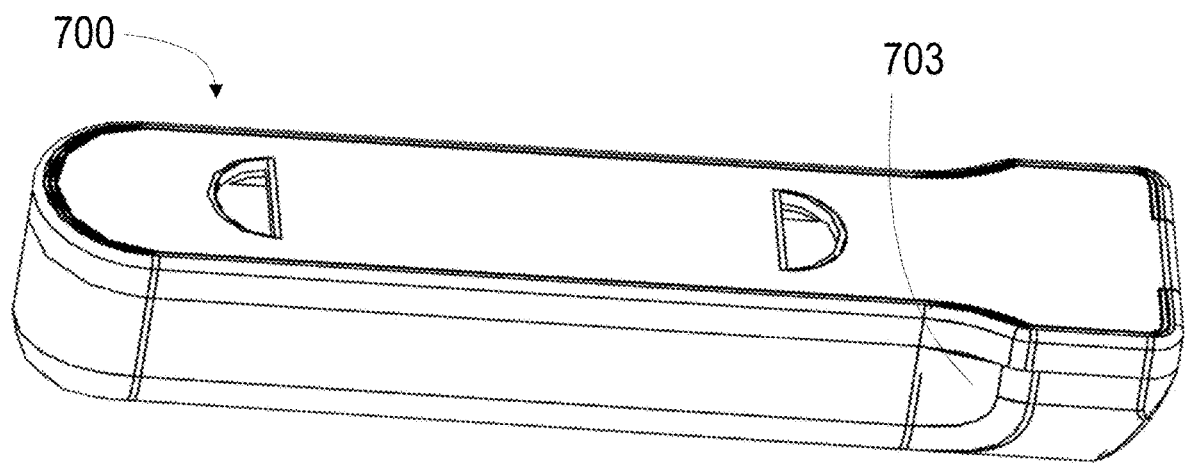
FIGS. 9A-9P depict views of a needle loader device in accordance with some embodiments of the present disclosure, or aspects thereof.
Figure 9B:
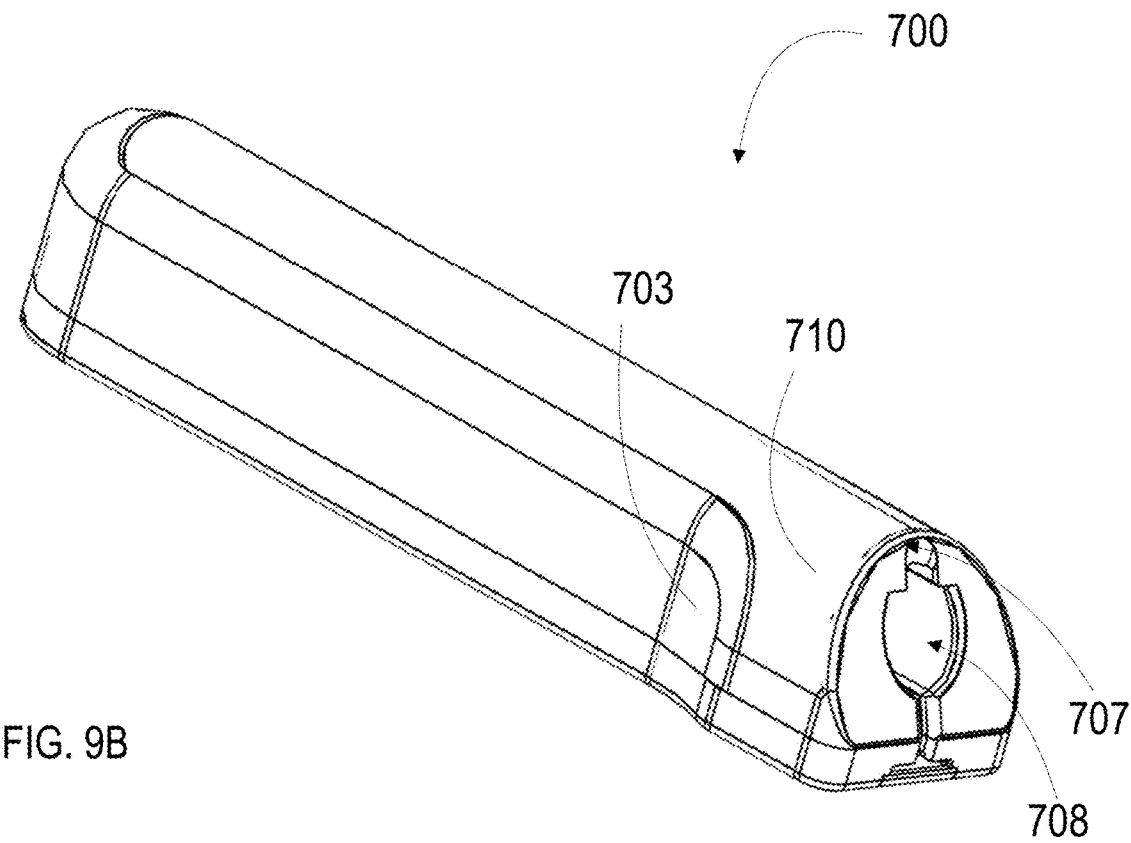
Figure 9E:
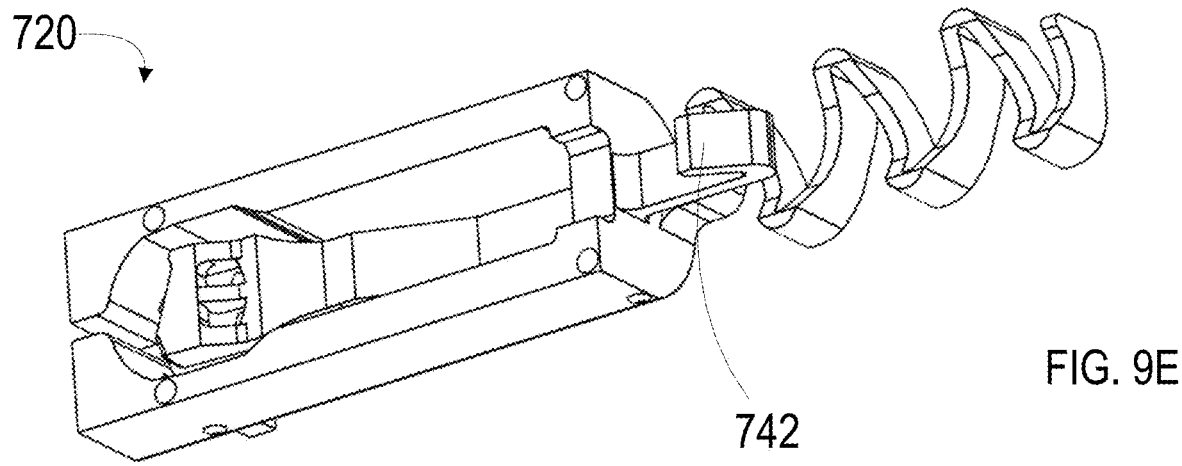
Figure 9F:
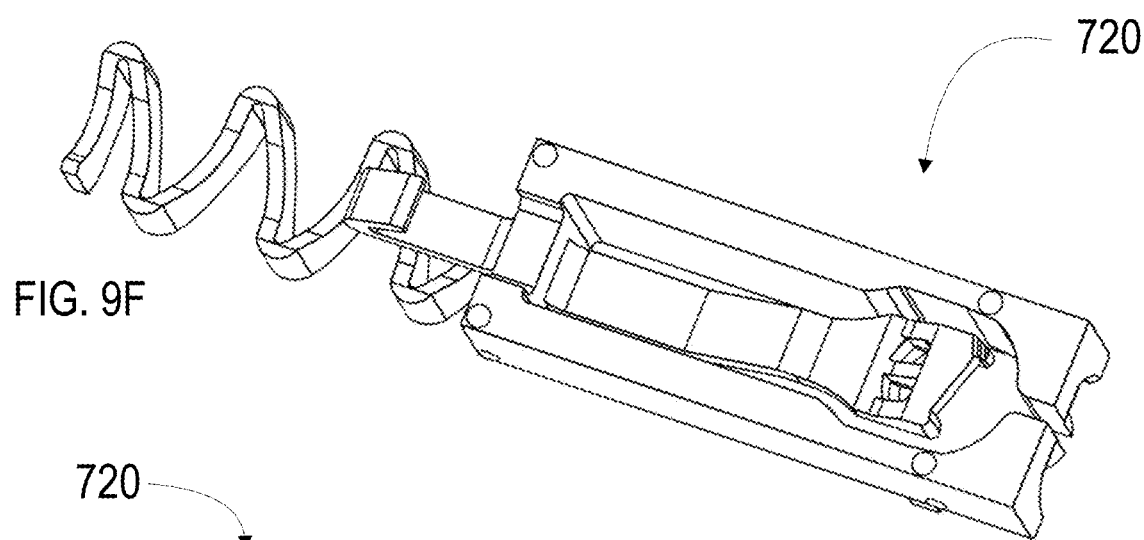
Figure 9G:
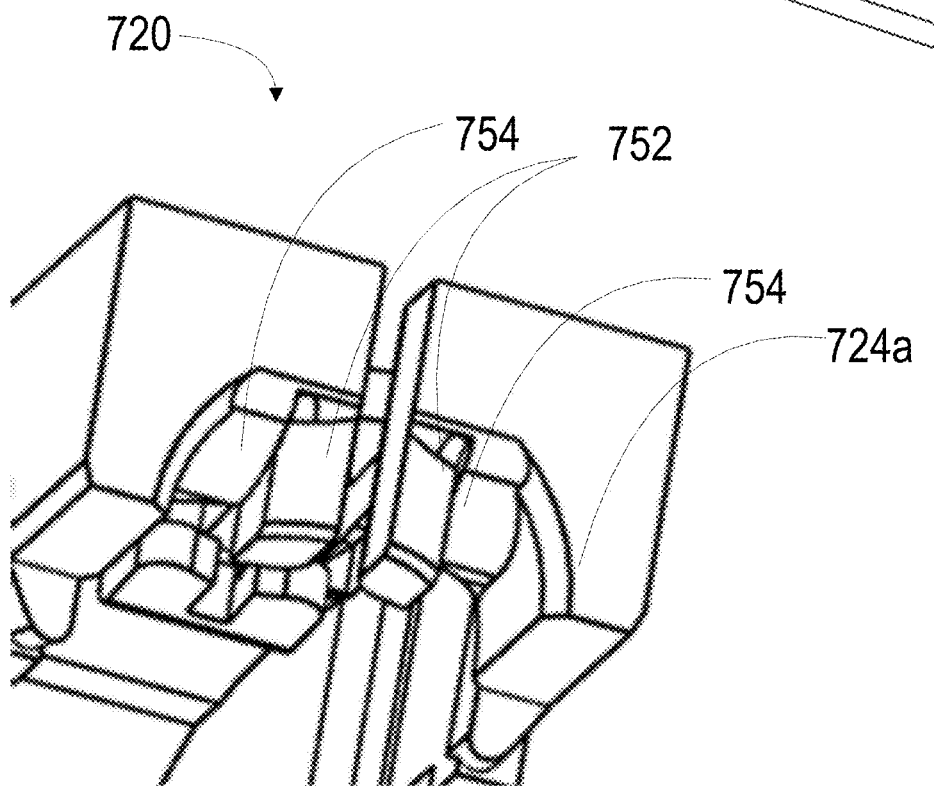
Figures 9O, 9P:
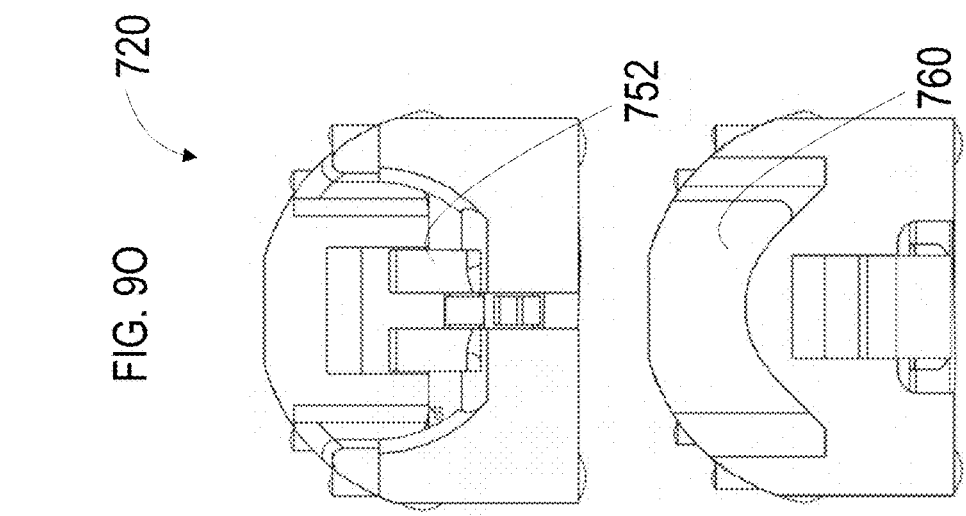
Figures 9K, 9L, 9M, 9N:
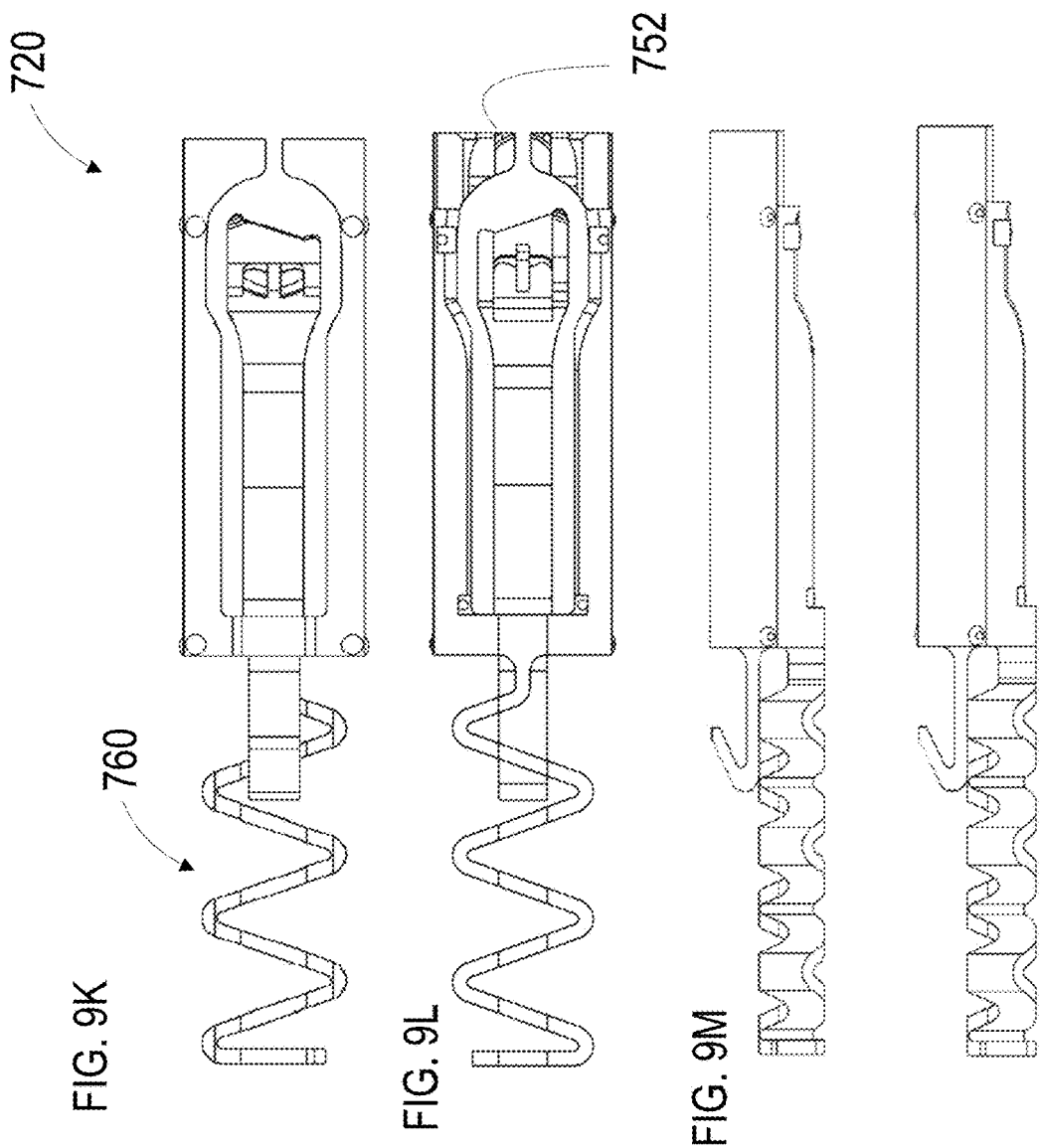

The disclosure provides still further implementations of a needle loader in accordance with the present disclosure, such as the embodiment illustrated in FIGS. 9A-9P. In such implementations, the needle loader can be a low-profile compact needle loader 700 to facilitate stacking in a container with other needle loaders to optimize space for shipment. Such needle loaders can provide a discrete compartment 710c that includes a predetermined length of suture that is attached to the arced suturing needle. In use, such a low-profile loader 700 can be aligned with a distal end portion of the suturing device (e.g., 10) and the suturing device 10 can be aligned with and introduced into a passageway 708 of the suturing device. A movable arm assembly, or movable inner assembly 720 can receive the suturing device 10 and act to displace an optional displaceable cover of the suturing device as the suturing device is advanced into the needle loader. As the suturing device is further advanced into the passageway, an arm 722 carrying a needle mount 730 with a needle removably coupled thereto can be moved into contact with a needle track of the suturing device due to an inclined surface 722a of the arm 722 sliding along a stationary boss 717 that causes the arm 722 to bend toward the needle track of the suturing device. As the needle is placed in the suturing device 10, optionally, a lock or locking element 742 can be engaged by an engagement element 712, such as a cleat, edge, boss, opening in the housing, or the like. The movable assembly 720 may be held in place by the engagement of the locking element 742 and the engagement element 712. With the suturing needle engaged by the needle track of the suturing device 10, the suturing device 10 may be withdrawn from the needle loader 700 and the arced suturing needle disengages from the needle mount 730. Suture material (not shown) can be removed from the suture compartment 710c through a groove 709 that is defined along the face of the needle loader proximate the opening 708 that connects to the suture compartment 710c. However, the housing overall has considerable stiffness to prevent groove 709 from closing if needle loader 700 is squeezed laterally from both sides. Suturing material can then be unwound from the needle loader 700 either before or during the surgical procedure. The opening 708 can be provided with one or more ridges that extend along the longitudinal axis of opening 708 to accommodate mating grooves in the suturing device that cooperatively function as an alignment feature. By way of further example, the alignment feature can be an upper groove 707 that passes into the bottom surface of the needle loader to accommodate an alignment feature of the suturing device 10, such as a keel, or lower ridge, of the suturing device. Any of these alignment features can help facilitate rotational alignment with the suturing device 10 and the needle loader 700 about a longitudinal axis of the suturing device 10 to help ensure that the arced suturing needle successfully mates with the suturing device 10.

With continuing reference to the Figures, FIGS. 9A-9B show an upper left side and lower right front side perspective views, respectively, of needle loader 700 in accordance with the present disclosure. For purposes of embodiment 700, the flattened surface illustrated in FIG. 9A is referred to herein as the "top" surface for purposes of reference. FIGS. 9C and 9D show the assembly in an inverted view to facilitate illustration, wherein FIG. 9C illustrates a sectioned view down a longitudinal direction of the loader 700 located to the "right" side of the longitudinal axis, wherein the needle loader 700 is upside down. Needle loader 700 can also include one or more contoured gripping surfaces 703 formed into the housing 810 to facilitate gripping needle loader 700 by a user when installing a needle on suturing device 10.

The housing 710 of the needle loader is composed of three main components. First, an upper concave shell portion 710e cooperates with an intermediate plate section 710d to define a cavity to receive a longitudinally movable assembly, or movable arm assembly, 720. The assembly 720 is configured to slide backward into the cavity defined by portions 710d, 710e when pushed by a suturing device 10. Forward motion of the suturing device 10 is resisted by a compression spring 760. Spring 760 traverses a serpentine path similar to springs 560 and 660.

Housing component 710d and housing component 710a, or cover plate, cooperate to form suture compartment 710c. While the entirety of the housing 710 can be made from transparent material, providing cover plate 710a as a transparent member can permit a user to view suture that is present inside of the suture compartment 710c. Component 710a is a plate shaped member having a pair of suturing winding openings 710b configured to receive a pair of suture winding bosses of a suture winding fixture (not shown) that is similar in form and function to suturing winding fixture 698. In use, bosses of the fixture are introduced through the openings 710b, and suture is wound around the bosses prior to installing plate 710a into a peripheral seat defined by the peripheral wall of component 710d. The suture can simply be wound around the bosses in an oval pattern, or can be crossed over to form a figure-8 pattern, as may be desired. After the suture is placed inside compartment 710c, the suture fixture can be removed from openings 710b, leaving the coiled suture material in place. The suture material is coupled at one end to the suturing needle, which is removably coupled by needle engagement elements 732 such as fingers, clamps, cleats and the like to suture mount 730. The suture passes from the needle through groove 709, which passes through a portion of plate 710d near the entrance 708 of the needle loader 700 and extends to the face of the device at the entrance of the loader 700, to permit the needle loader 700 to receive the arced suturing needle and have the suture trailing from the needle pass through the portion of groove 709 that passes through the plate 710d. When the needle loader 700 has deposited the suturing needle into the suturing device 10, the suturing device can be withdrawn, and the suture that trails from the needle passes into the suture compartment, and can be withdrawn through the portion of groove 709 that extends from the entrance 708 of the needle loader 700 to the suture compartment 710c.

With continuing reference to FIG. 9C, as the suturing device 10 is advanced into opening 708, assembly 720 is pushed back into the housing 710, and inclined surface 722a of arm 722 rides over the upper surface of boss 717. This causes the needle mount 730 bearing the needle to be pushed into contact with the distal end portion of the suturing device to place first and second ends of the needle into first and second ends of the needle track. When this engagement has completed, arm assembly 720 has been pushed back far enough into the housing 710 to permit the optional locking element 742 to slide over and engagement element 712 and snap in place, holding arm assembly 720 in place with spring 760 in a compressed state.

FIG. 9D presents a lower perspective view of the arm assembly 720. Arm assembly includes a central portion 723 to which other components of the arm assembly attach. Central portion 723 includes a backwardly extending spring 760 attached thereto that traverses a serpentine path that resists a longitudinal compressive load. The spring 760 has a cross sectional shape that is crescent shaped, which is best viewed in the end view of FIG. 9P. This shaping is to permit locking feature 742 to prevent collision with the windings of spring 760 as spring 760 is compressed.

With continuing reference to FIG. 9D, a pair of arms 724 extend in a direction opposite the direction of the spring, toward the opening of the passageway 708 of the needle loader 700. Each arm 724 is generally planar in shape and slides against inner walls of the housing 710. Each arm 724 terminates in a protrusion 752 that receives a distal end portion of the suturing device and urges against the sliding cover of the suturing device 10 to displace the cover and expose the needle track as the suturing device 10 is being advanced along the passage 708. The protrusions 752 at the free end of each arm 724 define a gap 729 therebetween to permit a suture to pass through. Gap 729 cooperates with gap 709 to permit the suture to pass therethrough that is attached to the suturing needle and helps prevent interference as the suturing device 10 is being withdrawn from the needle loader 700 after the suturing device 10 has been loaded with an arced suturing needle. Elongate arm 722 also extends proximally from the central region 723 of the arm assembly 720. Arm 722 terminates in needle mount 730, as described above. Arm 722 includes an inclined surface 722a to facilitate movement of the needle mount 730 from a first position displaced from the suturing device along a direction orthogonal to the direction of travel of the suturing device 10 along the passage 708 to a second position wherein the needle mount 730 contacts the distal end portion of the suturing device 10. Stated another way, provided with the spatial reference frame wherein the needle loader 700 is "upright" in FIG. 9A, during loading, the inclined surface 722a of the arm 722 pushes the needle mount with needle mounted thereon downwardly into contact with the suturing device 10 in the orientation in FIG. 9A (corresponding to upward motion in the orientation depicted in FIG. 9C).

FIGS. 9E-9F present upper isometric views of the arm assembly 920. Locking feature 942 is disposed at the top of the arm assembly, when considering that the device 700 is upright in FIG. 9A, and the spring 760 slides along a bottom of the housing 710 of the needle loader. With reference to FIG. 9G, a proximal end face 724a of arms 724 is shown, each of which terminates in a protrusion surface 752 that engages the cover of the suturing device 10, and a pair of ramped features 754 that urge against the end face of the retractable cover of the suturing device. FIGS. 9H-9J present aspects of a cross sectional view of the movable arm assembly 720 of the suturing device 700. The plane specifying the cross section is specified in FIG. 9H, and upper and lower isometric section views are shown illustrating relative placement of the needle mount 730 and the needle retention features 732. FIGS. 9K, 9L, 9M, 9N, 9O, and 9P present a top plan view, a bottom plan view, a right-side elevational view, a left side elevational view, a front side elevational view and a rear side elevational view, respectively, of arm assembly 720.

The disclosure provides additional implementations of a needle loader 800 in accordance with the present disclosure illustrated in FIGS. 10A-11F. Needle loader 800 presents an implementation of an ergonomic needle loader with a rounded back end to fit in the palm of the hand of a user. Needle loader 800 can also include one or more contoured gripping surfaces 803 formed into the housing 810 to facilitate gripping needle loader 800 by a user when installing a needle on suturing device 10. Needle loader 800 optionally can include a discrete compartment 890 that includes a predetermined length of suture 899 that is attached to the arced suturing needle. In use needle loader 800 is aligned with a distal end portion of the suturing device (e.g., 10) and the suturing device 10 can be aligned with an introduced into a passageway 808 of the suturing device. A movable arm assembly, or movable inner assembly 820 can receive the suturing device 10 and act to displace a displaceable cover of the suturing device as the suturing device is advanced into the needle loader.

As the suturing device 10 is further advanced into the passageway 808, an arm 822 carrying a needle mount 830 with a needle removably coupled thereto can be moved into contact with a needle track of the suturing device 10 due to an inclined surface 822a of the arm 822 sliding along a stationary boss 817 that causes the arm 822 to bend toward the needle track of the suturing device. As the needle is placed in the suturing device, lock or locking elements 842a, can be engaged by an engagement element 812 (FIG. 11D), such as a cleat, edge, boss, opening in the housing, or the like. The movable assembly 820 may be held in place by the engagement of the locking element 842a and the engagement element 812. With the suturing needle engaged by the needle track of the suturing device 10, the suturing device 10 may be withdrawn from the needle loader 800 and the arced suturing needle disengages from the needle mount 830. Suture material (not shown) can be removed from the suture compartment 890 through a groove 809 that is defined along the face of the needle loader proximate the opening 808 that connects to the suture compartment 890. Suturing material 899 can then be unwound from the needle loader 800 either before or during the surgical procedure.

With continuing reference to the Figures, FIGS. 10A-10C show a lower left perspective view, a lower front perspective view and a left side schematic view, respectively, of needle loader 800. For purposes of reference herein, embodiment 800 is disposed in an "upright" position in FIGS. 10A-10C.

Figure 10D:
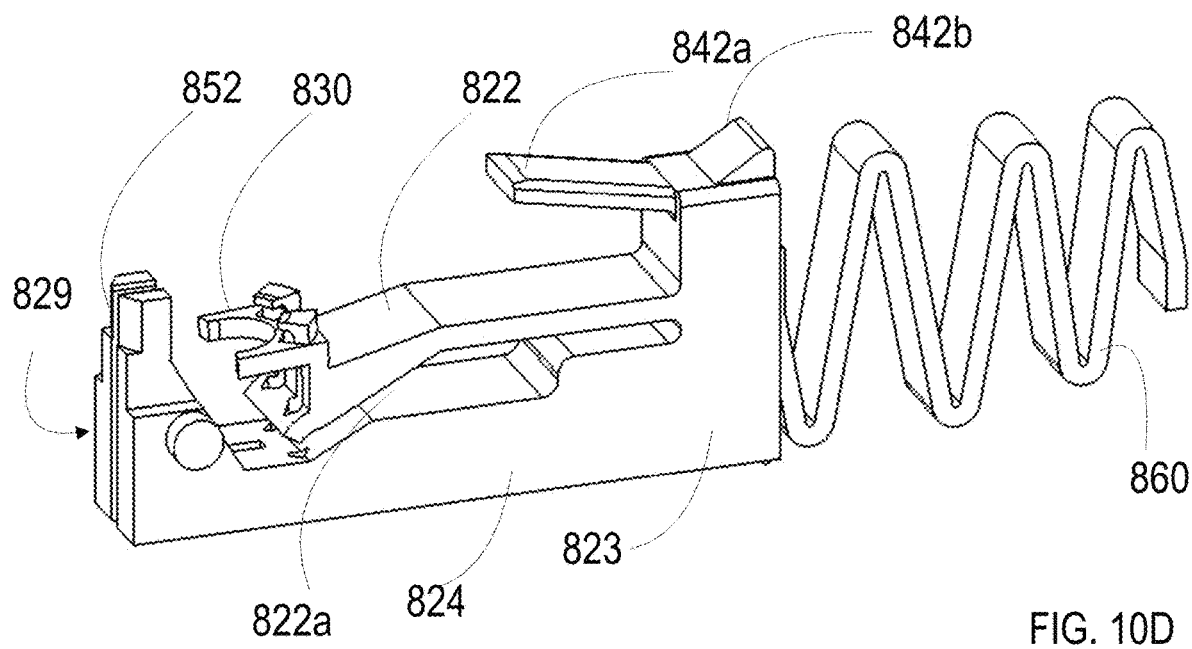
FIGS. 10A-11D depict views of a needle loader device in accordance with some embodiments of the present disclosure, or aspects thereof.
Figure 10E:
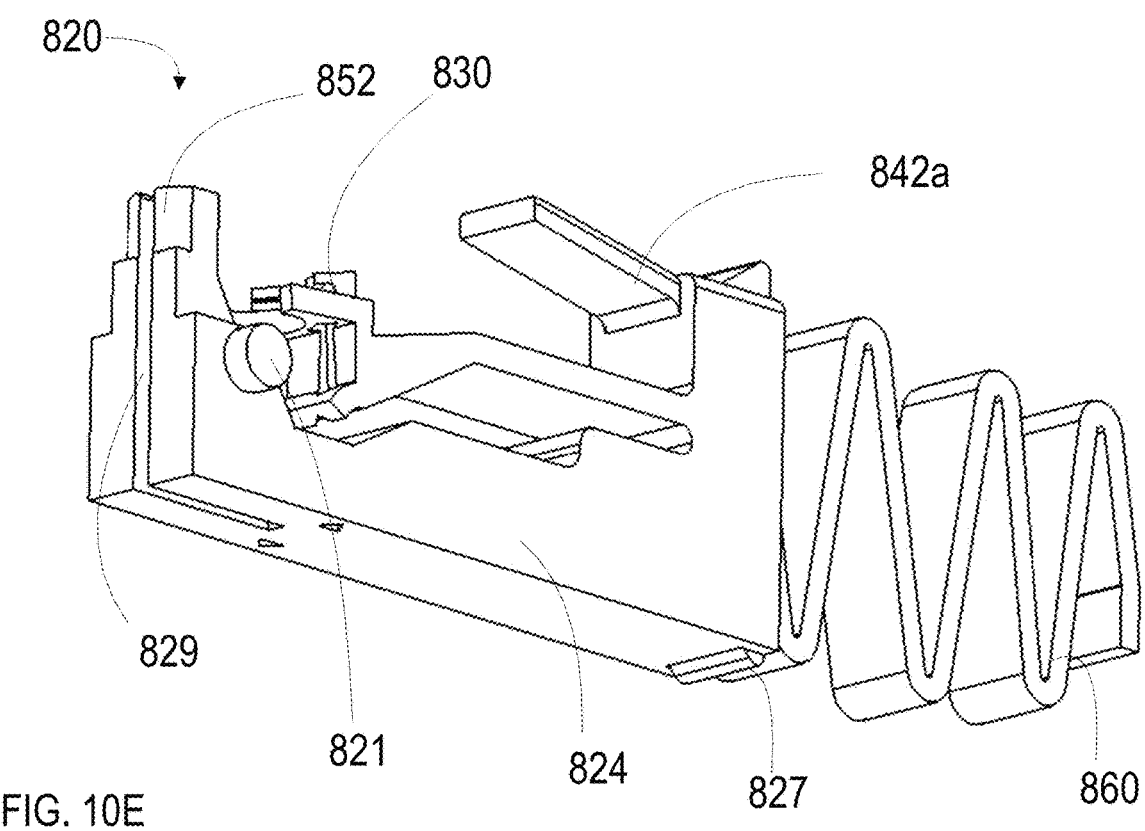
Figure 10F:
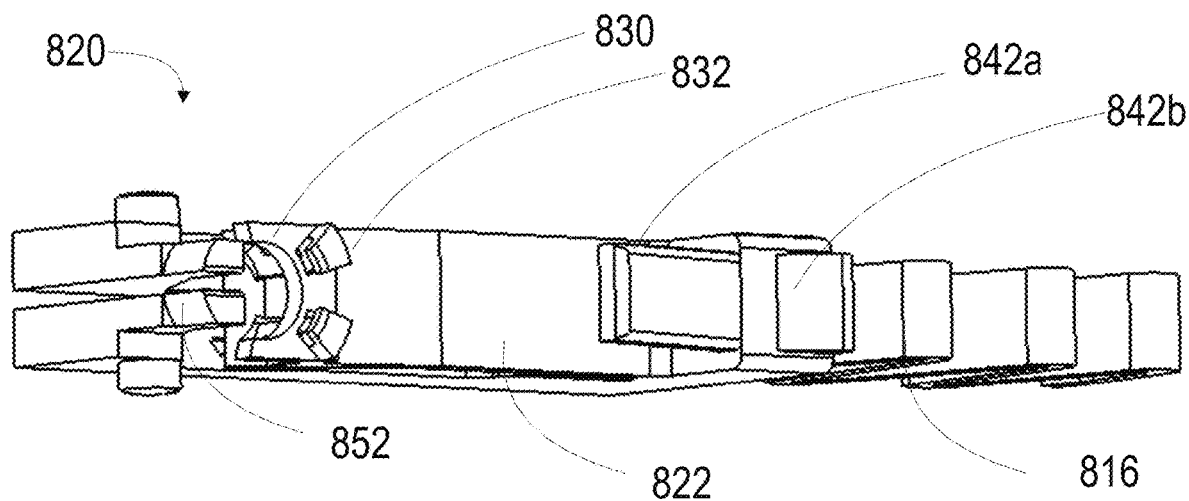
Figure 10G:
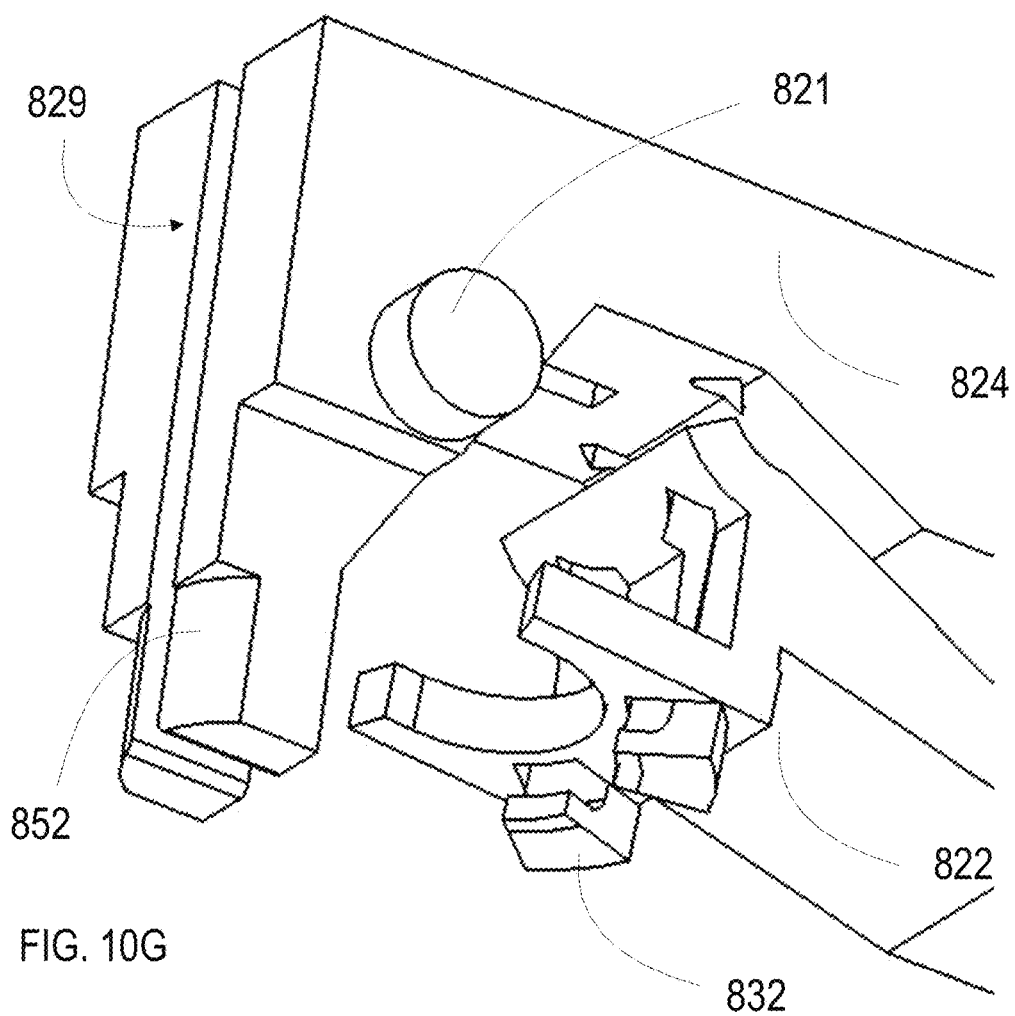
Figure 10H:
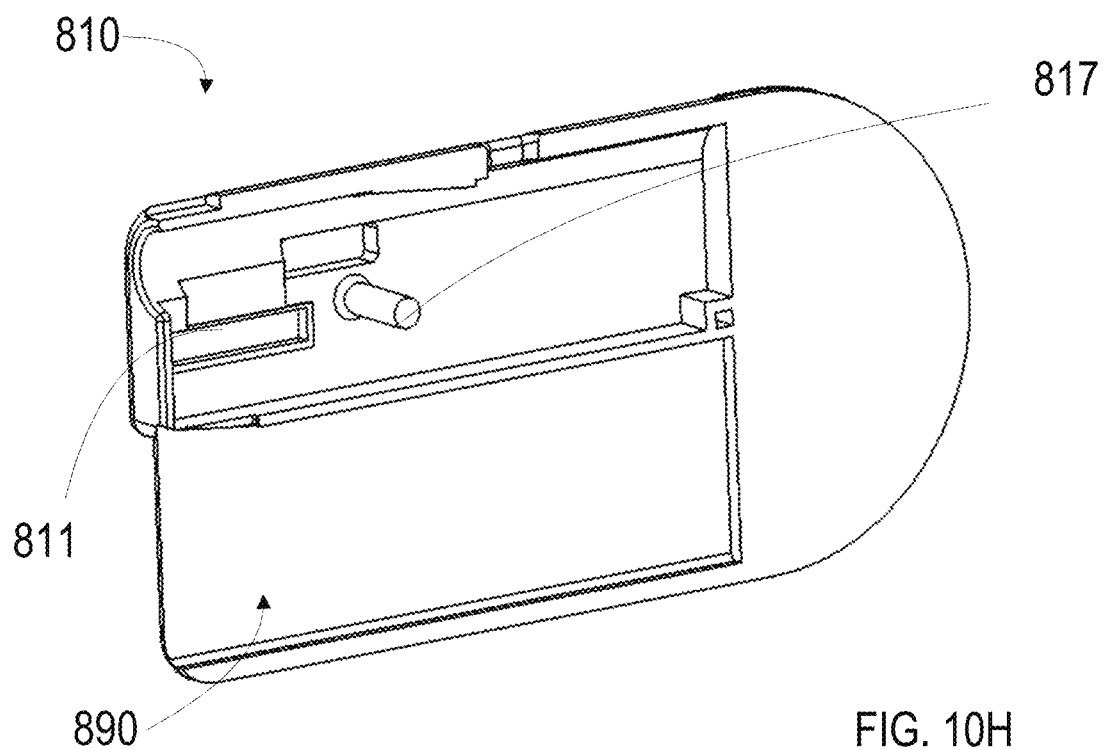
Figure 10I:
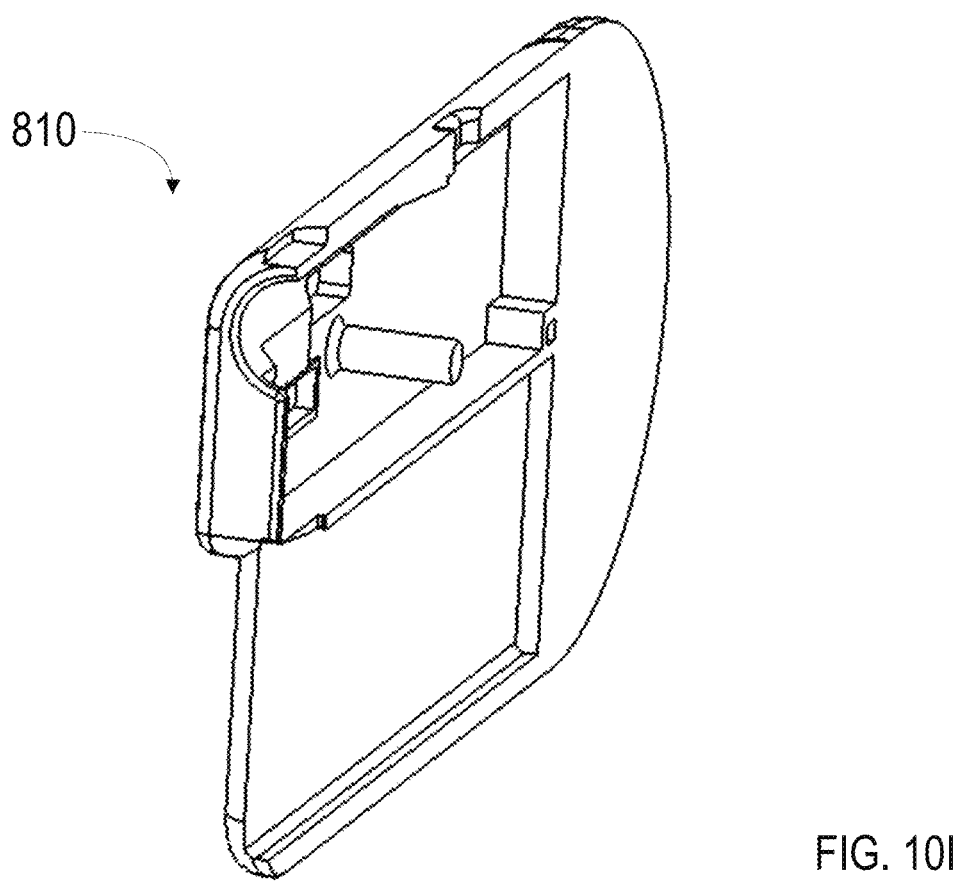

The housing 810 of the needle loader 800 is composed of two generally symmetrical halves, wherein the left side half is illustrated in FIGS. 10H-10I. The two housing halves cooperate to form a cavity to receive the movable assembly 820, and a second compartment 890 to receive the suture 899. The arm assembly 820 is configured to slide backward into the cavity defined by housing portions when pushed by a suturing device 10. Forward motion of the suturing device 10 is resisted by a compression spring 860. Spring 860 traverses a serpentine path similar to springs 560 660, and 760.

The suture material 899 is coupled at one end to the suturing needle, which is removably coupled by needle engagement elements 832 such as fingers, clamps, cleats and the like to suture mount 830. The suture 899 passes from the needle through groove 809, which passes through a gap defined between the two portions of the housing 810. This arrangement permits the needle loader 800 to receive the arced suturing needle and have the suture trailing from the needle pass through the groove 809 after the suturing device 10 is withdrawn from the needle loader 800. Consequently, after the needle loader 800 has deposited the suturing needle into the suturing device 10, the suturing device 10 can be withdrawn, and the suture 899 that trails from the needle passes into the suture compartment and can be withdrawn through the portion of groove 809.

With continuing reference to the figures, as the suturing device 10 is advanced into opening 808, assembly 820 is pushed back into the housing 810, and inclined surface 822a of arm 822 rides over the upper surface of boss 817. This causes the needle mount 830 bearing the needle to be pushed into contact with the distal end portion of the suturing device to place first and second ends of the needle into first and second ends of the needle track of the suturing device 10. When this engagement has completed, arm assembly 820 has been pushed back far enough into the housing 810 to permit the locking element 842a to slide over and engagement element 812 and snap in place, holding arm assembly 820 in place with spring 860 in a compressed state. It will be appreciated that a surface of locking element 842a can act as one or more visual indicium if engagement element 812 is a window formed into the wall of the housing 810, as illustrated in FIG. 11D.

Arm assembly 820 includes a central portion 823 to which other components of the arm assembly 820 attach. Central portion 823 includes a backwardly extending spring 860 attached thereto that traverses a serpentine path that resists a longitudinal compressive load.

With continuing reference to FIGS. 10D-10G, a pair of arms 824 extend in a direction opposite the direction of the spring, toward the opening of the passageway 808 of the needle loader 800. Each arm 824 is generally planar in shape and cooperate to define a gap 829 therebetween to accommodate passage of suture 899 that trails from the needle and into the suture compartment 890. Arms 824 slide against inner walls of the housing 810. A further boss 842c is provided on an underside of arm assembly to prevent proximal motion of the arm assembly. Each arm 824 terminates in a protrusion 852 that receives a distal end portion of the suturing device and urges against the sliding cover of the suturing device 10 to displace the cover and expose the needle track as the suturing device 10 is being advanced along the passage 808. The protrusions 852 at the free end of each arm 824 also cooperate to define gap 829 therebetween to permit the suture 899 to pass therethrough. Elongate arm 822 also extends proximally from the central region 823 of the arm assembly 820. Arm 822 terminates in needle mount 830, as described above. Arm 822 includes an inclined surface 822a to facilitate movement of the needle mount 830 from a first position displaced from the suturing device to a second position wherein the needle mount 830 contacts the distal end portion of the suturing device 10. Bosses 821 are provided on arm assembly 820 that are slidably received in respective guide tracks 811 in the inner surfaces of housing 810.

Figure 11A:
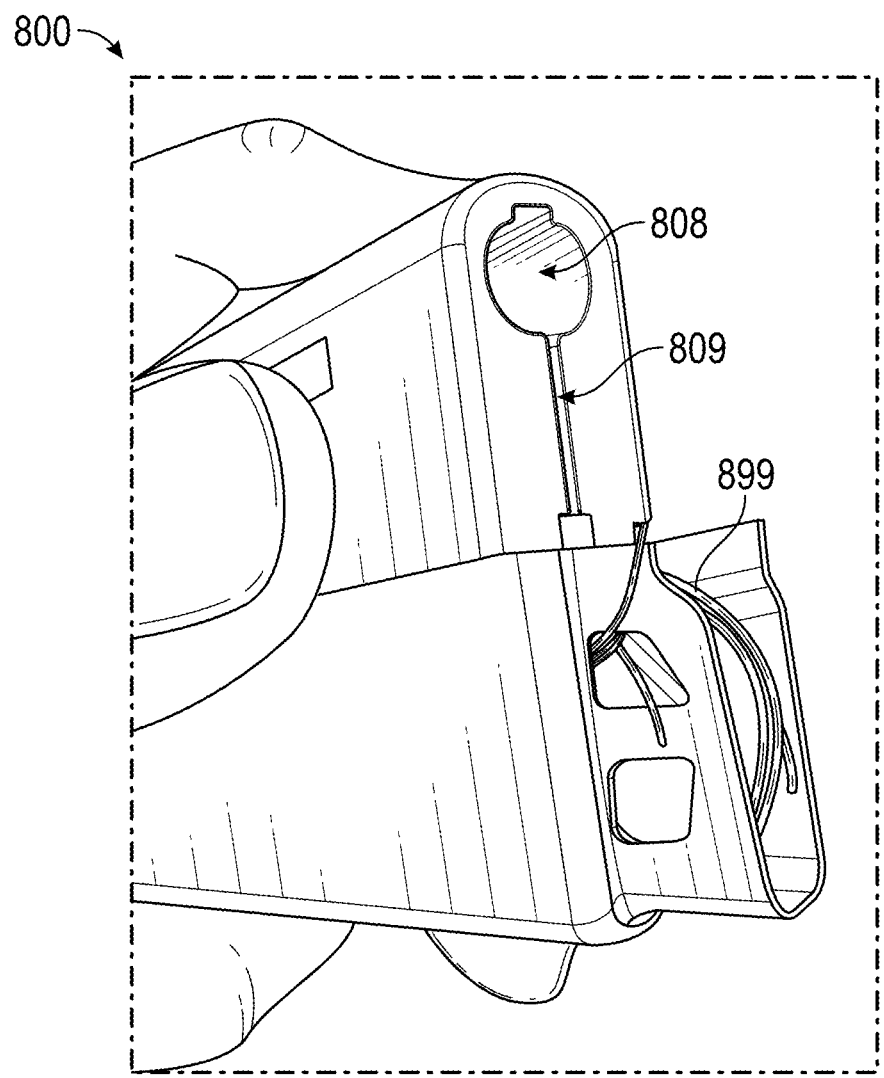
FIGS. 11E-11F depict views of a needle loader device in accordance with some embodiments of the present disclosure, or aspects thereof.
Figure 11B:
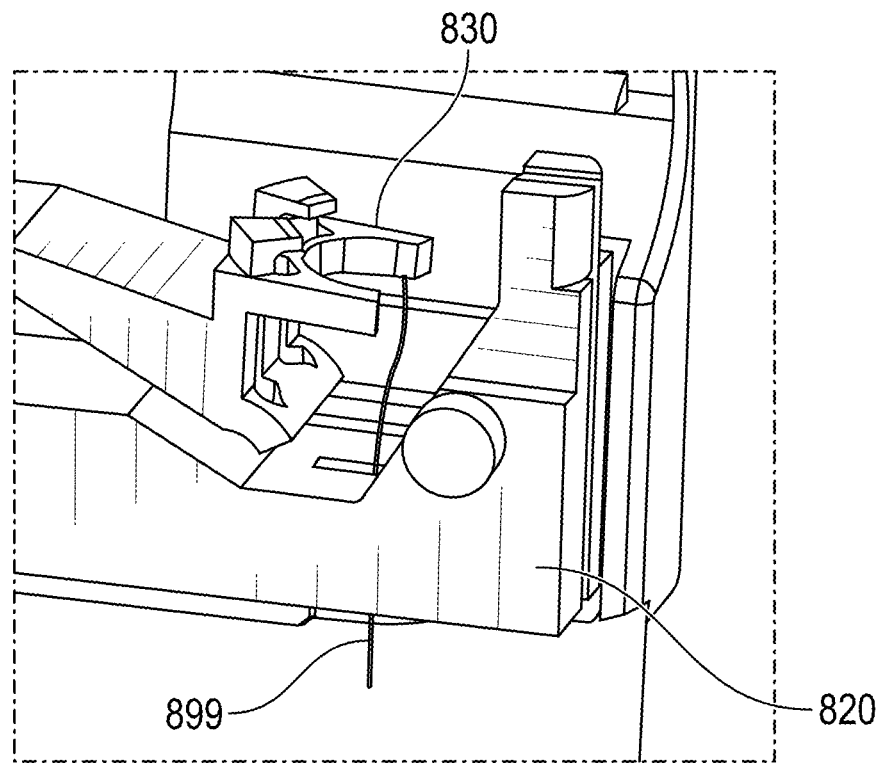
Figure 11C:
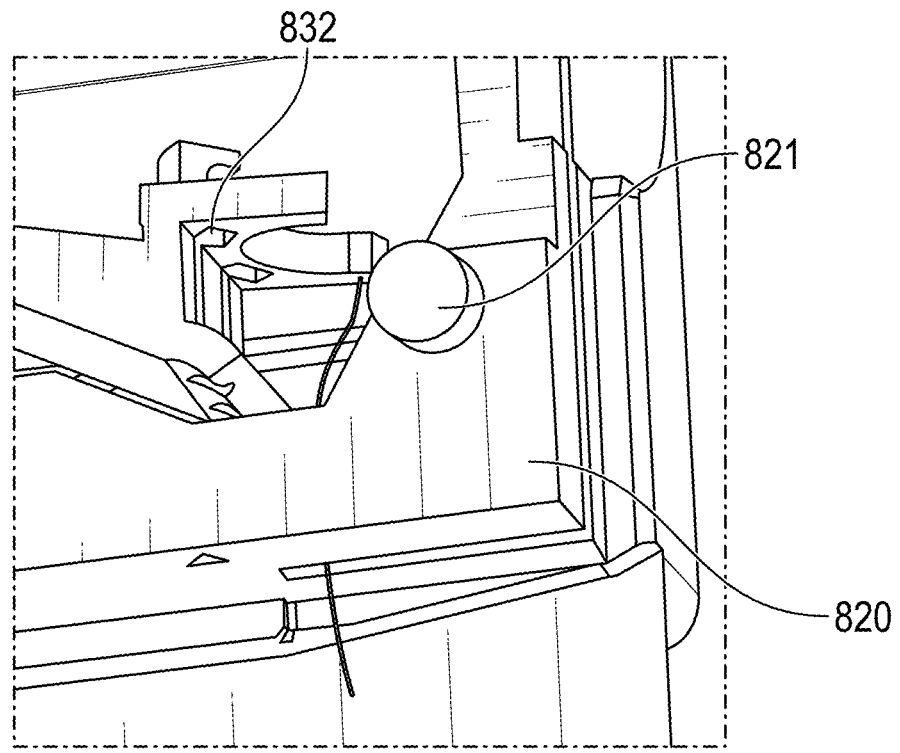
Figure 11D:
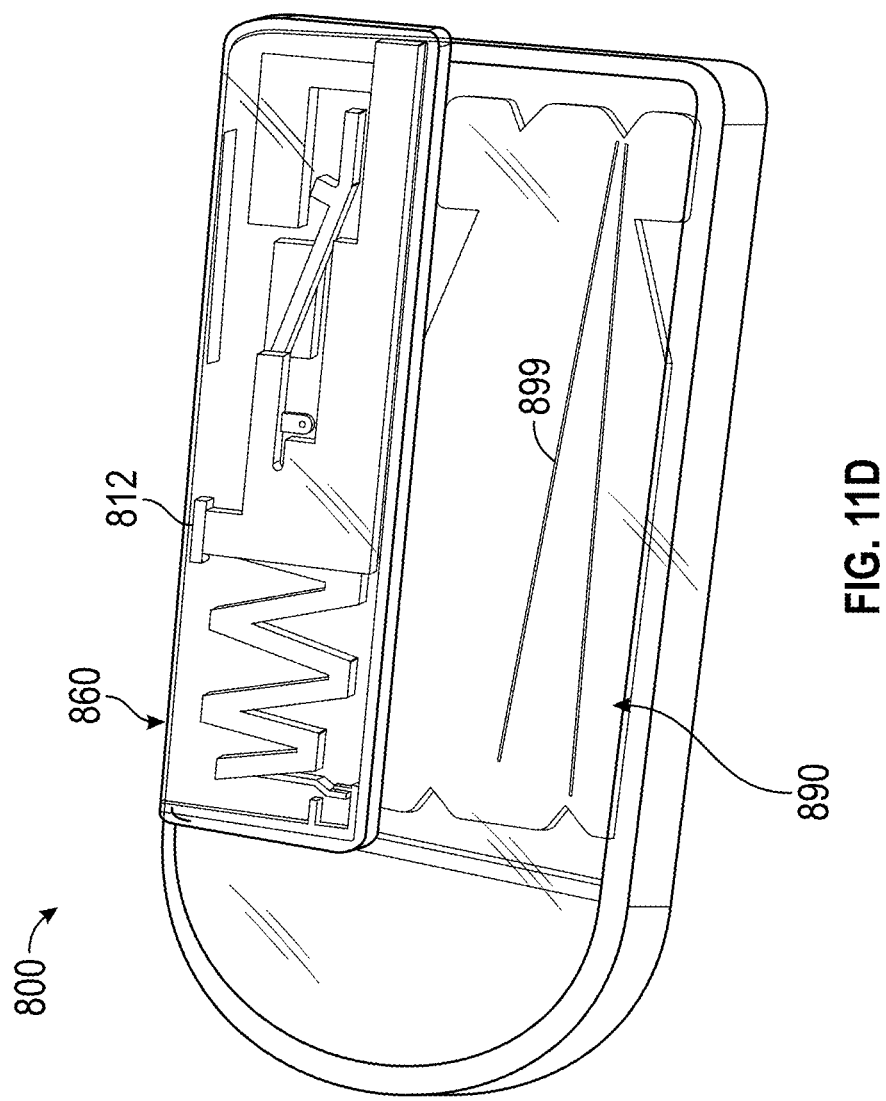

FIG. 11A illustrates a further view of needle loader 800 in use, with a packet of suture 899 disposed partially within compartment 890. FIGS. 11B and 11C are partial upper and lower isometric views of arm assembly 824 showing routing of a suture 899 through slot 829. FIG. 11D is a side view of a representative implementation of needle loader 800 illustrating relative placement of suture material 899 in compartment 890.

Figure 11E:
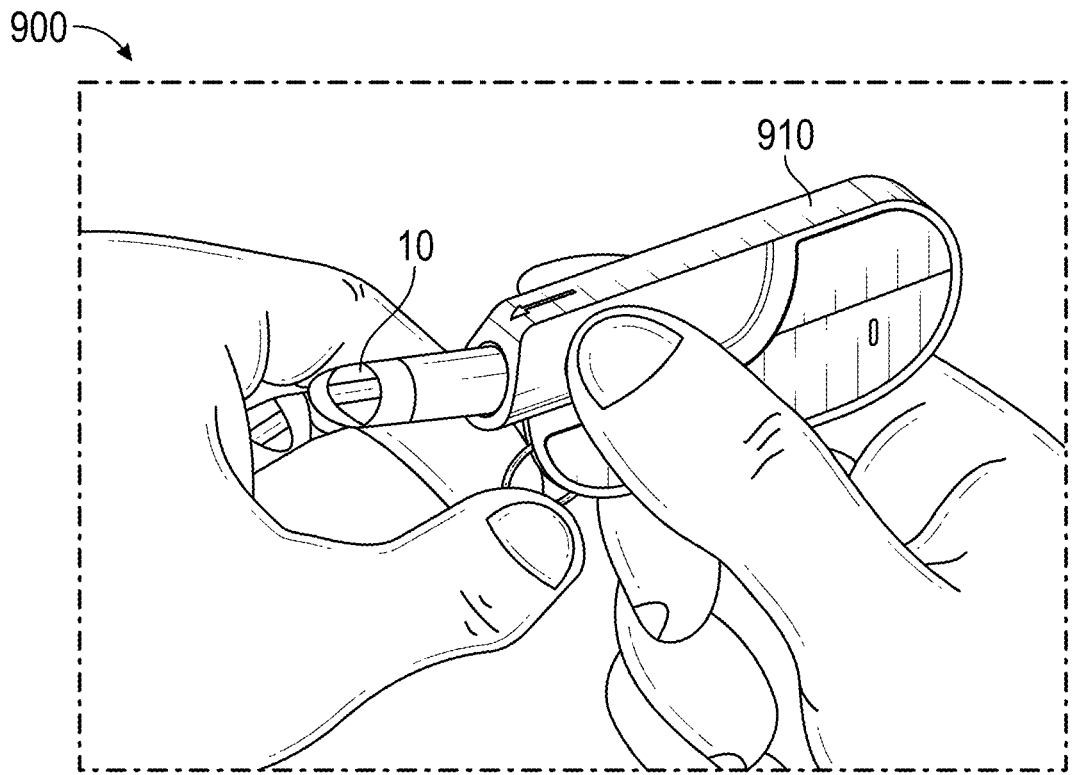
Figure 11F:
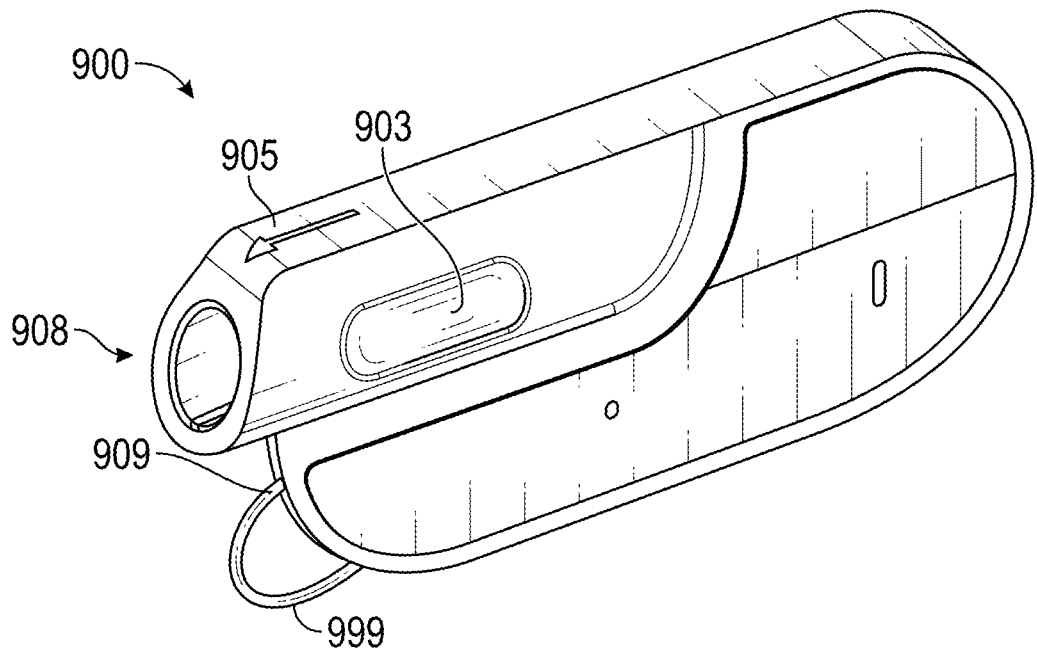

FIGS. 11E-11F illustrate a further implementation of a needle loader 900 that is a variation of the needle loader 800, wherein needle loader 900 includes a streamlined ergonomic housing 910 having one or more gripping contours or surfaces 903. FIG. 11E illustrates placement of suturing device 10 into the opening 908 of needle loader 900, and FIG. 11F is a front side upper isometric view of needle loader 900 illustrating a gripping surface 903 on the housing 910 of the needle loader and groove 909, similar to groove 809, that permits suturing material 999 in a lower compartment to be removed from the needle loader 900 as the suturing material 999 is used. Also depicted is an indicia 905 located on an upper surface of the housing 910 to guide placement and direction of the needle loader 900 with respect to the suturing device 10. The interior components and layout of needle loader can be the same or substantially the same as needle loader 800.

Each embodiment of needle loader (100, 200, 300, 400, 500, 600, 700, 800) can be provided with additional features as described in other embodiments, such as lock devices, visual or tactile indicators, suture compartments, and the like. Moreover, each such embodiment can be provided in a sterile kit that is ready to be opened upon use in a procedure. The kit may be a single use device or may be reprocessed and reloaded with a new/sterilized needle. Where possible, components are preferably integrally molded to reduce the number of parts needed for each given device. The needle loaders are preferably made from suitably selected injection molded plastic material.

Embodiments described herein may be used, for example, with remotely operated, computer-assisted systems (such, for example, teleoperated surgical systems) such as those described in, for example, U.S. Pat. No. 9,358,074 (filed May 31, 2013) to Schena et al., entitled "Multi-Port Surgical Robotic System Architecture", U.S. Pat. No. 9,295,524 (filed May 31, 2013) to Schena et al., entitled "Redundant Axis and Degree of Freedom for Hardware-Constrained Remote Center Robotic Manipulator", and U.S. Pat. No. 8,852,208 (filed Aug. 12, 2010) to Gomez et al., entitled "Surgical System Instrument Mounting", each of which is hereby incorporated by reference in its entirety. Further, embodiments described herein may be used, for example, with a da Vinci® Surgical System, such as the da Vinci Xi® Surgical System or the da Vinci Xi® Surgical System commercialized by Intuitive Surgical, Inc., of Sunnyvale, California Although various embodiments described herein are discussed in connection with a manipulating system of a teleoperated surgical system, the present disclosure is not limited to use with a teleoperated surgical system. Various embodiments described herein can optionally be used in conjunction with hand-held, manual instruments.

As discussed above, in accordance with various embodiments, surgical instruments of the present disclosure are configured for use in teleoperated, computer-assisted surgical systems employing robotic technology (sometimes referred to as robotic surgical systems). Referring now to FIG. 12, an embodiment of a manipulator system 1200 of a computer-assisted surgical system, to which surgical instruments are configured to be mounted for use, is shown. Such a surgical system may further include a user control system, such as a surgeon console (not shown) for receiving input from a user to control instruments coupled to the manipulator system 1200, as well as an auxiliary system, such as auxiliary systems associated with the DA VINCI SI® and DA VINCI XI®, Da Vinci SP, and Ion systems noted above.

As shown in the embodiment of FIG. 12, a manipulator system 1200 includes a base 1220, a main column 1240, and a main boom 1260 connected to main column 1240. Manipulator system 1200 also includes a plurality of manipulator arms 1210, 1211, 1212, 1213, which are each connected to main boom 1260. Manipulator arms 1210, 1211, 1212, 1213 each include an instrument mount portion 1222 to which an instrument 1230 may be mounted, which is illustrated as being attached to manipulator arm 1210.

Instrument mount portion 1222 comprises a drive assembly 1223 and a cannula mount 1224, with a transmission mechanism 1234 of the instrument 1230 (similar to suturing device 10 described hereinabove) connecting with the drive assembly 1223, according to an embodiment. Cannula mount 1224 is configured to hold a cannula 1236 through which a shaft 1232 of instrument 1230 may extend to a surgery site during a surgical procedure. Drive assembly 1223 contains a variety of drive and other mechanisms that are controlled to respond to input commands at the surgeon console and transmit forces to the transmission mechanism 1234 to actuate the instrument 1230. Although the embodiment of FIG. 12 shows an instrument 1230 attached to only manipulator arm 1210 for ease of viewing, an instrument may be attached to any and each of manipulator arms 1210, 1211, 1212, 1213.

Other configurations of surgical systems, such as surgical systems configured for single-port surgery, are also contemplated. For example, with reference now to FIG. 13, a portion of an embodiment of a manipulator arm 2140 of a manipulator system with two surgical instruments 2300, 2310 in an installed position is shown. The surgical instruments 2300, 2310 can generally correspond to instruments discussed above, such as suturing device 10 described elsewhere herein. A. For example, the embodiments described herein may be used with a DA VINCI SP® Surgical System, commercialized by Intuitive Surgical, Inc. of Sunnyvale, California. The schematic illustration of FIG. 13 depicts only two surgical instruments for simplicity, but more than two surgical instruments may be mounted in an installed position at a manipulator system as those having ordinary skill in the art are familiar with. Each surgical instrument 2300, 2310 includes a shaft 2320, 2330 that at a distal end has a moveable end effector or an endoscope, camera, or other sensing device, and may or may not include a wrist mechanism (not shown) to control the movement of the distal end.

In the embodiment of FIG. 13, the distal end portions of the surgical instruments 2300, 2310 are received through a single port structure 2380 to be introduced into the patient. As shown, the port structure includes a cannula and an instrument entry guide inserted into the cannula. Individual instruments are inserted into the entry guide to reach a surgical site.

Other configurations of manipulator systems that can be used in conjunction with the present disclosure can use several individual manipulator arms. In addition, individual manipulator arms may include a single instrument or a plurality of instruments. Further, as discussed above, an instrument may be a surgical instrument with an end effector or may be a camera instrument or other sensing instrument utilized during a surgical procedure to provide information, (e.g., visualization, electrophysiological activity, pressure, fluid flow, and/or other sensed data) of a remote surgical site.

Transmission mechanisms 2385, 2390 are disposed at a proximal end of each shaft 2320, 2330 and connect through a sterile adaptor 2400, 2410 with drive assemblies 2420, 2430. Drive assemblies 2420, 2430 contain a variety of internal mechanisms (not shown) that are controlled by a controller (e.g., at a control cart of a surgical system) to respond to input commands at a surgeon side console of a surgical system to transmit forces to the force transmission mechanisms 2385, 2390 to actuate surgical instruments 2300, 2310.

The embodiments described herein are not limited to the embodiments of FIG. 12 and FIG. 13, and various other teleoperated, computer-assisted surgical system configurations may be used with the embodiments described herein. The diameter or diameters of an instrument shaft and end effector are generally selected according to the size of the cannula with which the instrument will be used and depending on the surgical procedures being performed.

This description and the accompanying drawings that illustrate various embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to another embodiment, the element may nevertheless be claimed as included in the other embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the illustrative term "below" can encompass both positions and orientations of above and below. A device may be otherwise oriented (rotated 90 degrees or at other orientations) and the spatially relative descriptors used herein interpreted accordingly.

Further modifications and alternative embodiments will be apparent to those of ordinary skill in the art in view of the disclosure herein. For example, the devices and methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as illustrative. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as illustrative and for example only, with the following claims being entitled to their fullest breadth, including equivalents, under the applicable law.

What is claimed is:

1. A needle loader, comprising:
   a housing;
   a movable arm disposed within the housing, wherein the movable arm is slidably disposed along a first direction along a length of a cavity defined within the housing; and
   a needle mount defined on the movable arm to releasably attach to at least a portion of a suturing needle, wherein the needle mount and the at least a portion of the suturing needle are configured to deflect within the cavity along a second direction that is different from the first direction while the needle mount and the at least a portion of the suturing needle slide along the first direction from a first position to a second position, wherein the needle mount and the at least a portion of the suturing needle are spaced apart from a needle track of a suturing device in the first position, and wherein the needle mount and the at least a portion of the suturing needle are adjacent the needle track of the suturing device in the second position.

2. The needle loader of claim 1, further comprising at least a portion of a suturing needle releasably attached to the needle mount.

3. The needle loader of claim 2, wherein the at least a portion of the suturing needle comprises at least a portion of an arced suturing needle, and further wherein the at least a portion of the arced suturing needle is held in place and attached to the needle mount by way of an interference fit.

4. The needle loader of claim 1, wherein the needle mount is configured to lock in position after the needle mount has reached the second position.

5. The needle loader of claim 1, wherein the needle mount intersects the needle track of the suturing device when the needle mount and the at least a portion of the suturing needle have reached the second position, and further wherein the needle loader further comprises a spring that is configured to urge against motion of the needle mount as the needle mount moves from the first position toward the second position.

6. The needle loader of claim 1, wherein the movable arm includes a cammed surface that is configured to slide over a distal portion of the suturing device as the needle mount and the at least a portion of the suturing needle approaches the second position.

7. The needle loader of claim 1, wherein movement of the needle mount and the at least a portion of the suturing needle to the second position activates an indicator confirming that the needle mount and the at least a portion of the suturing needle have reached the second position.

8. The needle loader of claim 7 wherein the indicator confirms that the needle mount at the least a portion of the suturing needle have reached the second position by displaying visual indicia.

9. The needle loader of claim 1, further comprising a protrusion that extends into a path of the suturing device to be loaded with the at least a portion of the suturing needle from the needle loader, wherein the protrusion is configured to cause the needle track of the suturing device to be exposed as the suturing device is advanced along the path, and further wherein the suturing device includes a retractable cover to cover the needle track, and still further wherein the protrusion is configured to retract the retractable cover of the suturing device to expose the needle track.

10. The needle loader of claim 1, wherein the second direction is non-linear.

11. The needle loader of claim 1, wherein the movable arm bends along the second direction while the movable arm, the needle mount, and the at least a portion of the suturing needle slide from the first position to the second position, and further wherein the first direction is linear.

12. The needle loader of claim 1, wherein the second direction is oblique or orthogonal with respect to the first direction.

13. A device for loading at least a portion of a suturing needle into a suturing device, comprising:
   a mount defining at least one indentation therein, the indentation being configured to receive at least a portion of the suturing needle therein in an interference fit, wherein the mount is configured to slide along a first direction from a first position wherein the mount and the at least a portion of the suturing needle is out of contact with a needle track of a suturing device, to a second position wherein the mount is adjacent the needle track of the suturing device and the at least a portion of the suturing needle is deposited into the needle track of the suturing device; and an elongate shaft extending from the mount, wherein the elongate shaft is configured to slide with the mount along a portion of the suturing device along the first direction as the mount and the at least a portion of the suturing needle is advanced from the first position to the second position, and further wherein the elongate shaft, the mount, and the at least a portion of the suturing needle are configured to deflect along a second direction that is different from the first direction as the mount and the at least a portion of the suturing needle are slid from the first position to the second position.

14. The device of claim 13, wherein the mount defines at least one guide boss thereon configured to be received by a guide track.

15. The device of claim 13, wherein the at least a portion of the suturing needle includes a sharpened leading end.

16. The device of claim 13, wherein at least a portion of the elongate shaft comprises a laterally deformable body, wherein the laterally deformable body is configured to be bent from a first shape into a second shape as the mount is advanced from the first position to the second position.

17. The device of claim 13, wherein the mount includes a magnet and the at least a portion of the suturing needle includes ferromagnetic material, and further wherein the magnet is configured to hold the at least a portion of the suturing needle in place until the at least a portion of the suturing needle is deposited in the needle track of the suturing device.

18. The device of claim 13, wherein the device further comprises an indicator to indicate that the at least a portion of the suturing needle has been loaded into the needle track of the suturing device.

19. The device of claim 18, wherein the indicator includes a tactile indicator.

20. The device of claim 13, wherein the second direction is non-linear.

21. The device of claim 13, wherein the elongate shaft bends along the second direction while the elongate shaft, mount and the at least a portion of the suturing needle slide from the first position to the second position, and further wherein the first direction is linear.

22. The device of claim 13, wherein the second direction is oblique or orthogonal with respect to the first direction.

* * * * *